(12) United States Patent
Osorio

(10) Patent No.: US 8,562,523 B2
(45) Date of Patent: Oct. 22, 2013

(54) DETECTING, ASSESSING AND MANAGING EXTREME EPILEPTIC EVENTS

(75) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 304 days.

(21) Appl. No.: 13/040,996

(22) Filed: Mar. 4, 2011

(65) Prior Publication Data

US 2012/0226108 A1 Sep. 6, 2012

(51) Int. Cl.
A61B 5/02 (2006.01)

(52) U.S. Cl.
USPC .......................................... 600/300; 600/483

(58) Field of Classification Search
USPC ............. 600/16, 17, 300, 483, 509, 515–519; 607/45
See application file for complete search history.

(56) References Cited

U.S. PATENT DOCUMENTS

| 4,295,474 A | 10/1981 | Fischell |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,979,511 A | 12/1990 | Terry, Jr. |
| 5,025,807 A | 6/1991 | Zabara |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |

(Continued)

FOREIGN PATENT DOCUMENTS

| EP | 0944411 | 4/2001 |
| EP | 1486232 | 12/2004 |

(Continued)

OTHER PUBLICATIONS

Osorio, I. et al., "Toward a Quantitative Multivariate Analysis of the Efficacy of Antiseizure Therapies," Epilepsy & Behavior, Academic Press, San Diego, CA., vol. 18, No. 4, Aug. 1, 2010, pp. 335-343.

(Continued)

Primary Examiner — Brian T Gedeon

(57) ABSTRACT

Methods and apparatus for identifying an extreme epileptic state/event in a patient are provided. One method includes determining at least one of an autonomic index, a neurologic index, a metabolic index, an endocrine index, or a tissue stress index, where at least one determined index is based upon body data. The method also includes identifying a seizure event based upon the at least one determined index and determining at least one seizure severity index (SSI) value indicative of the severity of the seizure event. The method further includes comparing the determined at least one SSI value to at least one reference value and identifying an occurrence of an extreme seizure event, based upon the comparison of the determined SSI value to the at least one reference value.

29 Claims, 21 Drawing Sheets

(56) References Cited

U.S. PATENT DOCUMENTS

| | | |
|---|---|---|
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,307,263 A | 4/1994 | Brown |
| 5,330,507 A | 7/1994 | Schwartz |
| 5,330,515 A | 7/1994 | Rutecki et al. |
| 5,335,657 A | 8/1994 | Terry, Jr. et al. |
| 5,357,427 A | 10/1994 | Langen et al. |
| 5,441,047 A | 8/1995 | David et al. |
| 5,522,862 A | 6/1996 | Testerman et al. |
| 5,531,778 A | 7/1996 | Maschino et al. |
| 5,540,730 A | 7/1996 | Terry, Jr. et al. |
| 5,540,734 A | 7/1996 | Zabara |
| 5,544,649 A | 8/1996 | David et al. |
| 5,544,661 A | 8/1996 | Davis et al. |
| 5,553,609 A | 9/1996 | Chen et al. |
| 5,571,150 A | 11/1996 | Wernicke et al. |
| 5,601,435 A | 2/1997 | Quy |
| 5,690,681 A | 11/1997 | Geddes et al. |
| 5,700,282 A | 12/1997 | Zabara |
| 5,707,400 A | 1/1998 | Terry, Jr. et al. |
| 5,720,771 A | 2/1998 | Snell |
| 5,722,999 A | 3/1998 | Snell |
| 5,743,860 A | 4/1998 | Hively et al. |
| 5,759,199 A | 6/1998 | Snell et al. |
| 5,916,239 A | 6/1999 | Geddes et al. |
| 5,928,272 A | 7/1999 | Adkins et al. |
| 5,995,868 A | 11/1999 | Osorio et al. |
| 6,018,682 A | 1/2000 | Rise |
| 6,104,956 A | 8/2000 | Naritoku et al. |
| 6,264,614 B1 | 7/2001 | Albert et al. |
| 6,304,775 B1 | 10/2001 | Iasemidis et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,358,203 B2 | 3/2002 | Bardy |
| 6,366,813 B1 | 4/2002 | DiLorenzo |
| 6,473,644 B1 | 10/2002 | Terry, Jr. et al. |
| 6,477,418 B2 | 11/2002 | Plicchi et al. |
| 6,484,132 B1 | 11/2002 | Hively et al. |
| 6,497,655 B1 | 12/2002 | Linberg et al. |
| 6,549,804 B1 | 4/2003 | Osorio et al. |
| 6,556,868 B2 | 4/2003 | Naritoku et al. |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,609,025 B2 | 8/2003 | Barrett et al. |
| 6,610,713 B2 | 8/2003 | Tracey |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,656,125 B2 | 12/2003 | Misczynski et al. |
| 6,671,555 B2 | 12/2003 | Gielen et al. |
| 6,671,556 B2 | 12/2003 | Osorio et al. |
| 6,721,603 B2 | 4/2004 | Zabara et al. |
| 6,731,979 B2 | 5/2004 | MacDonald |
| 6,768,969 B1 | 7/2004 | Nikitin et al. |
| 6,793,670 B2 | 9/2004 | Osorio et al. |
| 6,819,956 B2 | 11/2004 | DiLorenzo |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,944,501 B1 | 9/2005 | Pless |
| 6,959,215 B2 | 10/2005 | Gliner et al. |
| 6,961,618 B2 | 11/2005 | Osorio et al. |
| 6,976,958 B2 | 12/2005 | Quy |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,043,305 B2 | 5/2006 | KenKnight et al. |
| 7,047,074 B2 | 5/2006 | Connelly et al. |
| 7,054,686 B2 | 5/2006 | MacDonald |
| 7,054,792 B2 | 5/2006 | Frei et al. |
| 7,079,977 B2 | 7/2006 | Osorio et al. |
| 7,089,059 B1 | 8/2006 | Pless |
| 7,139,677 B2 | 11/2006 | Hively et al. |
| 7,146,211 B2 | 12/2006 | Frei et al. |
| 7,146,217 B2 | 12/2006 | Firlik et al. |
| 7,149,572 B2 | 12/2006 | Frei et al. |
| 7,156,808 B2 | 1/2007 | Quy |
| 7,156,809 B2 | 1/2007 | Quy |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,221,981 B2 | 5/2007 | Gliner |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,321,837 B2 | 1/2008 | Osorio et al. |
| 7,324,851 B1 | 1/2008 | DiLorenzo |
| 7,346,391 B1 | 3/2008 | Osorio et al. |
| 7,353,064 B2 | 4/2008 | Gliner et al. |
| 7,373,199 B2 | 5/2008 | Sackellares et al. |
| 7,389,144 B1 | 6/2008 | Osorio et al. |
| 7,395,216 B2 | 7/2008 | Rosenfeld et al. |
| 7,401,008 B2 | 7/2008 | Frei et al. |
| 7,403,820 B2 | 7/2008 | DiLorenzo |
| 7,433,732 B1 | 10/2008 | Carney et al. |
| 7,437,196 B2 | 10/2008 | Wyler et al. |
| 7,483,747 B2 | 1/2009 | Gliner et al. |
| 7,761,145 B2 * | 7/2010 | Virag et al. .................. 600/544 |
| 2002/0072782 A1 | 6/2002 | Osorio et al. |
| 2002/0082480 A1 | 6/2002 | Riff et al. |
| 2002/0099417 A1 | 7/2002 | Naritoku et al. |
| 2002/0188214 A1 | 12/2002 | Misczynski et al. |
| 2003/0083716 A1 | 5/2003 | Nicolelis et al. |
| 2004/0006278 A1 | 1/2004 | Webb et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0199212 A1 | 10/2004 | Fischell et al. |
| 2005/0021103 A1 | 1/2005 | DiLorenzo |
| 2005/0021104 A1 | 1/2005 | DiLorenzo |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0177200 A1 | 8/2005 | George et al. |
| 2005/0182389 A1 | 8/2005 | LaPorte et al. |
| 2005/0187796 A1 | 8/2005 | Rosenfeld et al. |
| 2005/0197590 A1 | 9/2005 | Osorio et al. |
| 2006/0111644 A1 | 5/2006 | Guttag et al. |
| 2006/0122525 A1 | 6/2006 | Shusterman |
| 2006/0122864 A1 | 6/2006 | Gottesman et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0195163 A1 | 8/2006 | KenKnight et al. |
| 2006/0224067 A1 | 10/2006 | Giftakis et al. |

(56) References Cited

U.S. PATENT DOCUMENTS

| | | |
|---|---|---|
| 2006/0224191 A1 | 10/2006 | DiLorenzo |
| 2006/0293720 A1 | 12/2006 | DiLorenzo |
| 2007/0027486 A1 | 2/2007 | Armstrong et al. |
| 2007/0027497 A1 | 2/2007 | Parnis |
| 2007/0027498 A1 | 2/2007 | Maschino et al. |
| 2007/0027500 A1 | 2/2007 | Maschino et al. |
| 2007/0032734 A1 | 2/2007 | Najafi et al. |
| 2007/0073150 A1 | 3/2007 | Gopalsami et al. |
| 2007/0073355 A1 | 3/2007 | DiLorenzo |
| 2007/0088404 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0149952 A1 | 6/2007 | Bland et al. |
| 2007/0150024 A1 | 6/2007 | Leyde et al. |
| 2007/0150025 A1 | 6/2007 | Dilorenzo et al. |
| 2007/0156450 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173902 A1 | 7/2007 | Maschino et al. |
| 2007/0179557 A1 | 8/2007 | Maschino et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0244407 A1 | 10/2007 | Osorio |
| 2007/0282177 A1 | 12/2007 | Pilz |
| 2007/0287931 A1 | 12/2007 | DiLorenzo |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033508 A1 | 2/2008 | Frei et al. |
| 2008/0064934 A1 | 3/2008 | Frei et al. |
| 2008/0077028 A1 | 3/2008 | Schaldach et al. |
| 2008/0114417 A1 | 5/2008 | Leyde |
| 2008/0119900 A1 | 5/2008 | DiLorenzo |
| 2008/0146890 A1 | 6/2008 | LeBoeuf et al. |
| 2008/0161712 A1 | 7/2008 | Leyde |
| 2008/0161713 A1 | 7/2008 | Leyde et al. |
| 2008/0183096 A1 | 7/2008 | Snyder et al. |
| 2008/0183097 A1 | 7/2008 | Leyde et al. |
| 2008/0208074 A1 | 8/2008 | Snyder et al. |
| 2008/0208781 A1 | 8/2008 | Snyder |
| 2008/0234598 A1 | 9/2008 | Snyder et al. |
| 2008/0255582 A1 | 10/2008 | Harris |
| 2009/0054795 A1 | 2/2009 | Misczynski et al. |
| 2010/0274303 A1 | 10/2010 | Bukhman |
| 2011/0251468 A1 * | 10/2011 | Osorio .......................... 600/300 |

FOREIGN PATENT DOCUMENTS

| | | |
|---|---|---|
| WO | WO 9302744 | 2/1993 |
| WO | WO 0064336 C2 | 11/2000 |
| WO | WO 2004036377 | 4/2004 |
| WO | WO 2005067599 | 7/2005 |
| WO | WO 2006050144 | 5/2006 |
| WO | WO 2006122148 | 11/2006 |
| WO | WO 2007066343 A2 | 6/2007 |
| WO | WO 2007142523 | 12/2007 |
| WO | WO 2008054580 | 5/2008 |

OTHER PUBLICATIONS

PCT Search Report and Written Opinion for International Application No. PCT/US2012/027639, dated Oct. 4, 2012, 22 pages.

Kautzner, Josef et al., Utility Of Short-Term Heart Rate Variability For Prediction Of Sudden Cardiac Death After Acute Myocardial Infraction, Acta Univ., Palacki. Olomuc., Fac. Med., vol. 141, 1998, pp. 69-73.

* cited by examiner

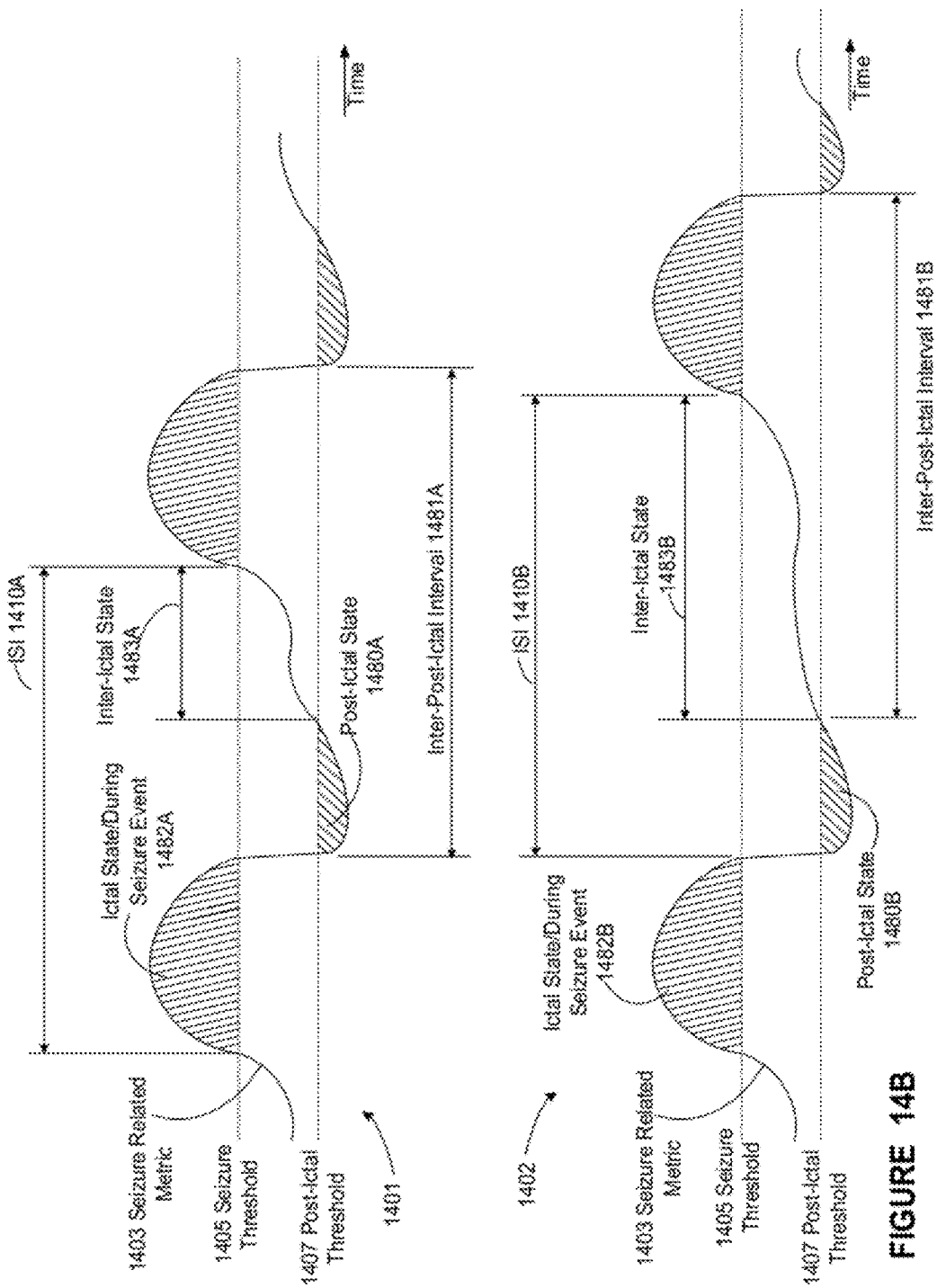

(Example of Non-Status)

(Example of Status)

DETECTING, ASSESSING AND MANAGING EXTREME EPILEPTIC EVENTS

BACKGROUND

1. Field of the Invention

This invention relates generally to medical device systems and, more particularly, to medical device systems and methods capable of assessing and managing extreme events related to epilepsy.

2. Description of the Related Art

Generalized tonic-clonic status epilepticus, referred to herein as Convulsive Status Epilepticus (CSE) is a neurological emergency with an estimated incidence of about 20 out of 100,000 patients and is generally considered an extreme event. CSE is also associated with a mortality rate between 3% and 40% depending on etiology, age, status type, and status duration. CSE, in particular, requires immediate, aggressive, and effective treatment to stop seizure activity, to prevent neuronal damage, systemic complications and the possibility of death. Most investigations on prognosis of status epilepticus (SE) have focused on mortality, and some research suggests that outcome basically depends on the etiological and biological background but also that the earlier the therapeutic intervention the higher the probability of controlling it. Additionally, non-convulsive status epilepticus (nCSE), while not a medical emergency of the magnitude of CSE, it is also an extreme event as nevertheless it increases the risk of bodily injury and neurologic deficits such as permanent potentially severe impairment in memory.

CSE and nCSE are defined based on the duration of a single seizure and its variations or on the lack of recovery of certain neurologic functions to their inter-ictal (baseline) levels in the context of closely spaced seizures. The focus on seizure duration or frequency or on level of consciousness or of awareness to determine if a patient is in status epilepticus has important limitations, since signals or indices from others systems such as cardio-vascular, respiratory, endocrine and metabolic which are also adversely impacted by the seizures and which directly contribute to the increased (compared to the non-epileptic population) morbidity and mortality of patients with epilepsy are disregarded. The state of the art views and treats Status Epilepticus narrowly and ineffectively. Embodiments of this invention takes a system's approach by quantifying the impact of seizures on bodily functions (e.g., neurologic, cardiovascular) to determine the probability they are harbinger of extreme events (e.g., status epilepticus) and to prevent them from occurring, or if they are extreme, to provide early treatment and/or warning to avert serious neurological and medical sequelae or even fatal outcomes.

Sudden Unexpected Death in Epilepsy, or "SUDEP," another extreme event, is a phenomenon in which a patent with epilepsy dies unexpectedly and without an apparent, outstanding cause, that is, the death is unexplained since autopsy results are unrevealing. One of the main risk factors for SUDEP is the lack of seizure control with first line drugs prescribed alone or in any safe combination and dosage. Whether or not the first in a chain of ultimately fatal events leading to SUDEP is a seizure, the defining event is likely to be either cardiac (e.g., ventricular fibrillation or asystole) or respiratory (e.g., apnea) or both. Currently, the monitoring, detection, prediction and prevention of SUDEP are underdeveloped and markedly limited in breadth and depth of scope, limitations which embodiments of this invention address.

CSE and nCSE alter autonomic nervous system function and SUDEP may be caused by autonomic dysfunction. Since brain/neurological activity such as electrical activity, whether normal or abnormal, and autonomic functions (e.g., cardiovascular activity, respiration, etc.), referred to herein as body signals (from which body data may be derived), are functionally tightly coupled; monitoring these body signal provides valuable information. This is the first invention to utilize not only neurologic, autonomic, metabolic, endocrine and tissue stress marker signals but do so in a multi-variant adaptive manner to optimize sensitivity and specificity of detection of extreme epileptic events (e.g., CSE, SUDEP), and, more importantly to anticipate them.

SUMMARY OF EMBODIMENTS

In one aspect of the present invention, a method for identifying an extreme seizure event in a patient is provided. The method calls for determining at least one of an autonomic index, a neurologic index, a metabolic index, an endocrine index, or a tissue stress index, the at least one determined index being based upon body data. The method further calls for identifying a seizure event based upon the at least one determined index and determining at least one seizure severity index (SSI) value indicative of the severity of the seizure event. The method further calls for comparing the determined at least one SSI value to at least one reference value and identifying an occurrence of an extreme seizure event, based upon the comparison of the determined SSI value to the at least one reference value.

In another aspect of the present invention, an apparatus is provided. The apparatus includes a determination component adapted to determine at least one of an autonomic index, a neurologic index, a metabolic index, an endocrine index, or a tissue stress index, the at least one determined index being based upon body data and identify a seizure event based upon the at least one determined index. The determination component is further adapted to determine a seizure severity index (SSI) value indicative of the severity of the seizure event, compare the determined SSI value to at least one reference value, and identify an occurrence of an extreme epileptic event, based upon the comparison of the determined SSI value to the at least one reference value.

In yet another aspect of the instant invention, a non-transitive, computer-readable storage device for storing instructions that, when executed by a processor, perform a method for identifying an extreme seizure event in a patient is provided. The method comprises determining at least one of an autonomic index, a neurologic index, a metabolic index, an endocrine index, or a tissue stress index, the at least one determined index being based upon body data. The method further comprises identifying a seizure event based upon the at least one determined index and determining at least one seizure severity index (SSI) value indicative of the severity of the seizure event. The method also includes comparing the determined at least one SSI value to at least one reference value and identifying an occurrence of an extreme seizure event, based upon the comparison of the determined SSI value to the at least one reference value.

In yet another aspect of the instant invention, a method for identifying an extreme seizure event in a patient is provided. The method comprises determining at least one of an autonomic index, a neurologic index, a metabolic index, an endocrine index, or a tissue stress index, the indices being based upon body data. The method also comprises identifying at least two seizure events based upon the at least one determined index and determining at least one seizure severity index (SSI) value related to at least one of the at least two seizure events. The method further comprises determining at least one inter-seizure interval (ISI) value related to the at least two seizure events and identifying an occurrence of a state of status epilepticus in the patient, based upon the determined SSI value and the determined ISI value.

BRIEF DESCRIPTION OF THE DRAWINGS

The present invention may be understood by reference to the following description taken in conjunction with the accompanying drawings, in which like reference numerals identify like elements, and in which:

FIG. 14B provides a graphical depiction of ictal, inter-ictal/inter-seizure, post-ictal and inter-ictal periods, in accordance with one illustrative embodiment;

Figure 1A:
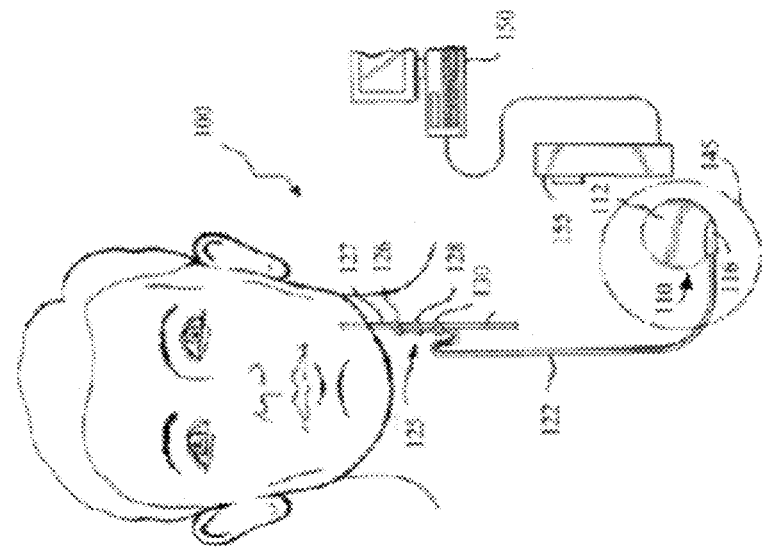
FIG. 1A provides a stylized diagram of a medical device which may be implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated. The terms "adapted to" and "capable of" as used herein may imply, among other things, that a device has a structure sufficient to perform some task or operation. The terms "adapted to" and "capable of" are not used to state (implicitly or explicitly) mere intended use limitations in the description and claims of the instant Application.

The term "electrode" or "electrodes" described herein may refer to one or more stimulation electrodes (i.e., electrodes for delivering a therapeutic signal generated by an MD to a tissue), sensing electrodes (i.e., electrodes for sensing a physiological indication of a patient's body), and/or electrodes that are capable of delivering a therapeutic signal, as well as performing a sensing function.

The terms "specific care" described herein may be care provided to a patient that is targeted at a seizure event itself such as electrical stimulation, anti-seizure drug treatments, and the like. The term "supportive care" described herein is care targeted to maintain vital functions within the normal range and minimizing the risk of tissue damage through body/brain cooling, administration of medications with antioxidant properties and/or the like.

The term "occurrence" used in reference to epileptic events may mean a risk of occurrence, an increased/increasing risk of occurrence, or an actual occurrence of such events. The terms "seizure event" and "epileptic event" may be used interchangeably.

The terms "microscopic," "mesoscopic," and "macroscopic" described herein may show time periods which may be used in observation of seizure events and/or extreme seizure events, body changes such as heart wave and heart wave complex morphology, heart rate variability, and/or other body data described herein. "Microscopic" may correspond to the scale of observation of at least part of a heart beat such as that represented by an EKG's P-QRS-T complex or may correspond to a period of time that is less than a "mesoscopic" time period (e.g., less than 10 seconds). "Mesoscopic" may correspond to a scale of observation of several seconds to tens of seconds (e.g., 10-300 seconds) to capture at least in part, a change in the shape of heart rate plot representative of a state change. "Macroscopic" may correspond to an scale of observation longer than 300 seconds that may be used to encompass more than the information contained in the "mesoscopic" scale or window as described above. In the context of the description provided herein, the term "window" may be used to refer to one or more of the "mesoscopic," "microscopic" and "macroscopic" time periods described above.

A patient may have certain kinds of seizures which may be classified as "extreme" As defined herein, extreme seizures are classified based on: a) certain metrics such as a seizure severity index (SSI), inter-seizure interval (ISI), post-ictal severity index (PISI) and/or b) the impact the seizures have on a subject, which in some embodiments may be determined using the metrics listed herein (see, e.g., a) above), and in other embodiments may be influenced by additional measures, such as the effects of a fall or other injuries associated with a particular seizure event.

Seizure metrics may include energy, defined for example as the product of peak intensity and duration, or as the product of the logarithm of the standard deviation of the difference of signals (e.g., EKG) and the duration. If $Z(t)$ is the reference EKG signal then its difference from a test epoch will be $X(t)=Z(t)-Z(t-1)$.

These seizure metrics may be derived not only from cortical electrical activity, to date the only signal used for this purpose, but from kinetic (e.g., movement, acceleration or force of the body or body parts), cognitive (e.g., awareness, memory), cardiac (e.g., heart rate or heart rate variability), respiratory (e.g., rate, tidal volume, oxygen saturation), metabolic (e.g., pH), tissue stress markers (e.g., lactic acid) or endocrine activity (e.g., cortisol) which provide valuable and reliable information about seizures such that they may be used in lieu of or in addition to electrical cortical activity. For example, the product of peak heart rate and the time it spends above values not observed during seizures may be used to estimate seizure severity.

Severity may also be a seizure metric from which a seizure severity index (SSI) may be determined. The SSI may be observable/measurable data associated with a seizure that is quantifiable. Severity may be defined for example as the average of the sum of percentile intensity, duration and extent of spread of changes caused in the brain and other body organs, or as the sum of energies at each brain site engaged in seizure activity or at each organ affected by said seizure activity. In some embodiments, the SSI may be determined based upon one or more of the duration of the seizure event, the peak intensity of the seizure event and the spread of the seizure event. In some embodiments, the SSI may be determined based upon the duration of the seizure event and the peak intensity of the seizure event. In some such embodiments, the SSI may be calculated as the product of the peak intensity of the seizure event and the duration of the seizure event. The peak intensity may be the maximum value of any one, or any number, of body data values during a seizure event. For example, heart rate, an autonomic index, may be used to compute an SSI as follows: a) If a patient's mean inter-ictal (in-between seizures) heart rate is 80 beats/minute, the peak ictal heart rate is 150 beats/minute and the increase in heart rate above inter-ictal values lasts for 40 seconds, the SSI is either 6000 if the peak heart rate is used or 2800 if instead the net increase is taken into account. The "area under the curve" may be also utilized to compute the SSI; b) If a patient's mean inter-ictal oxygen saturation during wakefulness is 93% and during a convulsion it drops to a minimum of 60%, remaining below the inter-ictal baseline for 60 seconds, the SSI based on this index, is 60×60=3600, or 33×60=1980 if instead the net decrease is used. In this example, an SSI above a pre-determined (or adjustable) value may indicate a risk of an extreme epileptic event/state (e.g., status epilepticus). Similarly, an SSI value above or below a pre-determined (or adjustable) percentile based upon historical patient data may indicate an increased risk of occurrence of an extreme event. For example, if an SSI value for a patient is above the ninetieth percentile of the patient's past SSI values, the patient may be at an increased risk for being in an extreme epileptic state (e.g., status epilepticus).

In one embodiment, an SSI value indicative of the severity of a seizure may be determined based upon a body data as described above. In one embodiment, the determined SSI value may be compared to one or more of a reference value or an extreme reference value that may or may not include a status epilepticus value. The status epilepticus value(s) may be based upon at least one of a past SSI value, a mean SSI value, a median SSI value, a mode SSI value, a percentile SSI value, a normalized SSI value, a distribution of SSI values, or to any other statistical transformation of an SE index or observable SE index change. Another useful measure for seizure time series is a post-ictal severity index (PISI) which may be defined as the intensity, duration and/or extent of spread (and changes therein) during the post-ictal state, compared to the inter-ictal or to the ictal state.

Inter-seizure interval (ISI) may also be a seizure metric, and may be defined as the time (in any unit of time) elapsed between the onset of consecutive or non-consecutive seizures, or between the end of a seizure and the start of the next one. In one embodiment, inter-seizure intervals (ISIs) indicative of the time elapsed for example, between the end time and onset time of seizures, may be determined based at least upon body data and by performing statistical analyses to obtain measures of central tendency (e.g., mean) after appropriate statistical transformations if indicated, distributions either temporal, spatial or both, and the like. It should be noted that depending upon how the ISI is defined, seizure activity may be contained within this interval. Specifically, if the ISI is defined as the time from the onset of a seizure to the onset of the next seizure, seizure activity is contained therein (see, e.g., inter-seizure intervals 1790, 1796 and 1798 of FIG. 17A below; each contain seizure activity). The determined ISI value(s) may be compared to reference/extreme reference value(s) that may or may not include a status epilepticus value. The status epilepticus value(s) may be based upon at least one determining if a status epilepticus event is occurring or the probability that it may occur. The ISI values may be obtained from any potential or known epileptogenic brain site. Additionally, the various inter-seizure intervals described above may be classified as extreme seizure intervals (ESIs). For example, if a patient is at risk/increased risk for, or is in, an extreme event state (e.g., status epilepticus or some other extreme seizure state), the seizure intervals described above may be classified as ESIs. Similarly, if an ESI is detected/determined, such a detection/determination may be indicative of a patient's risk/increased risk for an extreme epilepticus event/state and/or the patient having an extreme epileptic event, such as, but not limited to, status epilepticus.

Similarly, a seizure event time series may be used to label and/or classify multiple seizure events and/or their respective severities. A seizure event time series may be a function of data related to a seizure event and an inter-seizure interval. Such a time series may be represented as:

$$sz_{time\ series} = f(SSI, ISI, Spread).$$

An overall index for a time series of seizure events ($SS_{time\ series}$) may be determined, in some embodiments, as:

$$SS_{time\ series} = sz_{time\ series,I}, ISI$$

where I may denote at least any given sz as being one or more of any of the seizure events described above as sz==f (intensity, duration, spread)/3), sz=(body data), sz=(any seizure data), (where seizure data is, e.g., as described with respect to FIG. 5A), and/or the like and ISI is at least one of an interval associated with said seizure.

Seizure spread may also be a seizure metric. Embodiments described herein introduce and apply the metric "seizure spread" using a new scale incorporating one or more body organ/systems in addition to the brain. Conventionally, seizure spread has been limited to electrical activity as recorded with electrodes placed over a certain brain/cortical area or volume; spread is measured by determining the fraction of electrodes involved by seizure activity as a function of the total number of electrodes (e.g., 15/20 means that the seizure spread to 15 of 20 available electrodes). In one embodiment of this invention, the number of body organs/systems or parts affected by seizure activity is determined by measuring their respective indices (e.g., kinetic and/or responsiveness for neurologic, heart rate and/or EKG morphology for cardiac/autonomic, prolactin and/or cortisol for endocrine, or others). The body seizure spread is given by the number of organs/system affected (OA), multiplied by the total number of organs/systems tested (OT) divided by the total number of organs tested [BS=OA×OT/OT] or as the fraction of organs affected divided by the total number of organ tested [BS=OA/OT].

In one embodiment of this invention there are six testable organs/systems (autonomic, neurologic, endocrine, metabolic, tissues stress markers and quality of life) and each of these has several testable indices (vide infra). This plurality of indices may be exploited to derive a novel and useful composite measure, the Body Intensity-Spread ($B_{i-s}$). If in one embodiment of this invention more than one organ/system index (e.g., for autonomic/cardiac: heart rate and heart rate variability; for neurologic: kinetic and responsiveness/awareness; for endocrine: cortisol and prolactin, and/or others), are tested, a Body Intensity-Spread ($B_{i-s}$) is created. This measure which may be applied to at least one of each organ/system is given by the product of the number of affected indices ($I_a$) in each organ/system multiplied by the number of tested indices ($I_t$) divided by the total number of tested indices ($I_t$) plus the product of indices tested ($I_t$) and total testable indices ($I_{te}$) divided by total testable indices ($I_{te}$) plus the product of affected organs ($O_a$) and tested organs ($O_t$) divided by tested organs ($O_t$) plus the product of the number of tested organs ($O_t$) and testable organs ($O_{te}$) divided by the total testable organs ($O_{te}$) [$B_{i-s}=(I_a \times I_t/I_t + I_t \times I_{te}/I_{te} + O_a \times O_t/O_t + O_t \times O_{te}/O_{te})$]. By way of example: a) If two indices are tested, only one is affected, there are four testable indices, two organs were tested and one was affected and there are six testable organ, then, $B_{i-s}=1 \times 2/2 + 2 \times 4/4 + 2 \times 4/4 + 2 \times 6/6 = 1+2+2+2=7$; b) If two indices are tested, both are affected, there are four testable indices, four organs were tested, two were affected and there are six testable organs, then, $B_{i-s}=2 \times 2/2 + 2 \times 4/4 + 2 \times 4/4 + 4 \times 6/6 = 2+2+2+4=10$; c) If two indices are tested, both are affected, there are four testable indices, four organs were tested and all were affected, and there are six testable organs, then, $B_{i-s}=2 \times 2/2 + 2 \times 4/4 + 4 \times 4/4 + 4 \times 6/6 = 2+2+4+4=12$; d) If two indices are tested, both are affected, there are six testable indices, four organs were tested, all were affected and there are six testable organs, then, $B_{i-s}=2\times2/2+2\times6/6+4\times4/4+4\times6/6=2+2+4+4=12$. If $B_{i-s}$ is multiplied by the sum of the duration of changes for each index and for each organ the result is a generalized comprehensive seizure severity index ($SSI_g$).

Another novel metric, the Corrected Body Intensity-Spread ($CB_{i-s}$) takes into account differences in the ratio of tested/testable indices and/organs to provide more precise insight into the severity and/or impact of seizure events on patients. The ($B_{i-s}$) as computed in the paragraph above may have equal values yet the ratio of tested/testable indices may be different. The interpretation of two ($B_{i-s}$) of equal value must be different if for example the number of indices tested ($I_t$) is the same but the number of testable indices ($I_{te}$) is not. In order to provide a more pathophysiologically meaningful measure, it is necessary to correct for differences in said ratio, which may not be reflected in the total $CB_{i-s}$ values. To this end, the simple ratios may be computed [$CB_{i-s}=(I_d/I_t+I_t/I_{te}+O_d/O_t+O_t/O_{te})$]. This correction may be also applied to organs/systems. Those skilled in the art having the benefit of this disclosure will realize that methods other than those used herein may be used for computing $CB_{i-s}$.

In a systems approach to epilepsy disease state, a useful metric may be physical fitness and/or physical integrity. Physical fitness/integrity is one of several suitable measures of patient seizure impact (PSimp). For example, if a patient suffers a leg fracture during a seizure, the level of fitness/integrity will likely decrease (at least temporarily) thereafter, compared to a baseline value obtained when the patient had no injuries. Physical fitness/integrity data may be collected and used to determine an amount of physical activity the patient may perform and the sense of well being (e.g., via QOL questionnaires). A physical fitness/integrity index may then be determined based upon the fitness/integrity data. The physical fitness/integrity index may, in some embodiments, be representative of the current physical fitness/integrity of the patient relative to past, normative and/or expected physical fitness/integrity. The physical fitness/integrity index may be ranked based upon the collected body data information, external indications, seizure data, a patient's past physical fitness/integrity data, normative physical fitness/integrity data, expected physical fitness/integrity data and/or other data that would become apparent to one of skill in the art having the benefit of this disclosure. Additionally, the physical fitness/integrity index may be based upon a comparison of any or all of the above referenced data, information or indications. It is noted that physical fitness/integrity data may be acquired from a source external to the patient's body or the patient's medical device (e.g., a physician), where the external source may provides data that may not be directly obtainable using a patient's medical device (e.g., right femur fracture on a certain date, length of disability, etc).

The seizure impact on a patient may be captured with two measures: 1. Patient Seizure Impact (PSimp), which takes into account adverse effects in organ/systems associated with, or attributable to, a seizure, and which are short-lived (e.g., minutes) and fully reversible; and 2. Patient Seizure Burden (PSB) which takes into account: i) adverse effects on organs/systems which are either reversible but longed lived (e.g., hours to months) or irreversible; and ii) Quality of Life (QOL). In one or more embodiments, PSimp and/or PSB may reflect SSI and ISI values, while in other embodiments, PSimp and/or PSB may not reflect SSI and ISI values. PSimp may be determined qualitatively or quantitatively using any index from any organ/system in any possible number or combinations. For example, the most recent seizure was associated with transient S-T segment elevation (qualitative) or the most recent seizure was associated with S-T segment elevation of 1 mm which lasted for 30 minutes (quantitative). The following example puts into perspective the usefulness of the PSimp: Two seizures with identical severity (SSI) may have a different impact on a patient: the outcome of convulsions which are associated with generalized loss of postural tone (which explains the falls to the ground) is different if they occur while the subject is in an upright as opposed to a recumbent position. The fall in the upright patient may result in scalp laceration, a reversible injury, while a convulsion with the same severity index value will not have these consequences if it occurs when the patient is lying down in bed. Seizure impact may be determined using neurologic, autonomic, tissue stress markers, endocrine, metabolic, psychologic/psychiatric (quality of life questionnaires) and musculo-skeletal signals.

Seizure burden (PSB) may be also determined qualitatively or quantitatively by using one or more of the following in one or more combinations: Deterioration in any organ/system as measured using indices. For example, a patient's IQ may drop from 105 to 92 over a 1 year period as a consequence of seizures, or heart rate variability (which is associated with an increase risk for sudden death) has significantly decreased over the last 6 months. Another example puts into perspective the usefulness of the PSB: Consider the example above of two convulsions with identical severity but during one the patient is lying down and during the other walking down stairs. The convulsion in the patient walking downstairs caused that resulted in skull fracture and a cerebral hematoma that left the patient with right hemiparesis. The PSB of the convulsion that occur with the patient in bed is "zero" while the PSB of the patient in the stairs was large as it caused irreversible brain damage.

A global seizure burden (GSB) may be determined/calculated based upon a summation of one or more seizure burdens of different factors/indices:

$$GSB=PSB(neurologic)+PSB(autonomic)+PSB(metabolic)+PSB(endocrine)+PSB(tissue\ stress\ markers)+PSB(QOL)+PSB(other\ factors).$$

PSimp and/or PSB may be scalar-valued functions of one or more body data variables that simplifies a possibly complex set of body information down to a single number (PSimp) or simply a qualitative statement (e.g., mild, moderate or severe injury). For the purposes of this disclosure, the terms "patient impact", "seizure impact", and "patient seizure impact" may be used interchangeably and referred to as "PSimp". In accordance with one embodiment, the PSimp may be any statistic (or scalar-valued function) that reflect some aspect of the impact of the corresponding seizures on the patient and may be ordered/sorted so that the distance differences between the PSimp values for different seizures can be measured, compared and/or interpreted to provide meaningful information.

A seizure may be considered extreme (independent of its SSI or ISI or spread values), if it causes system dysfunction of a type, magnitude, duration and/or frequency exceeding the ictal or post-ictal baseline dysfunction for that subject, or if the seizure adversely affects the subject's physical (including the neurologic system) integrity.

The concept of "extreme" may take different meanings for different fields. Extreme value theory in math is a specific corpus in which limit theorems have been developed for the extreme of maximum value of a set of N variables. The term "extreme" as used herein may or may not have this mathematical connotation.

Classifying a seizure event as "extreme" may be based upon a deleterious impact upon (or seriousness in relation to) the patient's health (e.g., falls, bone fractures, cardiac and/or respiratory dysfunction, memory loss, etc), and well being (e.g., depression) or the condition of the patient's disease state (e.g., worsening of epilepsy). In different cases, extreme seizure events may be classified according to other standards as well, and need not necessarily be specifically limited to those described herein. Similarly, extreme seizure events may be a combination of the above described classifications. An extreme seizure state may result in coma, cardio-respiratory failure, metabolic acidosis, liver and/or renal failure, bed sores, bone fractures, tissue hypoxia and brain damage. In one embodiment, an extreme epileptic state is defined as two or more extreme events occurring in close temporal proximity to each other.

Certain mathematical functions may be used to determine if an event, in this case, a seizure is extreme or not. In humans with pharmaco-resistant seizures at least under certain conditions, the probability density functions of energy and inter-seizure intervals of seizures originating from discrete brain regions may be partly described by power laws. The probability density function of seizure energy (see, e.g., FIGS. 13-14), a power law, differs from a Gaussian or normal probability density function in its skewness (to the right with respect to the mean), reflecting the presence of events with very large ("extreme") energy. For example, if seizure energy or severity is above two standard deviations from the mean (calculated from a normalized distribution), this seizure may be considered as an extreme seizure event including but not limited to, status epilepticus, a risk of status epilepticus, an increased risk of status epilepticus, a risk of SUDEP, an increased risk of SUDEP and/or the like. Inter-seizure intervals with duration below two standard deviations to the left of the mean calculated from a normalized distribution may be indicative of an extreme epileptic event/state including but not limited to status epilepticus, a risk status epilepticus, an increased risk of status epilepticus, a risk of SUDEP, an increased risk of SUDEP and/or the like. Alternatively, an extreme event may correspond to an event with severity as measured by any body data value at or below the $10^{th}$ percentile, or at or above the $90^{th}$ percentile of values, for the time of day (to account for circadian variability), state (e.g., wakefulness versus sleep) or level of physical activity (moving about versus resting). Other values for classification of events may be chosen as needed to improve performance. It should be noted, however, that in one or more embodiments no formal statistical analysis needs to be made to determine if an extreme event(s) is about to occur, is occurring or has occurred.

Those skilled in the art having the benefit of this disclosure will appreciate that non-Gaussian distributions may be normalized by, for example, applying to the data logarithmic transformations so that mean, standard deviation and other measures may be more easily estimated. The approach of treating certain seizures as extreme events lends itself to a statistical or probabilistic approach for the prevention of status epilepticus through their anticipation or early detection.

The following "metrics" expressed as indices, alone or in any combination, may be used to classify seizures into extreme as compared to non-extreme:
1. Magnitude and/or rate of increase in seizure energy or intensity, duration or extent of spread (referred to herein as the seizure severity index (SSI)). The SSI may be derived from one or more of these three metrics in any combination and using a useful mathematical approach. For example, the SSI may correspond to the area under the curve of the seizure plot); 2. Magnitude and/or rate and/or duration of increase/decrease and of extent of spread, changes in body indices (e.g., heart activity, arterial pH and others) after the end of a seizure compared to inter-ictal or ictal values, referred herein to as a post-ictal severity index (PISI); 3. Magnitude and/or rate and/or extent of recovery from the post-ictal to the inter-ictal state of any body index; 4. Inter-seizure interval duration including the conditional probability of time to the next seizure given the time elapsed since the last seizure; 5. Seizure frequency per unit time, and/or cumulative seizure severity index (SSI) per unit time; 6. Cumulative post-ictal severity index per unit time compared to inter-ictal or ictal index values 7. Magnitude and/or duration and rate of change in level of consciousness as measured using available coma scales such the Glasgow scale or qualitative classification (e.g., deep coma, superficial coma, stupor, lethargy, awake but confused) as also used in clinical practice, compared to a baseline consciousness level; 8. Magnitude, duration (when applicable, e.g., when the patient is awake) and/or rate of changes in one or more cognitive functions as measured, for example, using a reaction time or any other validated neuropsychologic test; 9. Magnitude and/or duration and/or extent of spread in brain energy (electrical or metabolic, as measured using appropriate tools; 10. Magnitude, duration and/or rate of changes in autonomic indices such as heart rate, heart rate variability, heart rhythm, EKG, blood pressure, respirations, catecholamines, temperature and/or galvanic skin resistance, among others; 11. Magnitude, duration and/or rate of changes in metabolic indices such as arterial pH, $SaO_2$, $CO_2$, glucose and/or electrolytes, among others; 12. Magnitude, duration and/or rate of changes in endocrine indices such prolactin, cortisol, and/or growth hormone among others; and 13. Magnitude, duration and/or rate of change in tissue stress markers such as Reactive oxygen and nitrogen species including but not limited to iso- and neuro-prostanes and nitrite/nitrate ratio, gluthatione, gluthatione disulfide and gluthatione peroxidase activity, citrulline, protein carbonyls, thiobarbituric acid, the heat shock protein family, catecholamines, lactic acid, N-acetylaspartate, when applicable, free radicals, CK, Aldolase, troponin, and/or the like or of their metabolited when applicable. Comparisons of the above listed metrics and of all the indices listed below, may be made by taking into account time of day, level of consciousness of the patient (e.g., awake or asleep), level of physical activity (e.g., resting versus moving about) at the time the measurements were made, age, gender and physical fitness/health status or physical integrity.

In one or more embodiments, index values indicative of the function the autonomic, neurologic, endocrine, metabolic, gastro-intestinal, and/or of tissue/organ stress, such as those listed below, along with processes and tools for measuring and/or deriving these signals and markers, may be used to determine the occurrence of seizure events and to classify them as either non-extreme or extreme:

I. Autonomic:
  a) Cardiac: Intra-cardiac pressure, cardiac volume, the ratio of intra-cardiac pressure to cardiac volume, ejection fraction, blood flow, cardiac wall temperature, heart rate variability (HRV), rate of change of HRV as a function of heart rate, heart sounds, heart rhythm, heartbeat wave morphology, point of maximum impulse force, thoracic wall deflection as measured with suitable tools such as EKG, phonocardiogram (PKG), Echocardiography, Apexcardiography (ApKG), and/or the like;
  b) Vascular: arterial and or venous pressure, arterial and/or venous blood wave pressure morphology, arterial and/or venous blood flow velocity, arterial and/or venous blood flow sounds, arterial and/or venous temperature as measured with suitable tools such as pressure, Doppler, sound, ultrasound and/or the like;

c) Respiratory: tidal volume, minute volume, respiratory wave morphology, respiratory sounds, intercostal electromyography (EMG), diaphragmatic EMG, at least one chest wall and/or abdominal wall motion, respiratory rate (RR), rate of change of RR, arterial gases concentrations, oxygen saturation, end-tidal $CO_2$, as measured with suitable tools;

d) Dermal: skin resistance, skin temperature, skin blood flow, sweat gland activity as measured with suitable tools;

e) Neurotransmitters: concentrations of catecholamines and/or catecholamine metabolites, acetylcholine and/or acetylcholinesterase activity in body fluids or other tissues with suitable assays; rate of change cathecholamines, acetylcholine and/or acetylcholinesterase activity as measured from body fluids or other tissues with suitable assays, II. Neurologic a) Cognitive/Behavioral: level of consciousness, level of attention, reaction time, memory, visuo-spatial, language, reasoning, judgment, calculations, auditory and/or visual discrimination as measured using validated tests;

b) Kinetic: force of muscle contraction, body movement direction, speed, acceleration, trajectory of movements in one, two and/or three dimensions, pattern and/or quality of movements, head, eyes, limb/body posture and/or position, body part orientation and/or position in reference to each other, body part orientation and/or position in reference to one or more predetermined axes or fiducials (e.g., body incline), muscle tone, agonist-to-antagonist muscle tone ratio, gait, accessory movements, falls as measured with suitable tools;

c) Vocalizations: formed and/or unformed vocalizations as measured with suitable tools;

d) Electroencephalography (EEG), Electrocorticography (ECoG), evoked potentials, field potentials, single unit activity as measured with suitable tools, III. Endocrine:

a. prolactin, luteinizing hormone, follicle stimulation hormone, growth hormone, adreno-corticotropin hormone (ACTH), cortisol, vasopressin, beta-endorphin, beta, lipotropin, corticotropin-releasing factor (CRF) as measured from body fluids or other tissues with suitable assays;

IV. Tissue Stress Markers:

a. reactive oxygen and/or nitrogen species from the list comprising iso- and neuro-prostanes and nitrite-nitrate ratio, gluthatione, gluthatione disulfide and gluthatione peroxidase activity, citrulline, protein carbonyls, thiobarbituric acid, a heat shock protein family, catecholamines, lactic acid, N-acetylaspartate, metabolites of citrulline, protein carbonyls, thiobarbituric acid, a heat shock protein family, chromogranin A, free radicals or reactive oxygen species, catecholamines, lactic acid or N-acetylaspartate; as measured from body fluids or other tissues with suitable assays, V. Metabolic:

a. arterial pH, arterial gases, lactate/pyruvate ratio, electrolytes and glucose as measured from body fluids or other tissues with suitable assays.

The increased probability of subclinical and clinical pharmaco-resistant seizures to occur in clusters (see FIG. 15), an observation previously made for clinical seizures only, and the decreased probability of seizure occurrence with increasing time from the last one (see e.g., FIG. 17B) may be interpreted as: (i) reflecting the inherent capacity of seizures to trigger seizures; (ii) indicative of some form of seizure interdependency or plasticity ('memory') in the system, as recently proposed; and/or (iii) a clinically useful observation that in the embodiments herein may be exploited to anticipate and prevent extreme epileptic events including but not limited to status epilepticus.

In one more embodiments, the method comprises either anticipating and preventing or identifying and/or managing an occurrence of an extreme epileptic event/state both with a certain probability, based upon a comparison of the determined SSI value to a reference or upon models based among other factors on the temporal evolution of SSI, patient seizure impact (PSimp) or ISI values or both. In one embodiment, the impact of the seizure is measured not only on each of the organ/systems of the body, but on the entire body as well.

Although not so limited, methods and apparatus capable of implementing embodiments of the present invention are described below. In the context of this description, a medical device (MD) or medical system may also be referred to as an implantable medical device and/or an implantable medical device/system (IMD). It is contemplated that such a device and/or system may be implantable or non-implantable/non-implanted in various embodiments without departing from the spirit and scope of the invention. That is, when an implantable medical device/system (IMD) is described in one or more embodiments, it is also contemplated that a corresponding non-implanted or non-implantable may be used in one or more alternate embodiments and vice versa. In other embodiments, some portions of the system may be implanted while other portions may be external to the patient's body.

Figure 1B:
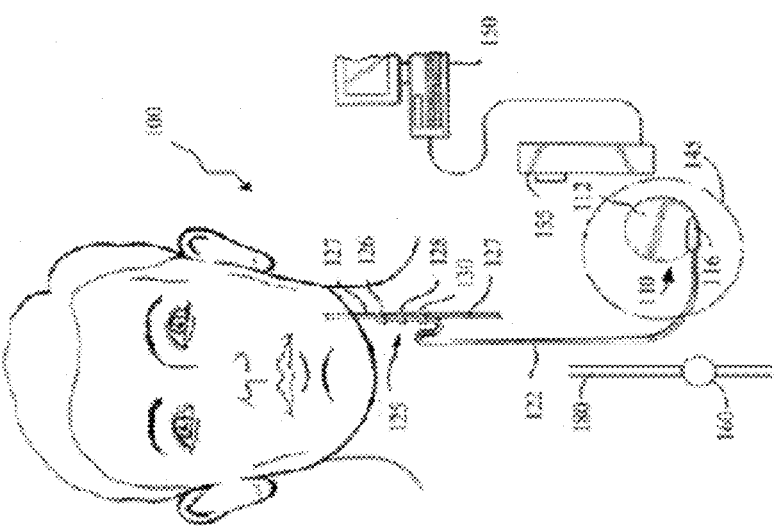
FIG. 1B provides a stylized diagram of a medical device which may be implanted into a patient's body for providing a therapeutic electrical signal to a neural structure of the patient's body, in accordance with one illustrative embodiment of the present invention.
Figure 1C:
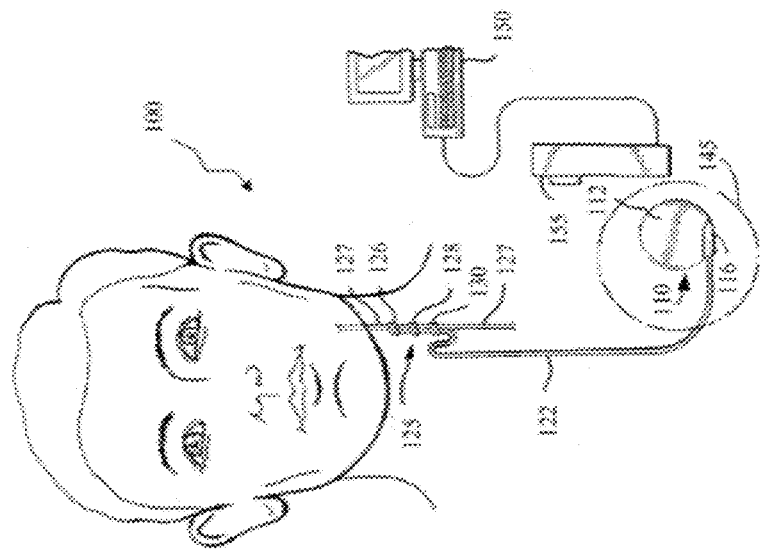
FIG. 1C provides a stylized diagram of a medical device which may be implanted into a patient's body for providing a therapeutic electrical signal to a neural structure of the patient's body, in accordance with one illustrative embodiment of the present invention.

Turning now to FIGS. 1A-1C, stylized medical systems (MDs) 100 for implementing one or more embodiments of the present invention are depicted. These drawings and MDs 100 are described in A Systems Approach to Disease State and Health Assessment (FIGS. 3A-3C) by Dr. Ivan Osorio (U.S. application Ser. No. 12/816,357), incorporated herein in its entirety. It is noted that the described MDs 100 may be implantable/implanted or non-implantable/non-implanted without departing from the spirit and scope of embodiments described herein.

Figure 2:
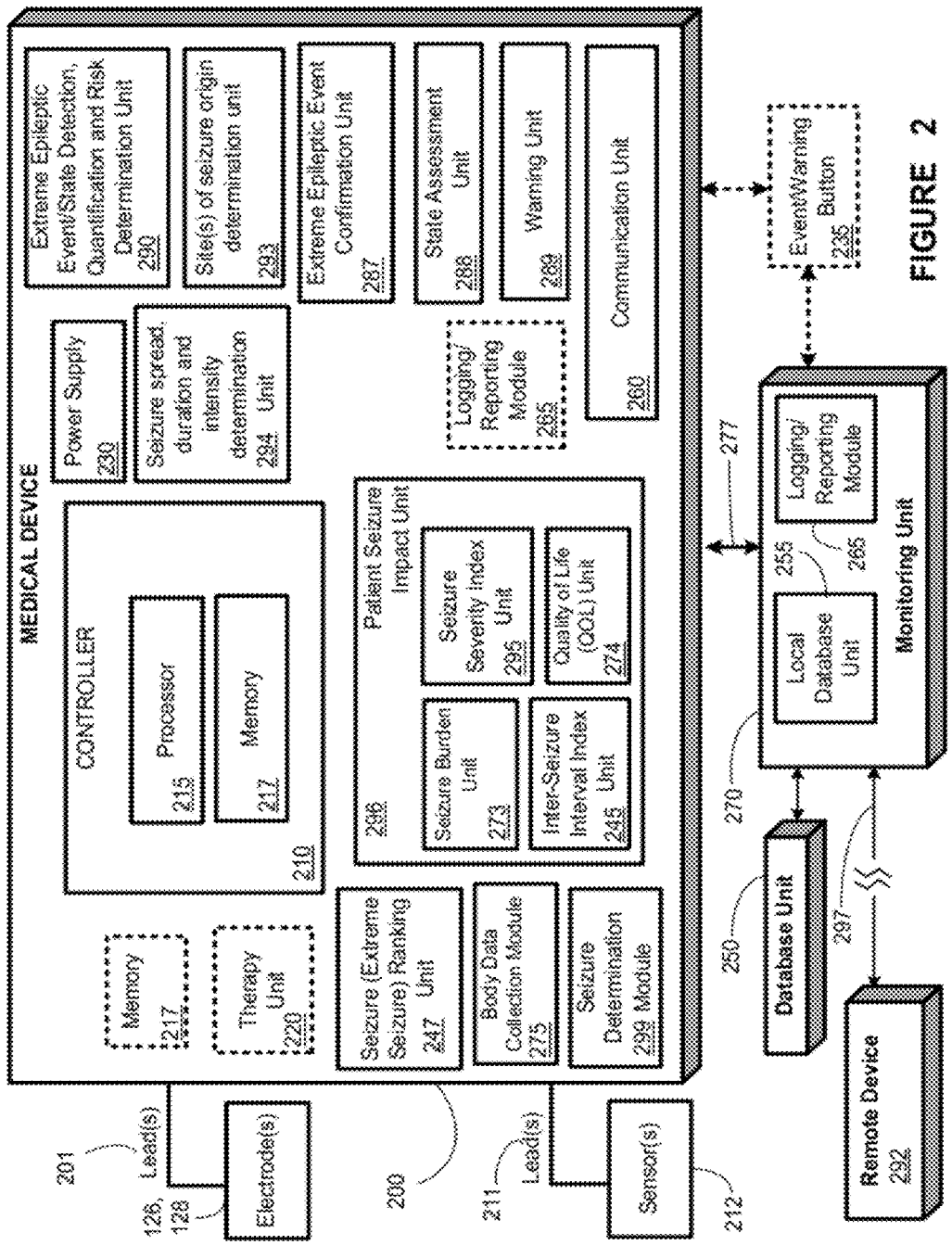
FIG. 2 illustrates a medical device for anticipating, detecting, assessing and managing (e.g., treating, warning, logging) extreme events related to epilepsy, in accordance with an illustrative embodiment of the present invention.

Turning now to FIG. 2, a block diagram depiction of a medical device (MD) 200 is provided, in accordance with one illustrative embodiment of the present invention. In some embodiments, the MD 200 may be implantable (such as implantable electrical signal generator 110 from FIG. 1), while in other embodiments the MD 200 may be completely external to the body of the patient.

The MD 200 (such as generator 110 from FIG. 1) may comprise a controller 210 capable of controlling various aspects of the operation of the MD 200. The controller 210 may include a processor 215, a memory 217, etc., for processing and storing data respectively. The processor 215 may comprise one or more microcontrollers, microprocessors, etc., capable of performing various executions of software and/or firmware components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc. In one embodiment, a memory 217 may be separate from, but communicatively coupled to the controller 210.

The controller 210 is capable of receiving internal data or external data, and in one embodiment, is capable of processing body data to identify an extreme epileptic event in a patient. For example, the controller 210 may receive data from a body data collection module 275 (described further below) or from a memory 217. Upon receiving the data or body data, the processor 215 may process the data in accordance with various embodiments described herein. For example, in one embodiment, the process may be adapted to compare values associated with two or more body data indices. The processor 215 may also provide processed data/body data to other modules and units in the MD 200. The controller 210 is capable of causing a therapy unit 220 to take responsive action in response to the identification of one or more various extreme or non-extreme epileptic events by the MD 200, or by a patient, a physician, a nurse or caregiver, etc. In one embodiment, the responsive action may comprise generating and delivering an electrical signal to target tissues of the patient's body for treating a medical condition. In one or more embodiments, the responsive action may comprise drug treatments, oxygen treatments, cooling and/or the like. For example, the controller 210 may receive manual instructions from an operator externally, or may cause the electrical signal to be generated and delivered based on internal calculations and programming. In other embodiments, the MD 200 does not comprise a therapy unit 220. In either embodiment the controller 210 is capable of affecting, and/or may be adapted to affect, substantially all functions of the MD 200.

As stated above, in one embodiment, the MD 200 may also comprise a therapy unit 220 capable of generating and delivering electrical signals to one or more electrodes 126, 128 via leads 201 (FIGS. 2B, 2D) (and/or other therapies such as drugs, thermal energy, oxygen and/or the like). A lead assembly such as lead assembly 122 (FIG. 1) may be coupled to the MD 200. Therapy may be delivered through the leads 201 comprising the lead assembly 122 by the therapy unit 220 based upon instructions from the controller 210. The therapy unit 220 may comprise various circuitries, such as electrical signal generators, impedance control circuitry to control the impedance "seen" by the leads, and other circuitry that receives instructions relating to the delivery of the electrical signal to tissue. Electrical signals delivered to a body part for therapeutic purposes may be of constant current (to compensate for impedance changes) or of constant voltage. The therapy unit 220 is capable of delivering electrical signals over the leads 201 comprising the lead assembly 122. As should be apparent, in certain embodiments, the MD 200 does not comprise a therapy unit 220, lead assembly 122, or leads 201. In particular, although FIGS. 2B and 2D are illustrated with therapy unit 220, leads 201 and electrodes 126, 128, in alternative embodiments, these structures and the stimulation function enabled thereby may be omitted.

In other embodiments, a lead 201 is operatively coupled to an electrode 126, 128, wherein the electrode 126, 128 is adapted to couple to at least one of a portion of a brain structure of the patient 190, a cranial nerve of a patient, a spinal cord of a patient 180, a sympathetic nerve structure of the patient, a peripheral nerve of the patient, a dermis and/or subdermis of a patient.

The MD 200 may also comprise a power supply 230. The power supply 230 may comprise a battery, voltage regulators, capacitors, etc., to provide power for the operation of the MD 200, including delivering the therapeutic electrical signal. The power supply 230 comprises a power source that in some embodiments may be rechargeable. In other embodiments, a non-rechargeable power source may be used. The power supply 230 provides power for the operation of the MD 200, including electronic operations and the electrical signal generation and delivery functions. The power supply 230 may comprise a lithium/thionyl chloride cell or a lithium/carbon monofluoride (LiCFx) cell if the MD 200 is implantable, or may comprise conventional watch or 9V batteries for external (i.e., non-implantable) embodiments. Other battery types known in the art may also be used.

The MD 200 may also comprise a communication unit 260 capable of facilitating communications between the MD 200 and various devices. In particular, the communication unit 260 is capable of providing transmission and reception of electronic signals to and from a monitoring unit 270, such as a handheld computer or PDA that can communicate with the MD 200 wirelessly or by cable. The communication unit 260 may include hardware, software, firmware, or any combination thereof.

The MD 200 may also comprise one or more sensor(s) 212 coupled via sensor lead(s) 211 to the MD 200. The sensor(s) 212 are capable of receiving signals related to a body parameter, such as the patient's heart beat or a body chemical, and delivering the signals to the MD 200. In one embodiment, the sensor(s) 212 may be the same as implanted electrode(s) 126, 128 (FIG. 1). In other embodiments, the sensor(s) 212 are separate structures that may be placed on the patient's skin, such as over the patient's heart or elsewhere on the patient's body. It will be appreciated by persons of skill in the art that in some embodiments, lead 211 may be omitted and the MD 200 may communicate wirelessly with sensor 212.

The MD 200 may also comprise a body data collection module 275. The body data collection module 275 may be adapted to, and/or capable of, collecting data relating to the body of a patient. Such data may be obtained using electrical, chemical, optical, biophotonic, acoustic (e.g., ultrasound), thermal sensors, pressure sensors, bioassays, chemical methods, imaging technology and/or motion sensors in any useful combination (these measurements may be performed at one or multiple spatial scales simultaneously or sequentially (e.g., multiplexing) and include but are not limited to: 1. Neurologic data such as neuronal electrical activity, neurotransmitter concentrations and their rate(s) of release and uptake, Kreb's and other cycle compounds, other chemical compounds (e.g., electrolytes, tissue stress markers), CSF and brain tissue pressure, temperature, and/or kinematic/kinetic activity, including but not limited to posture and fine motor movements among others using imaging techniques (e.g., video), accelerometers, inclinometers, actigraph devices, and/or the like; 1a. Level of consciousness and/or cognitive signals (e.g., attention, reaction time, memory, etc), neurological tests administered manually and/or automatically for qualitative or quantitative analyses; 2. Cardiac signals (e.g., as discussed above); 3. Body fluids signals including, but not limited to, those that may recorded using pressure, flow velocity and degree of laminarity (or turbulence) (e.g., Doppler), temperature, pH, chemical makeup (e.g., electrolytes, enzymes, tissue stress markers, anti-oxidants, gases); 4. Respiratory rate, pattern, tidal volume, and/or degree of activity of principal and/or accessory respiratory muscles to compute, for example, ratios (e.g., abdominal wall motion/thoracic wall motion, end tidal $CO_2$); 5. Endocrine indices (e.g., as discussed above); 6. Metabolic parameters (e.g., as discussed above); and 7. Kinetic data (e.g., as discussed above). This list is not exclusive, and the body data collection module 275 may collect additional data not listed herein, that would become apparent to one of skill in the art having the benefit of this disclosure. The body data collection module 275 may collect body data via one or more body data units (described in further detail below with respect to exemplary embodiments shown in FIGS. 3 & 4, [361-368]). The body data units, as shown below, may be internal to the MD 200, or external to, and communicatively coupled to, the MD 200. All data comparisons may be made taken into consideration including, but not limited to, ultradian, circadian or infradian variations, gender, body mass index, age, past and present treatments (e.g., drugs, electrical signal therapy, and/or the like), physical fitness/integrity, etc.

The body data collection module 275 may, in some embodiments, organize or process portions of the body data collected. Additionally, the body data collection module 275 may store or buffer the body data before sending the body data to other components of the MD 200. In accordance with one embodiment, the body data collection module 275 may send some or all of the body data collected by the body data collection module 275 to the controller 210 for processing. In other embodiments, the body data collection module 275 may send collected body data to other components of the medical device instead of, or in addition to, the controller 210; such other components include, but are not limited to, a SUDEP risk determination unit 285, a seizure severity ranking unit 299, a seizure severity index (SSI) unit 295 and an extreme epileptic event/state detection, quantification and risk determination unit 290. The body data collection module 275 may also send the body data to the monitoring unit 270 or remote device(s) 292 via communication unit 260.

The MD 200 may also comprise a seizure spread, duration and intensity determination unit 294. In accordance with one embodiment, the seizure spread, duration and intensity determination unit 294 may determine the amount of spread the seizure event and/or extreme seizure event. In other words, the greater the seizure spread, the more areas of the brain and/or body organs are affected by the seizure event and/or extreme seizure event. The seizure spread, duration and intensity determination unit 294 may make such a determination based upon body data information, external indications, and/or other data that would become apparent to one of skill in the art having the benefit of this disclosure.

The seizure spread, duration and intensity determination unit 294 may be adapted to provide seizure duration data which may include the duration of a patient's seizure event. The duration of a seizure event may be determined as the time that any of the autonomic, neurologic, metabolic, endocrine, or stress tissue marker indices values differ from inter-ictal and/or post-ictal values. In some embodiments, electrographic or clinical onset may be approximated by other body parameters, e.g., heart rate, kinetic activity, etc. In alternative embodiments, the duration of a seizure event may be determined as the time a body data value, a site(s) data value and/or an intensity, duration and spread data value (or value(s) respectively related thereto) is above or below adaptable and/or pre-determined threshold(s) and/or separatrix(tices). In further embodiments, the duration of a seizure event may be based on other criteria as would be apparent to one of skill in the art having the benefit of this disclosure. The seizure spread, duration and intensity determination unit 294 may also be adapted to determine a time spent in a seizure event state over a given time period or window (e.g., macroscopic as defined above); such a determination may include one or more seizure events occurring within the time period (as discussed in further detail below with respect to FIG. 13). The time periods/windows may be of a fixed duration or may be of adjustable duration; likewise, the time period or window may move with or without overlap.

The seizure spread, duration and intensity determination unit 294 may be adapted to provide seizure intensity data which may include the energy associated with a patient's seizure event. As described above, seizure intensity may be defined as the value of any one, or any number, of body data values during a seizure event. A maximum intensity of a seizure may be defined as the maximum value of any one, or any number, of body data values during a seizure event (e.g., the maximum heart rate of a patient during a seizure event).

The MD 200 may also comprise a seizure severity index (SSI) unit 295. SSIs may be calculated in some embodiments using at least two of seizure intensity, duration or extent of spread and using at least of one autonomic, endocrine, metabolic, stress tissue marker signals. For example, SSI may be the product of intensity and spread or the sum of intensity, duration and spread using one or more organ/system indices. In accordance with one embodiment, the SSI unit 295 may determine one or more seizure severity indices (SSIs) based upon the body data collected by the body data collection module 275 and/or other relevant data. An SSI may be a scalar-valued function of one or more body data variables that simplifies a possibly complex set of body information down to a single number: the SSI. In accordance with one embodiment, the SSI may be any statistic (or scalar-valued function) associated with a seizure with the property values that reflect some aspect of the severity of the corresponding seizures and may be ordered/sorted so that the distance between the SSI values for different seizures can be measured, compared and/or interpreted to provide meaningful information. In one embodiment, the SSI may be a quantity whose variation over a period of time measures the change in some body data or body phenomenon. In one embodiment, the SSI may be intended to generally reflect the impact of a seizure on a body organ or system. The SSI may also be a statistic associated with the seizure that enables comparison between different seizures, and the values for different seizures may be ordered/sorted and the distance (in a Euclidian or non-Euclidian sense) between them measured/compared/interpreted to provide meaningful information. If the SSI values describe the severity of the seizure not in absolute terms, but in a manner relative to other seizures for that patient (or relative to other patients), the SSI may be referred to as a "Relative SSI." Additionally, when more than one SSI is used at the same time, the plurality of SSIs may be combined into a single SSI by weighted averaging, and/or the like.

The MD 200 may also comprise an inter-seizure interval index unit 245. In accordance with one embodiment, the inter-seizure interval index unit 245 may determine an index based upon inter-seizure interval. The inter-seizure interval index may, in some embodiments, be representative of the current inter-seizure interval relative to past single values, sets or values or value distributions and/or expected inter-seizure intervals, either for a specific patient or for one or more patients or patient populations. The inter-seizure interval index unit 245 may make such rankings based upon body data information, external indications (e.g., the patient's environment or surroundings), a patient's past seizure data, a normalized seizure data distribution, expected seizure data and/or other data that would become apparent to one of skill in the art having the benefit of this disclosure. Additionally, the inter-seizure interval index unit 245 may base its index upon a comparison of any or all of the above referenced data, information or indications.

Inter seizure intervals (ISIs), post-ictal severity indices (PISIs), seizure severity indices (SSIs) and patient seizure impact (PSimp) may be used alone or in combination to determine the probability that an extreme event will occur, is occurring or has occurred. These data may be derived using one or more autonomic (e.g., cardiac, respiratory, dermal), endocrine (e.g., prolactin), metabolic (e.g., arterial pH), tissue stress markers (e.g., CK) or neurologic (e.g., kinetic, cognitive) signals.

In one more embodiments identifying an occurrence of an extreme event with a certain probability or an increased risk of an extreme event state with a certain probability may be based upon a comparison of a determined SSI, ISI or PSimp values or upon models based, among others, on the temporal evolution of SSI, ISI or PSimp (for a specific patient or patient populations) in any combination.

The MD 200 may also comprise a seizure (extreme seizure) ranking unit 247. In accordance with one embodiment, the seizure (extreme seizure) ranking unit 247 may determine a ranking of a seizure event and/or extreme seizure based upon severity, ISI, PISI, PSimp, PSB and/or other factors. In one or more embodiments, the seizure (extreme seizure) ranking unit 247 may rank either seizure events or extreme seizure events. That is, in various embodiments, the seizure (extreme seizure) ranking unit 247 may be used for ranking one of seizure events or extreme seizure events. Alternatively, in one embodiment, multiple instances of the seizure (extreme seizure) ranking unit 247 may be implemented in the MD 200 (e.g., one instance for ranking seizure events and one instance for ranking extreme seizure events). As such, specific determinations relative to seizure events and/or extreme seizure events may be made independently of each other. For instance, a library or report log of just extreme seizure events may be maintained; this may allow for extreme seizure event comparisons and rankings which need not include non-extreme seizure events.

The ranking of seizure events and/or extreme seizure events may, in some embodiments, be based upon a reference value that may in turn be based upon normative, reference and/or historical patient data, or the like, which may be patient-specific or for particular patient populations. In the case of extreme events, an extreme reference value may be used. An extreme reference value may be a reference value above and beyond that used to indicate non-extreme seizure events. In other words, the seizure (extreme seizure) ranking unit 247 may make such rankings based upon body data information, external indications, a patient's past seizure data and/or other data that would become apparent to one of skill in the art having the benefit of this disclosure. Additionally, the seizure (extreme seizure) ranking unit 247 may base its ranking(s) upon a comparison of any or all of the above referenced data, information or indications.

The MD 200 may also comprise a site(s) of seizure origin determination unit 293. In accordance with one embodiment, the site(s) of seizure origin determination unit 293 may determine the site or sites of origin of a seizure event and/or extreme seizure event in a patient's brain. This information may be used to determine different types of seizure events, rank them according to severity (SSI), ISI, PISI, PSimp and/or PSB according to site of origin and classify them as extreme or non-extreme events. The site(s) of seizure origin determination unit 293 may make such a determination based upon body data information, external indications, and/or other data that would become apparent to one of skill in the art having the benefit of this disclosure. In one embodiment, patients in whom seizures originate from more than one brain site ("focus") within a region, one region in a lobe, one lobe within a hemisphere and/or one hemisphere, SSI, ISI, PISI, PSimp and/or PSB values may be determined from each site, region, lobe and/or hemisphere by performing statistical analyses to obtain measures of central tendency (e.g., mean), distributions (either temporal, spatial or both), and comparing the determined SSI value to reference/extreme reference value(s) that may or may not include a status epilepticus value. The status epilepticus value may be based upon at least one determination of if a status epilepticus event is occurring or the probability that it may occur.

The MD 200 may also comprise a seizure determination module 299. In accordance with one embodiment, the seizure determination module 299 may determine whether or not a patient has had, or is having, a seizure/extreme seizure event using body data. The seizure determination module may make such a determination based upon body data information, external indications, and/or other data that would become apparent to one of skill in the art having the benefit of this disclosure.

The MD 200 may also comprise a patient seizure impact (PSimp) unit 296. In accordance with one embodiment, the PSimp unit 296 may determine one or more seizure impact indices (PSimps) based upon the body data collected by the body data collection module 275 and/or other relevant data. IO: redundant The PSimp provides information not contained in the SSI (or in the inter-seizure interval index (ISI)) with regard to the effect of a seizure upon one or more body organs or parts. Two seizures (e.g., convulsions) with identical SSI may have a different impact on a patient: If during one such seizure (SSI=2200) the patient is walking downstairs, falls down suffers skull and rib fractures and brain contusions and during another seizure (SSI=2200) the patient is sitting down and drops onto a carpeted floor and does not suffer any injuries, the PSimp of the first seizure is considerable higher than that of the second one. Yet another example may be a patient whose overall health and body state is diminished by successive, similar seizure events and/or extreme seizure events after which the patient is not able to return to baseline with respect to one or more body parameters. Given the patient's diminished state, a subsequent, similar seizure event and/or extreme seizure event may have a more detrimental impact upon the patient than the previous, similar seizure events and/or extreme seizure events.

The PSimp may be a function of a patient's health, age, physical fitness/integrity, circumstances, conditions and activities the patient is performing as a seizure occurs. That is, PSimp, depends on the time of day (day vs. night) patient's body state (e.g., body position), condition of one or more organ(s), level of physical activity (e.g., running vs. lying down), location of the patient (swimming in a pool vs. lying down in bed), state of alertness (awake vs. asleep), and the like.

In accordance with one embodiment, the PSimp may be any statistic (or scalar-valued function) that reflect some aspect of the impact of seizures on a patient and may be sorted out and ranked so that the PSimp for different seizures can be measured, compared and/or interpreted to provide meaningful information. If the PSimp values describe the impact of the seizure not in absolute terms, but in a manner relative to other seizures for that patient (or relative to other patients), the PSimp may be referred to as a "Relative PSimp." Additionally, when more than one PSimp is used at the same time, the plurality of PIs may be combined into a single PSimp by weighted averaging, and/or the like. Furthermore, the PSimp alone (e.g., independent of SSI or ISI) may determine whether or not a seizure event is classified as extreme. In the example above, while the two seizures' SSIs are identical (2200), the one associated with bone fractures and brain contusion is extreme while the other is not. The PSimp value may be indicative of a risk of extreme events or states such as status epilepticus, SUDEP, body injuries and/or the like.

In one embodiment, the PSimp unit 296 may be adapted to perform a method, comprising receiving body data relating to at least one of an autonomic signal, a neurologic signal, an endocrine signal, a metabolic signal, or a body injury scale; identifying a seizure event based upon said body data; determining at least one PSimp value (quantitatively or qualitatively) reflective of the severity of said seizure event based at least upon said body data; comparing said determined at least one PSimp value to at least one reference value or extreme reference value; and identifying at least one of an occurrence of an extreme seizure event or an occurrence of a non-extreme seizure event, said identification being based upon at least the comparison of said determined PSimp value to said at least one reference value or extreme reference value. The SSI unit 295, which may be incorporated into the PSimp unit 296 in one or more embodiments, may be adapted to and/or be capable of making a qualitative assessment of the PSimp value, such as: non-existent, mild, moderate and severe. The SSI unit 295 may be adapted to and/or be capable of determining a scaled value associated with said PSimp value based at least upon a quantitative assessment of the PSimp value; and assigning said PSimp value to a PSimp ranking unit.

The PSimp also increases specificity of event detection and getting performance closer to the goal of "zero false positives." That is, if a seizure event and/or an extreme seizure event impacts a patient, the seizure event and/or an extreme seizure event would be unequivocally detected and/or identified. The impact of a seizure event and/or an extreme seizure event may be detected in any number of ways. In other words, even if a seizure event and/or an extreme seizure event is not detected based upon metrics based for example on heart rate and respirations directly indicative of an ictal state, its impact on the patient's health or quality of life (QOL) and mental health, would be detectable. This indirect impact may or may not be perceived by the patient or the caregivers but it may be determined, logged and recorded in one embodiment of this invention. For example, cumulative decline in heart rate variability as a function of recurring seizures, a change associated with an increased mortality risk that cannot be perceived by the patient or by caregivers without resorting to sophisticated statistical analyses, may be tracked, quantified, logged and recorded in one embodiment of this invention. Similarly, other unperceived extreme metrics may be quantified in addition to, or instead of, the logging of the impact and/or PSimp value.

In one or more embodiments, the PSimp unit 296 may also comprise a patient seizure burden (PSB) unit 273 adapted to determine a seizure burden on the patient and in another embodiment the PSB unit 273 may be separate from the PSimp unit 296. PSB is determined by measuring the magnitude of change (e.g., decline), rate of change of any and all of body organs/systems through analysis of any or all of their indices. PSB may be also determined by identifying the appearance of abnormalities in any body organs/systems, quantifying them and logging the results and time of occurrence of changes for future comparisons. For example, a highly relevant neurologic index, such as memory may be measured over time using validated tests and the scores may be used to determine if there is deterioration in this index, its magnitude and rate of change. In one embodiment, statistical analysis (e.g. regression analysis) may be performed to better identify the seizure contribution to the deterioration in certain or to the appearance of abnormalities (e.g. multi-focal PVCs). To this end, the indices used to measure PSB are for example correlated with the sum of SSI values over a time window (e.g., macroscopic) or a window based on some other time scale, or with the sum of SSI values per unit time multiplied by the time spent in seizure per unit time. Other means to determine the role of seizure in the patient's deterioration are:

a) the sum of SSI values over a time window divided by mean or median inter-seizure interval (ISI) value over that time window; b) the sum of SSI and post-ictal severity indices (PISI) over a time window or the sum of SSI and PISI multiplied by the sum of times spent in the seizure and post-ictal states over that time window; c) Seizure temporal density defined as the time spent in seizure over a time window divided by the number of seizure events over that time window; d) a product of time spent in seizure and the mean or median SSI value over that time window, divided by the number of seizures over that time window; e) the relation of an SSI or ISI value to other values/measures at different times. It should be noted that seizure burden may vary due to the time of day/night: one or more extreme/non-extreme values may be chosen as a reference value for times of sleep or wakefulness. That is, when calculating and comparing a seizure burden, it may be useful to compare the seizure burden value to one obtained at same time of day or state (i.e., morning to morning, sleep-to-sleep and/or resting to resting).

In addition to the PSimp and PSB measures, comparisons of SSI, PISI and/or ISI values to historical values allows quantification of the evolution of epilepsy as a function of time, therapies and preventive measures. For example, by plotting SSI values on the y-axis over a time window (x-axis) trends in the direction of improvement, worsening or stabilization of epilepsy may be easily determined Increases in SSI or PISI values and/or decreases in ISI as a function of treatment may require a warning and appropriate therapy/treatment.

In another embodiment, a quality of life (QOL) unit 274 may be incorporated into the PSimp unit 296 to determine the impact of epilepsy and seizures on a patient's QOL. The QOL unit 274 may be adapted to determine/quantify one or more QOL factors for a patient, such as mood, sense of well-being (or lack of it thereof), sexual activity and/or the like. The determination of various QOL factors may be used in the calculation/determination of PSB. In yet another embodiment, the physical fitness/integrity index unit 355 and the physical fitness/integrity determination unit 376 may be incorporated into PSimp unit 296 or in into a PSB unit 273 to determine the impact of the physical fitness/integrity index on the PSB. Decreases in fitness/integrity as documented using fitness/integrity measures may be correlated for example with SSI as detailed above to determine its contribution to loss of fitness/integrity).

The MD 200 may also comprise an extreme epileptic event/state detection, quantification and risk determination unit 290. In accordance with one embodiment, the extreme epileptic event/state detection, quantification and risk determination unit 290 may determine a current state and/or a future risk of entering a status epilepticus state. In one embodiment, the extreme epileptic event/state detection, quantification and risk determination unit 290 may identify a status epilepticus event from a group consisting of a present status epilepticus state, a past status epilepticus state or an increased risk of a status epilepticus state. The determination and/or identification of a risk/state of an extreme event such as status epilepticus may be made based in part or whole upon a comparison of one or more SSI, PISI and/or ISI values to a status epilepticus threshold value(s) or to a reference/extreme reference value that may in turn be based upon reference, normative and/or historical patient data, or the like.

The MD 200 may also comprise an extreme epileptic event confirmation unit 287. In accordance with one embodiment, the extreme epileptic event confirmation unit 287 may confirm that a patient is having an extreme epileptic event and that said event is status epilepticus. The extreme epileptic event quantification and confirmation unit 287 may also confirm that a patient remains in a state of status epilepticus subsequent to an initial detection/identification of the state of status epilepticus.

The MD 200 may also comprise a state assessment unit 288. In accordance with one embodiment, the state assessment unit 288 may indicate various states of a patient's disease, including but not limited to, a status epilepticus event, a risk of SUDEP, a current seizure event, variations in body data indicative of an event/change of a patient's disease state, and the like. In one embodiment, the indication may be provided to other components within the MD 200, to the monitoring unit 270 and/or database unit 250 and/or local database unit 255, to a remote device 292, to the PSimp unit 296, to the PSB unit 273, to a patient, to a caregiver or physician, or the like. The state assessment unit 288 may further indicate that the state or change in state of the patient's disease should be logged, for example, in database unit 250, local database unit 255, and/or the like.

The MD 200 may also comprise a warning unit 289. In accordance with one embodiment, the warning unit 289 may issue a warning to a patient, physician and/or care giver. Such a warning may be indicative of various states of a patient's disease, including but not limited to, an extreme epileptic event such as status epilepticus, a risk of SUDEP, a current seizure event, variations in body data indicative of an event/change of a patient's disease state, and the like, as described above with respect to the state assessment unit 288. Additionally, the warning unit 289 may warn that an event presents an increased risk to the health and/or safety of the patient. The warning unit 289 may provide a warning for a patient, physician and/or care giver to take some immediate or otherwise urgent action related to the event/change of a patient's disease state. The warning unit 289 may warn in addition, or alternatively, to the indication provided by the state assessment unit 288 described above.

The MD 200 may also comprise an event/warning button 235. In accordance with one embodiment, the event/warning button 235 may be located external to the MD 200 in an implanted/non-implanted embodiment, or may be part of the MD 200 in non-implanted embodiments. The event/warning button 235 may be communicatively coupled to the MD 200 and/or to the monitoring unit 270 in various embodiments. The event/warning button 235 may allow for a patient or other individual (such as a caregiver, family member or emergency response personnel) to activate a warning to identify a seizure event and/or an extreme seizure event/state. Such activation may be used to warn of, treat and/or log a seizure event and/or an extreme seizure event/state. Additionally, in one or more embodiments, the event/warning button 235 may be used to elevate a warning or therapy for an existing seizure event and/or an extreme seizure event/state.

In addition to components of the MD 200 described above, an non-implantable/implantable medical system may comprise a storage unit to store an indication of at least one of epilepsy event (e.g., a seizure or an increased risk of a seizure). The storage unit may be the memory 217 of the MD 200, another storage unit of the MD 200, or an external database, such as the local database unit 255 or a remote database unit 250. The MD 200 may communicate the indication via the communications unit 260. Alternatively or in addition to an external database, the MD 200 may be adapted to communicate the indication to at least one of a patient, a caregiver, or a healthcare provider.

In various embodiments, one or more of the units or modules described above may be located in a monitoring unit 270 or a remote device 292. For example, in one exemplary embodiment, the extreme epileptic event/state detection, quantification and risk determination unit 290 may be external to the MD 200, e.g., in a monitoring unit 270 or a remote device 292. Locating the extreme epileptic event/state detection, quantification and risk determination unit 290 outside the MD 200 may be advantageous if the status epilepticus risk determination or detection parameter calculation is computationally intensive, in order to reduce energy expenditure and heat generation in the MD 200 or to expedite calculation of the at least one status epilepticus risk determination or detection parameter.

The monitoring unit 270 may be a device that is capable of transmitting and receiving data to and from the MD 200. In one embodiment, the monitoring unit 270 is a computer system capable of executing a data-acquisition program. The monitoring unit 270 may be controlled by a healthcare provider, such as a physician, remotely at a base station, for example, from a doctor's office or also directly. In alternative embodiments, the monitoring unit 270 may be controlled by a patient in a system providing less interactive communication with the MD 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the MD 200 for programming the operation of the medical device, and may also receive and upload various status conditions and other data from the MD 200. Communications between the monitoring unit 270 and the communication unit 260 in the MD 200 may occur via a wireless or other type of communication, represented generally by line 277 in FIG. 2. This may occur using, e.g., a wand 155 to communicate by RF energy with an MD 200. Alternatively, the wand may be omitted in some systems, e.g., systems in which the MD 200 is non-implantable, or implantable systems in which monitoring unit 270 and MD 200 operate in the MICS bandwidths.

Likewise, in various embodiments the remote device 292 may communicate with the monitoring unit 270, and thus with the MD 200, with communications between the remote device 292 and the monitoring unit 270 represented generally by line 297 in FIG. 2. Communications between the monitoring unit 270 and the remote device 292 may occur via a wireless or other type of communication represented by line 277.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more event detection parameters) using the monitoring unit 270, which may include obtaining and/or analyzing data from the MD 200 and/or data from the database unit 250 and/or the local database unit 255. The database unit 250 and/or the local database unit 255 may store various patient data.

The MD 200 may also comprise a logging/reporting module 265. The logging/reporting module 265 may be adapted to log and/or store data related to the patient, the patient's physical condition, the patient's disease and disease state and/or any other body data. The logging/reporting module 265 may be adapted to log and/or store information indicative of events relating to the patient's disease (e.g., seizure events, data related to time of recovery after seizure events and/or patient sleep-wake cycles). The logging/reporting module 265 may also be adapted to log and/or store a timestamp indicative of the time and day on which stored data is/was acquired. The logging/reporting module 265 may be adapted to report stored data, or any portion thereof, to a patient, a physician, a care giver, an external computer 150, a database unit 250, a local database unit 255 and/or a remote device 292. It is contemplated that the logging/reporting module 265 may not be present in the MD 200 in various embodiments, or alternatively, that the logging/reporting module 265 may be located in a monitoring unit 270 or a remote device 292.

One or more of the blocks illustrated in the block diagram of the MD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units from the various blocks illustrated in FIG. 2 may be combined into a programmable device, such as a field programmable gate array, an ASIC device, etc.

The medical device system, in one exemplary embodiment, provides for software module(s) that are capable of acquiring, storing, and processing various forms of data, such as patient data/parameters (e.g., body data such as heart rate, breathing rate, brain-activity parameters, PSimp data, PSB data (e.g., disease progression or regression data, quality of life data, etc.), and/or the like) as well as therapy parameter data (e.g., adverse effects). Therapy parameters may include, but are not limited to, electrical signal parameters that define therapeutic electrical signals delivered by the medical device in response to the detection of an epilepsy event, medication parameters and/or any other therapeutic treatment parameter. Therapy parameters for a therapeutic electrical signal may also include, but are not limited to, a current amplitude, a pulse width, a pulse shape, a frequency, an on-time, an off-time, etc.

In one exemplary embodiment, at least one electrode may be coupled of to each of two or more cranial nerves. (In this context, two or more cranial nerves mean two or more nerves having different names or numerical designations, and do not refer to the left and right versions of a particular nerve. However, bilateral (left and right) stimulation of the same nerve may be also carried out). In one embodiment, at least one electrode may be coupled to either or both vagus nerves or a branch of either or both vagus nerves. The term "operatively" coupled may include direct or indirect coupling. Each of the nerves in this embodiment or others involving two or more cranial nerves may be stimulated according to particular activation modalities that may be independent between the two nerves. In another embodiment, a therapy may be delivered directly to the brain.

Figure 3:
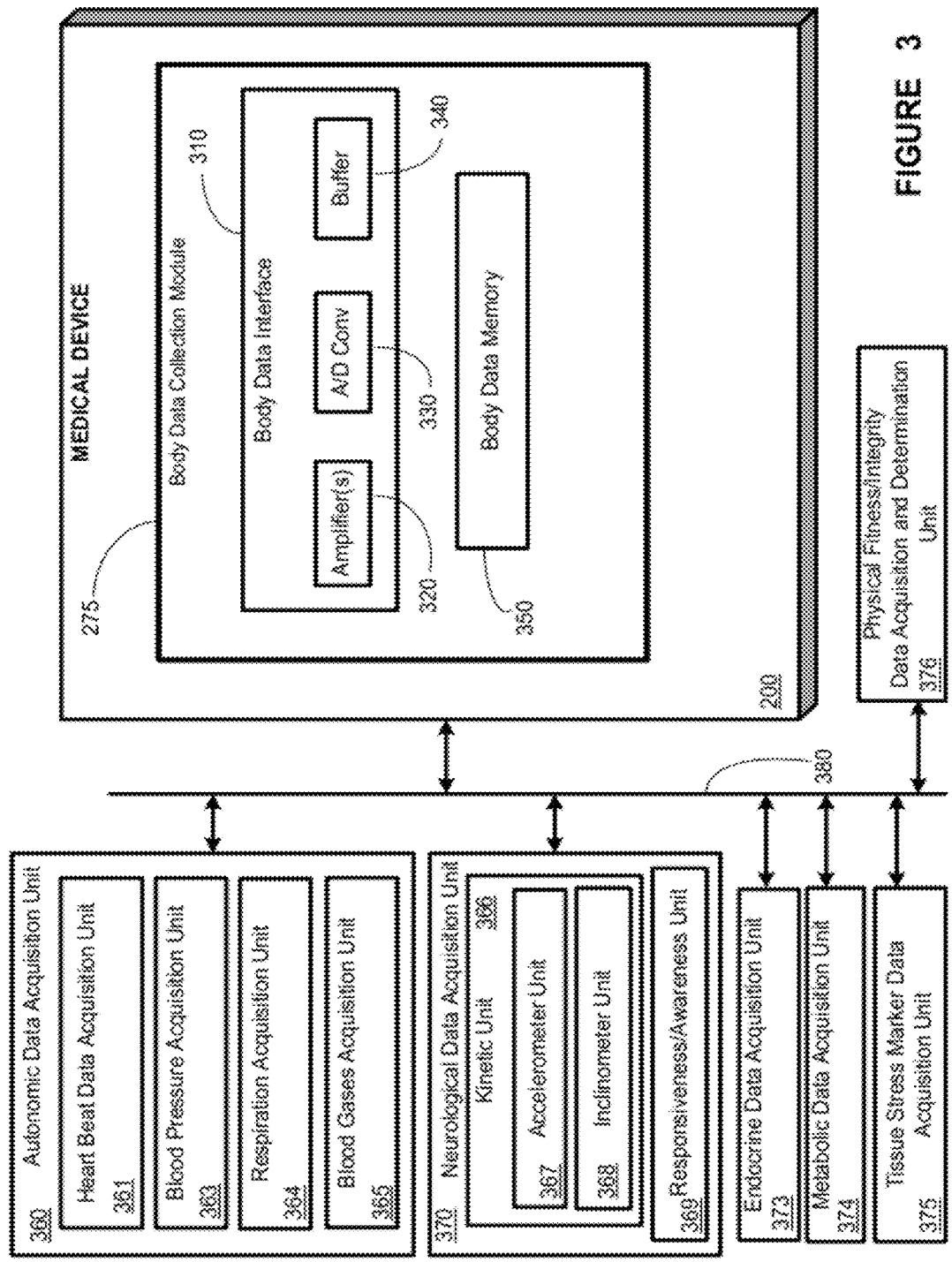
FIG. 3 provides a stylized diagram of a medical device and its different data acquisition units that may be implanted into a patient's body, in accordance with one illustrative embodiment of the present invention.

Turning now to FIG. 3, a block diagram depiction of an MD 200 is provided, in accordance with one illustrative embodiment of the present invention. FIG. 3 depicts an exemplary implementation of the body data collection module 275 described above with respect to FIG. 2. The body data collection module 275 may include hardware (e.g., amplifiers, accelerometers), tools for chemical assays, optical measuring tools, a body data memory 350 for storing and/or buffering data in the body data collection module 275. The body data memory 350 may, in some embodiments, be adapted to store body data for logging or reporting purposes and/or for future body data processing and/or statistical analyses. The body data collection module 275 may also include one or more body data interfaces 310. The body data interface 310 may provide an interface for input/output (I/O) communications between the body data collection module 275 and body data units/modules (e.g., [360-370], [373-376]) via connection 380. Connection 380 may be a wired or wireless connection, or a combination of the two. The connection 380 may be a bus-like implementation or may include an individual connection (not shown) for each, or some number, of the body data units (e.g., [360-370], [373-376]). The connection 380 may also include connection elements as would be known to one of skill in the art having the benefit of this disclosure. In various embodiments, the body data units may include, but are not limited to, an autonomic data acquisition unit 360, a neurologic data acquisition unit 370, and endocrine data acquisition unit 373, a metabolic data acquisition unit 374, a tissue stress marker data acquisition unit 375, a QOL unit 274 and/or a physical fitness/integrity acquisition and determination unit 376. In one embodiment, the autonomic data acquisition unit 360 may include a heart beat data acquisition unit 361 adapted to acquire a phonocardiogram (PKG), EKG, echocardiophraphy, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 366 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings. These lists are not exclusive, and the body data collection module 275 may collect additional data not listed herein, that would become apparent to one of skill in the art having the benefit of this disclosure. The body data units ([360-370], [373-376]) may be adapted to collect, acquire, receive/transmit heart beat data, EKG, PKG, echocardiogram, apexcardiogram, blood pressure, respirations, blood gases, body acceleration data, body inclination data, EEG/ECoG and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data units/modules (e.g., ([360-370], [373-376])) or signals to/from other units/modules of the MD 200. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 200 (e.g., memory 217, FIG. 2) or external to the MD 200 (e.g., monitoring unit 270, local database unit 255, database unit 250, remote device 292). The buffer(s) 340 may be adapted to buffer and/or store signals received by the body data collection module 275 as well as signals to be transmitted by the body data collection module 275. In various embodiments, the buffer(s) 340 may also be adapted to buffer and/or store signals in the body data collection module 275 as these signals are transmitted between components of the body data collection module 275.

As an illustrative example, in one embodiment, data related to a patient's respiration may be acquired by respiration unit 364 and sent to the MD 200. The body data collection module 275 in the MD 200 may receive the respiration data using body data interface(s) 310. As the data is received by the body data interface(s) 310, the incoming data may be amplified/conditioned by amplifier(s) 320 and then converted by A/D converter(s) into a digital form. The digital signal may be buffered by a buffer(s) 340 before the data signal is transmitted to other components of the body data collection module 275 (e.g., body data memory 350) or other components of the MD 200 (e.g., controller 210, processor 215, memory 217, communication unit 260, seizure determination module 299, SSI unit 295, extreme epileptic event/state detection, quantification and risk determination unit 290, or the like). Body data in analog form may be also used in one or more embodiments.

Figure 4:
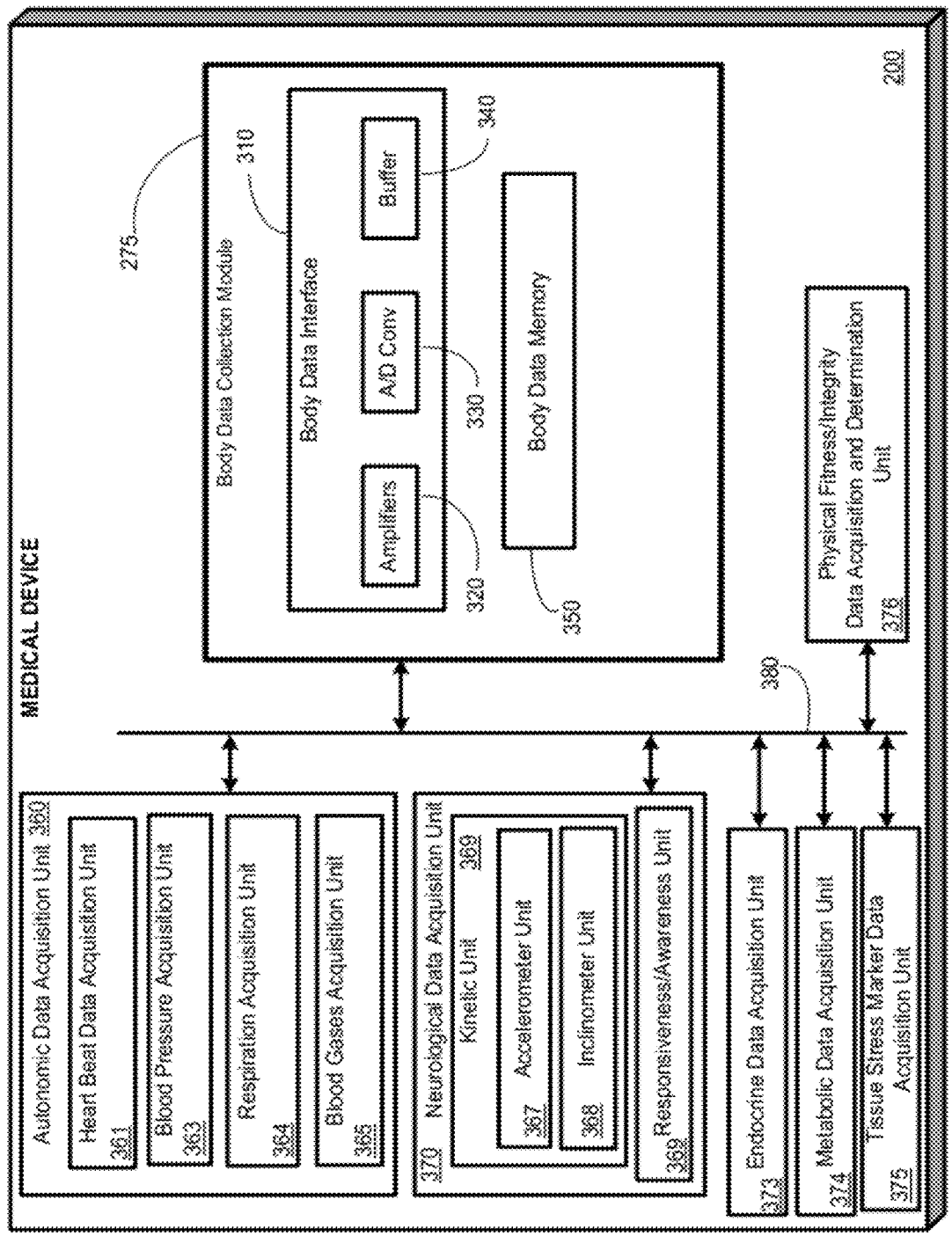
FIG. 4 provides a stylized diagram of a medical device which may be implanted into a patient's body, in accordance with one illustrative embodiment of the present invention.

Turning now to FIG. 4, an MD 200 (as described above in FIG. 3) is provided, in accordance with one illustrative embodiment of the present invention. FIG. 4 depicts the body data units (FIGS. 3 & 4, [360-370], [373-376]), in accordance with one embodiment, being externally coupled to the MD 200, instead of being included within the MD 200 as shown in FIG. 3. In accordance with various embodiments, any number and type of body data units (FIGS. 3 & 4, [360-370], [373-376]) may be included within the MD 200, as shown in FIG. 4 while other body data units (FIGS. 3 & 4, [360-370], [373-376]) may be externally coupled, as shown in FIG. 3. The body data units (FIGS. 3 & 4, [360-370], [373-376]) may be coupled to the body data collection module 275 in a fashion similar to that described above with respect to FIG. 3 (380), or in any number of different manners used in coupling intra-medical device modules and units. It should be noted that the manner by which the body data units (FIGS. 3 & 4, [360-370], [373-376]) may be coupled to the body data collection module 275 is not essential to and does not limit the embodiments described herein as would be understood by one of skill in the art having the benefit of this disclosure.

Figure 5A:
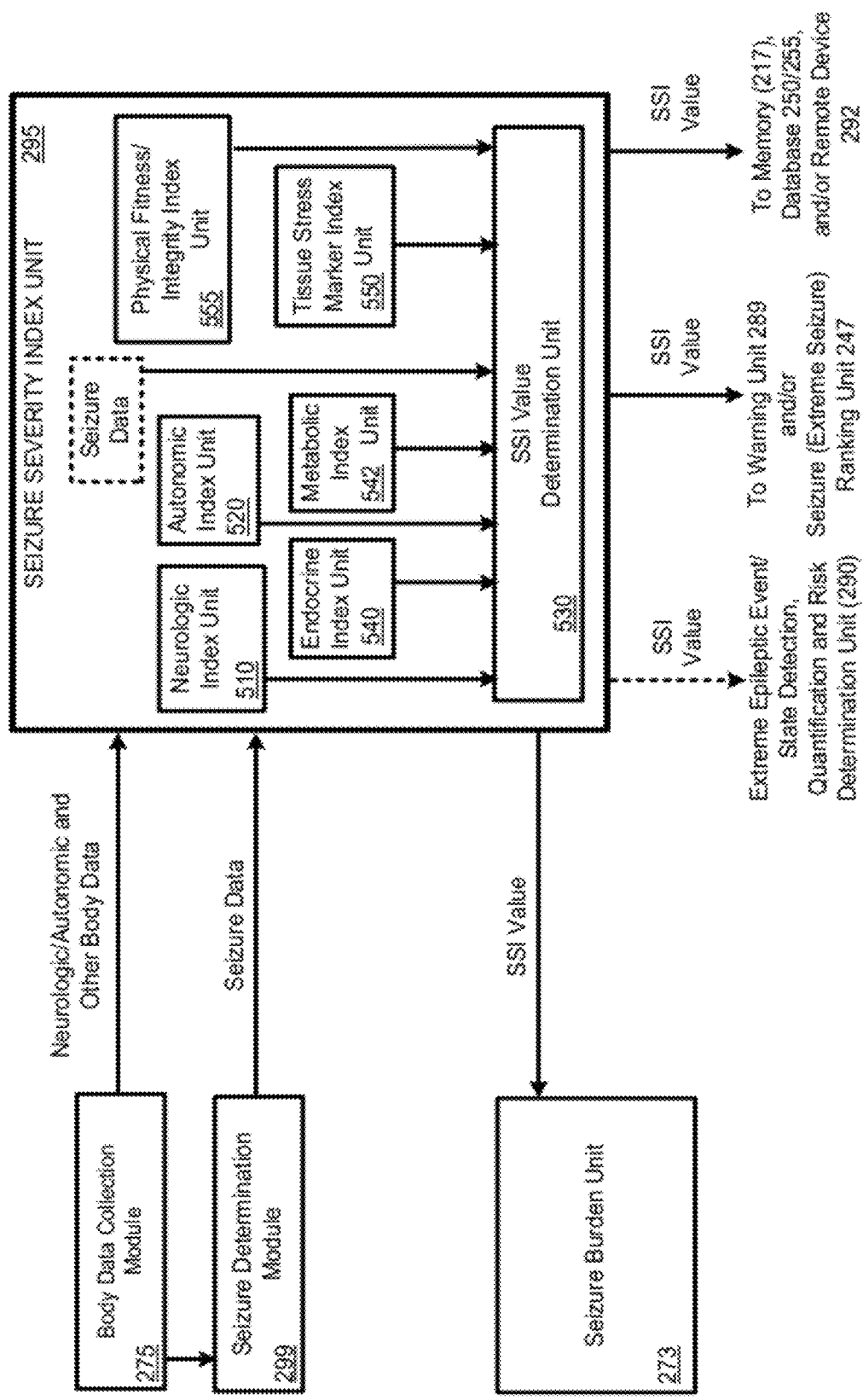
FIG. 5A provides a stylized diagram of a seizure severity index unit for determining a seizure severity index using body data and seizure data, in accordance with one illustrative embodiment of the present invention.

Turning now to FIG. 5A, a block diagram depiction of a seizure severity index unit 295 (SSI unit) is provided, in accordance with one illustrative embodiment of the present invention. In one embodiment, the SSI unit 295 may be adapted to determine a seizure severity index (SSI). The SSI unit 295 may use body data and/or seizure data (e.g., seizure intensity data, seizure duration data and/or seizure spread data) in determining the SSI. In one embodiment, body data collection module 275 may send body data to SSI unit 295. In one embodiment, the SSI unit 295 may include at least one of a neurologic index unit 510, an autonomic index unit 520, an endocrine index unit 540, a metabolic index unit 542 and/or a stress marker index unit 550 and/or a physical fitness/integrity index unit 555. The neurologic index unit 510 may be adapted to determine a neurologic index value using neurologic body data from the body data collection module 275. The autonomic index unit 520 may be adapted to determine an autonomic index value using autonomic body data from the body data collection module 275. The endocrine index unit 540 may be adapted to determine an endocrine index value using body data from the body data collection module 275. The metabolic index unit 542 may be adapted to determine a metabolic index value using body data from the body data collection module 275. The stress marker index unit 550 may be adapted to determine a stress marker index value using body data from the body data collection module 275. The physical fitness/integrity index unit 555 may be adapted to determine a stress marker index value using body data from the body data collection module 275. It is noted that the seizure determination module 299 may send seizure data to the SSI unit 295 and that units 510, 520, 540, 542, 550 and 555 may be adapted to determine their respective indices based on seizure data from seizure determination module 299.

The neurologic index unit 510, autonomic index unit 520, endocrine index unit 540, metabolic index unit 542, stress marker index unit 550, and physical fitness/integrity unit 555 may be adapted to transmit their respective index values to an SSI value determination unit 530. The SSI value determination unit 530 may use a neurologic index value, an autonomic index value, an endocrine index value, a metabolic index value, a stress marker index value, a physical fitness/integrity index determined by the seizure data, and/or other body data to determine a seizure severity index value (SSI value), as described above with respect to FIG. 2. The SSI value may be transmitted/provided to the extreme epileptic event/state detection, quantification and risk determination unit 290, the warning unit 289, the seizure (extreme seizure) ranking unit 247, a memory 217, a database 250/255, a remote device 292, and/or other components of the MD 200. It is noted that in some embodiments the SSI value may be sent directly to the warning unit 289 and/or the seizure (extreme seizure) ranking unit 247 without being sent to the extreme epileptic event/state detection, quantification and risk determination unit 290.

Figure 5B:
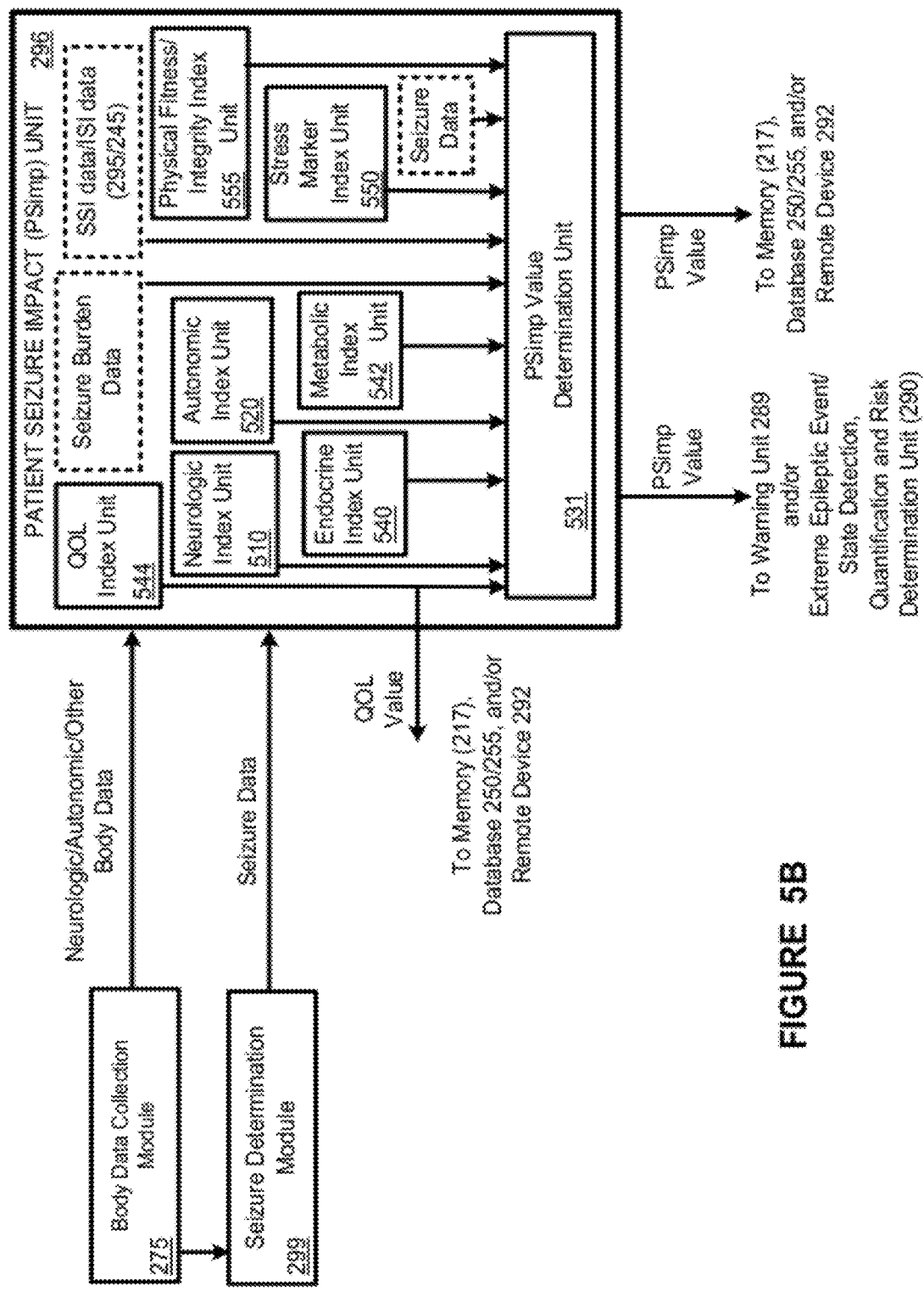
FIG. 5B provides a stylized diagram of a patient impact unit for determining a patient impact using body data and seizure data, in accordance with one illustrative embodiment of the present invention.

Turning now to FIG. 5B, a block diagram depiction of a patient impact unit 296 is provided, in accordance with one illustrative embodiment of the present invention. In one embodiment, the PSimp unit 296 may be adapted to include a seizure severity index (SSI) unit 295 or to use the data from a separate SSI unit 295. The PSimp unit 296 or the PSB unit 273 may receive data from the physical fitness/integrity index unit 555. In one embodiment, body data collection module 275 may send body data to PSimp unit 296. Such body data may include, but is not limited to, neurologic and/or autonomic body data, endocrine data, stress marker data, physical activity data, and/or the like. Likewise, the seizure determination module 299 may send corresponding data to the PSimp unit 296. The PSimp unit 296 may, in one embodiment, comprise a QOL index unit 544. The QOL index unit 544 may provide a QOL index value for use in a PSimp determination, in accordance with one embodiment, or in other embodiments, the QOL index may be computed separately from the PSimp value. The PSimp value determination unit 531 may use seizure burden data, QOL data and/or other body data to determine a patient seizure impact value (PSimp value). The PSimp value may be transmitted/provided to the extreme epileptic event/state detection, quantification and risk determination unit 290, the warning unit 289, a memory (217), a database 250/255, a remote device 292, and/or other components of the MD 200.

Figure 5C:
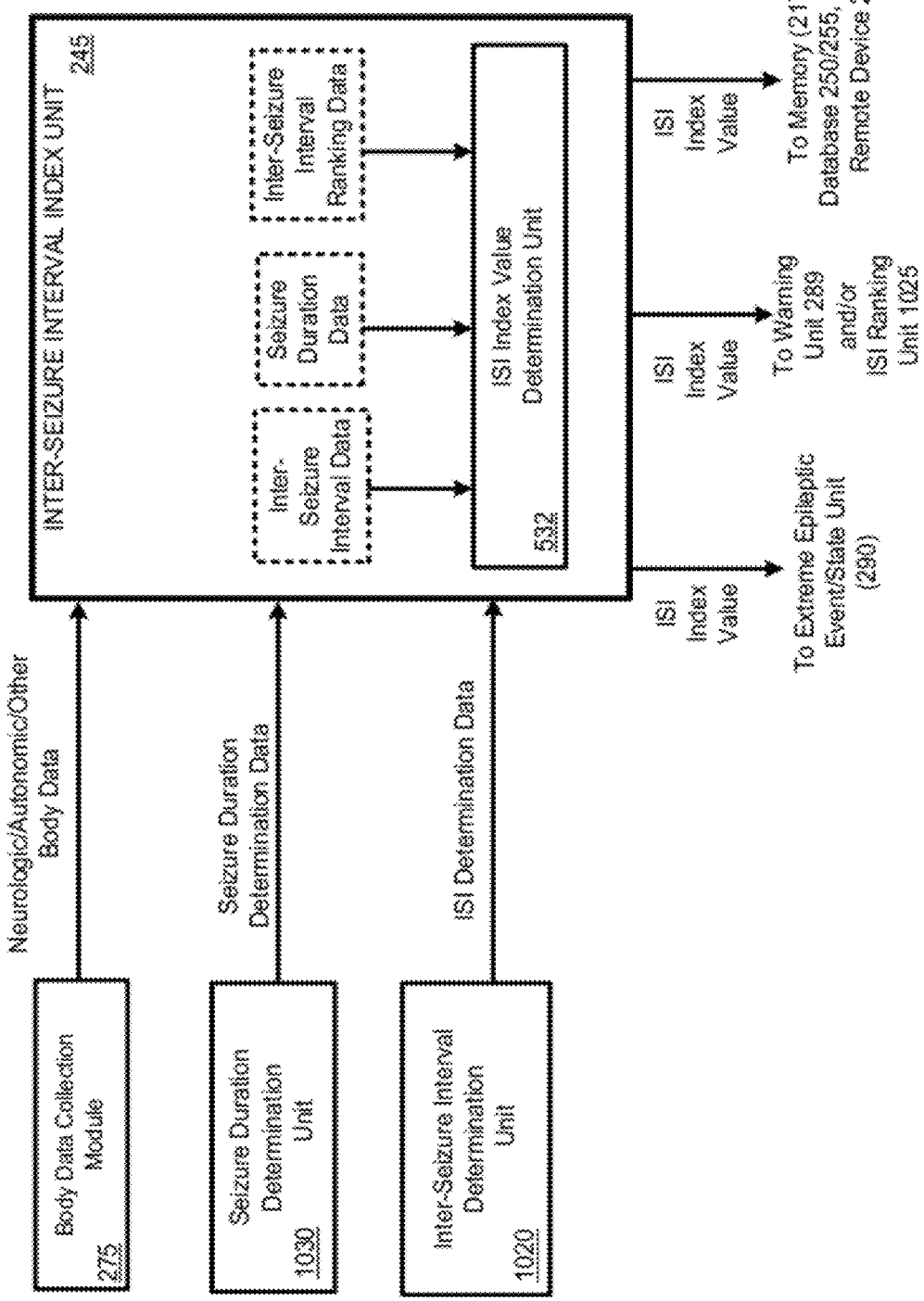
FIG. 5C provides a stylized diagram of an inter-seizure interval index unit for determining a time elapsed between the onset of consecutive or non-consecutive seizures using body data, in accordance with one illustrative embodiment of the present invention.

Turning now to FIG. 5C, a block diagram depiction of an inter-seizure interval index unit 245 (ISI index unit) is provided, in accordance with one illustrative embodiment of the present invention. In one embodiment, the ISI index value determination unit 532 may use a neurologic index value, an autonomic index value, an endocrine index value, a stress marker index value, seizure data and/or other body data to determine an inter-seizure interval index value (ISI index value), as described above with respect to FIG. 2. In one embodiment, the ISI index value may be indicative of extreme seizure events/states if the time interval between two or more seizures is below (by one or more standard deviations) the mean of a normalized distribution of ISIs or at or below the $20^{th}$ percentile of distribution values. The ISI index value may be transmitted/provided to the extreme epileptic event/state detection, quantification and risk determination unit 290, the warning unit 289, the inter-seizure interval ranking unit 1025, a memory (217), a database 250/255, a remote device 292, and/or other components of the MD 200. It is noted that in some embodiments the ISI value may be sent directly to the warning unit 289 and/or the seizure (extreme seizure) ranking unit 247 without being sent to the extreme epileptic event/state detection, quantification and risk determination unit 290.

In one embodiment, the ISI index unit 245 may be adapted to determine an inter-seizure interval (ISI). The ISI index unit 245 may use the time of onset and/or termination of at least two consecutive or non-consecutive seizures from a seizure spread, duration and intensity determination unit 294 to calculate the time elapsed between the seizures. In one embodiment, the ISI index unit 245 may receive data from duration determination unit 1030 (see FIG. 11 below) and inter-seizure interval data from an inter-seizure interval determination unit 1020 (see FIG. 11 below), body data from the body data collection module 275 and/or other seizure data (not shown) in determining the ISI index. In one embodiment, body data collection module 275 may send body data to the ISI index unit 245. Such body data may include, but is not limited to, neurologic and/or autonomic body data, endocrine data, stress marker data, physical activity data, and/or the like. Likewise, the seizure determination module 299 may send seizure data to the ISI index unit 245.

Figure 6:
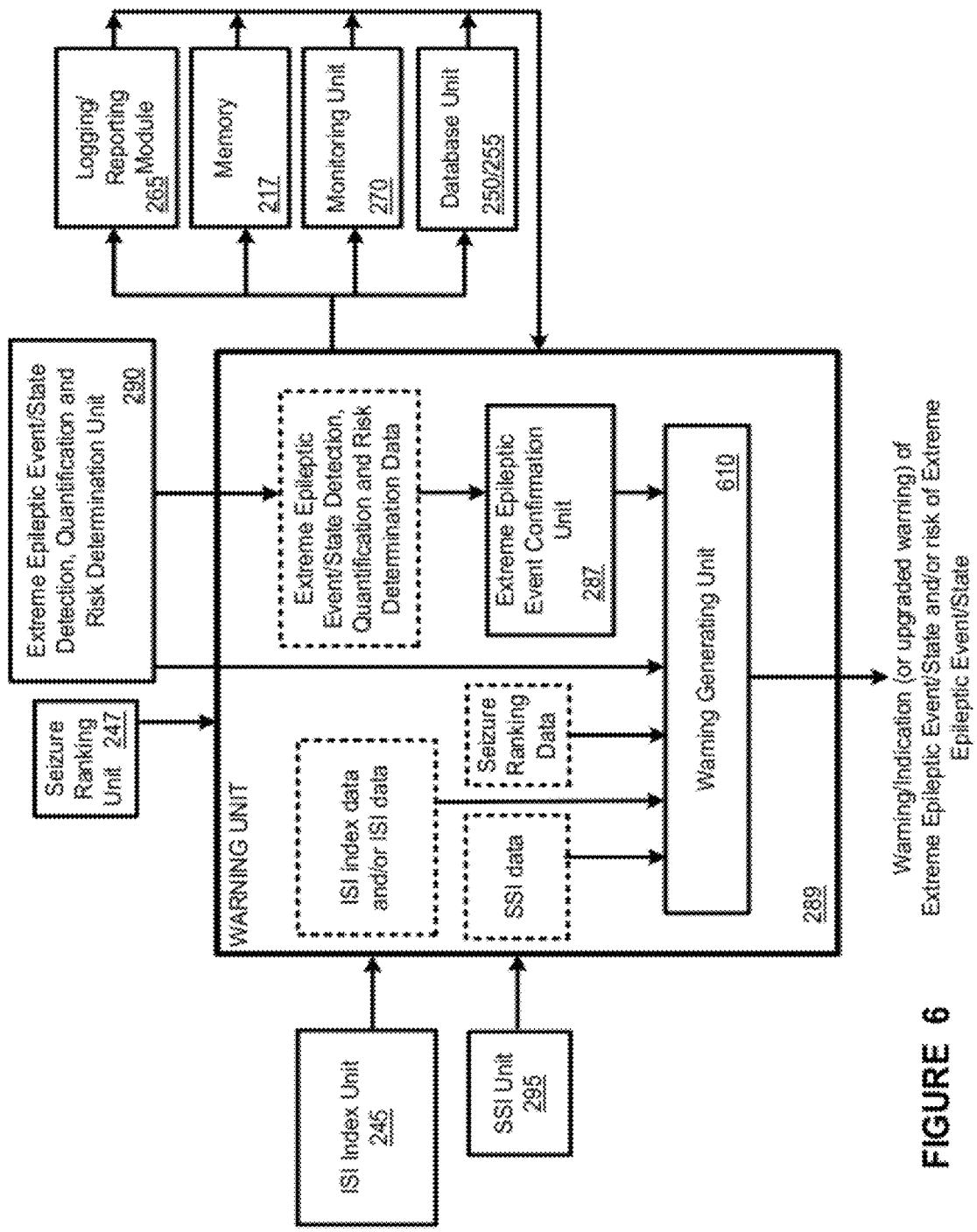
FIG. 6 provides a stylized diagram of a warning unit for warning of a patient's proclivity towards an extreme epileptic event/state or of its occurrence, in accordance with one illustrative embodiment of the present invention.

Turning now to FIG. 6, a block diagram depiction of a warning unit 289 is provided, in accordance with one illustrative embodiment of the present invention. In one embodiment, the warning unit 289 may be adapted to provide a warning of a seizure, seizure events and/or extreme seizure events. In various embodiments, extreme seizure events may include a present or past state of status epilepticus, an increased risk of status epilepticus, a risk of SUDEP associated with a seizure, an increased risk of SUDEP associated with a seizure, the occurrence of injury or of an increased risk of injury and/or the like. The warning unit 289 may provide a warning to a patient, a physician, a caregiver, the logging/reporting module 265, the monitoring unit 270, the remote device 292, the memory 217, the database 250/255, and/or the like.

The warning unit 289 may include a warning generating unit 610, in accordance with one embodiment. The warning unit 289 may be adapted to receive SSI data from the SSI Unit 295, ISI data from the ISI Index Unit 245, PISI data from the (post-ictal determination unit 1033), physical fitness/physical integrity data from the physical fitness/integrity index unit 555, PSimp data from the PSimp unit 296, extreme epileptic event/state data from extreme epileptic event/state detection, quantification and risk determination unit 290, and/or extreme seizure event confirmation data from extreme epileptic event confirmation unit 287. In various embodiments, the warning unit 289 may be adapted to receive other signals and/or data in addition to, or alternatively to, the aforementioned data, as shown in FIG. 6. In one embodiment, the warning generating unit 610 may take any data received by the warning unit 289 as an input to generate a warning. The warning may be a general warning related to a seizure or extreme seizure event or state such as status epilepticus, an upgrade in warning of an existing extreme seizure state/event, or related to an injury associated with a seizure (e.g., which prolongs the time the patient is immobile or in the recumbent position beyond a mean, median or percentile time for that patient). In one embodiment, the warning unit 289 may include an extreme epileptic event confirmation unit 287. The extreme epileptic event confirmation unit 287 may take data from the extreme epileptic event/state detection, quantification and risk determination unit 290 and confirm or verify that an extreme epileptic event/state is likely, is about to occur, is occurring or has occurred. If the extreme event/state is confirmed by the extreme epileptic event/state determination unit 287, the confirmation may be sent to the warning generating unit 610, and the warning may proceed. If the extreme event/state is not confirmed by the extreme epileptic event/state determination unit 287, the warning may be blocked or disabled, and data associated with the blocked/disabled warning may be removed from the logging/reporting module 265, the monitoring unit 270, the remote device 292, the memory 217, the database 250/255, and/or the like.

Warnings may include sounds or lights, automated emails, text messages, telephone calls, or video messages sent from the MD 200, either directly or via a monitoring unit 270, to the police, an EMT unit, the patient's physician/caregiver's cellular telephone, PDA, computer 150, television, etc. Such warning(s) may allow the patient and/or caregivers to take measures protective of the patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc. The warning may, when appropriate, automatically disable operation of a vehicle or of power equipment or inflate a life saver (e.g., for a patient who is swimming) or bags placed on the chest or back of a patient to minimize risk of injury in case of falls.

Figure 7:
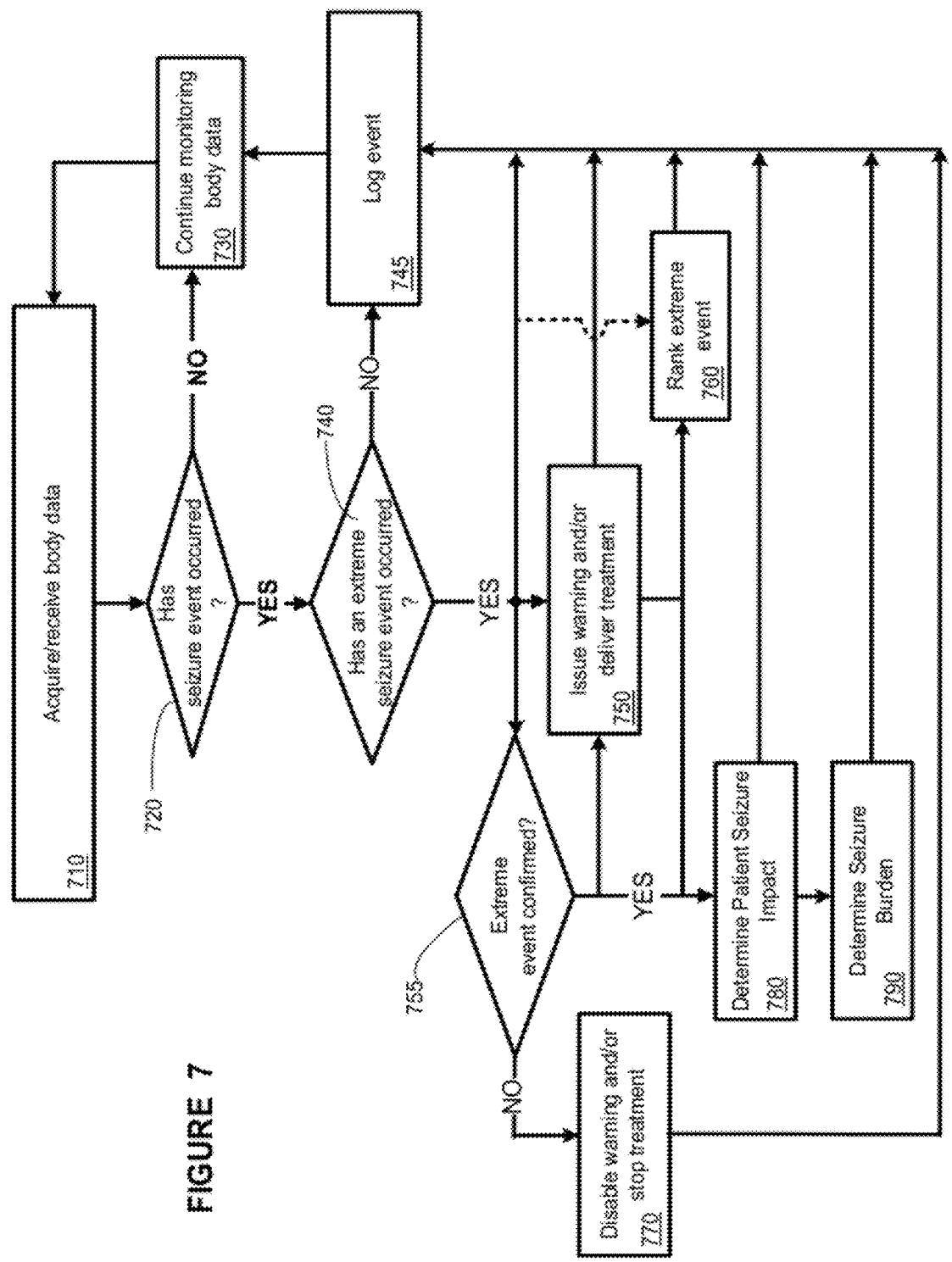
FIG. 7 provides a flowchart depiction of a method for identifying and/or managing an extreme epileptic event/state, in accordance with one illustrative embodiment of the present invention.

Turning now to FIG. 7, a flowchart depiction of a method for taking action (e.g., warning, providing treatment/therapy, logging, etc.) in response to the occurrence of a seizure event and/or an extreme seizure event is provided, in accordance with one illustrative embodiment of the present invention. The MD acquires and/or receives body data at step 710, typically from the body data collection unit 275 which buffers, amplifies/conditions and performs A/D conversion of the body data. Using data from unit 275, the seizure determination module 299 in the MD 200 determines, through operations including but not limited to calculations based on at least one index, if a seizure event has occurred, is likely to occur or is occurring (step 720). If the MD 200 determines that no seizure or seizure event has occurred, the IMD 200 will continue to monitor for body data (step 730; return the flow to step 710).

If the medical device determines (at step 720) that a seizure event has occurred or is occurring or is likely to occur, based on at least one of an autonomic index, a neurologic index, a stress marker index, a metabolic index and/or an endocrine index (e.g., using an SSI unit 295, an ISI index unit 245, a PSimp unit 296 and/or another unit/module in the MD 200), the subsequent step 740 may be to determine, e.g., using unit 290, if the event is extreme. Determination that the event is extreme, may trigger responsive actions (step 750) including but not limited to delivering a therapy or therapies, (unit 220), warning(s) (unit 289) and requesting confirmation via unit 287 that the event is extreme (step 755), and if it is deemed extreme, it may be then ranked (step 760), typically using unit 247. If the event is not confirmed as extreme, all responsive actions may be terminated (step 770). At any given step, information yielded by that step, and the decisions made based on this information, may be send to logging/reporting unit 265 (step 745) and/or to memory 217. Steps 750, 760 and 770 may begin at the same time and end at the same time (or at different times) according to various embodiments. Further, it is contemplated that events may be logged after a determination and/or confirmation of an extreme event (steps 740/755) has occurred.

The number of steps and the order in which they are adopted may vary according to one of several possible embodiment contemplated herein. For example, confirmation that the event is extreme may be unnecessary if all indices (autonomic, neurologic, endocrine, metabolic, tissue stress marker, physical integrity, etc.) are determined simultaneously. However, if all indices are not measured, those untested may be determined in any number and/or temporal sequence for the purpose of confirmation. The medical device 200 may determine an SSI value using at least one of an autonomic index, a neurologic index, a stress marker index, a metabolic index and/or an endocrine index; the medical device 200 may determine an inter-seizure interval index (ISI index) value using at least one of an autonomic index, a neurologic index, a stress marker index, a metabolic index and/or an endocrine index; the medical device 200 may determine a physical fitness/integrity index value using at least one of an autonomic index, a neurologic index, a stress marker index, a metabolic index and/or an endocrine index. Typically, the SSI value is determined by SSI unit 295 (which may comprise an SSI determination unit (530)). Typically, the ISI index value is determined by ISI index unit 245. Typically, the physical fitness/integrity index value is determined by physical fitness/integrity index unit 355. In one or more embodiments, additional data may also be used to determine the ISI index value and/or physical fitness/integrity index value. Depending upon the embodiment, one or more of the SSI value, the ISI index value and/or the physical fitness/integrity index value may be determined. For example, in one embodiment, only the SSI value may be calculated while the ISI index value is not calculated. In another embodiment, only the ISI index value may be calculated while the SSI value is not calculated. In one or more embodiments, additional data may also be used to determine the SSI values, ISI values and/or physical fitness/integrity index values.

The confirmation of an extreme epileptic event/state parameter(s) may be performed by an extreme epileptic event/state confirmation unit 287 (at step 755). The confirmation of an extreme epileptic event/state may be based upon one or more SSI values and/or one or more ISI index values as described above, and/or be based upon other data/indices as described above. From step 755, the flow may proceed to determining a patient seizure impact (PSimp) value (step 780), and in some embodiments, the flow may then proceed to determining a seizure burden value (step 790). The medical device 200 may determine a PSimp value using at least one of an autonomic index, a neurologic index, a stress marker index, a metabolic index and/or an endocrine index, a quality of life index or a physical fitness/integrity index and or the like (step 780). The medical device 200 may determine a seizure burden value using at least one of an autonomic index, a neurologic index, a stress marker index, a metabolic index and/or an endocrine index and/or the like (step 790). Other procedures/modules may be used to determine a seizure burden and/or patient seizure impact. For example, an Acquire/Determine Physical Fitness Index/Body Integrity Unit (not shown) may use these data to determine seizure burden and/or patient seizure impact. The MD 200 may also take responsive action for extreme epileptic event/state (at step 750) that may include, but is not limited to, drug/chemical therapy, electric stimulation, cooling, supportive care, oxygen administration, warning, logging/reporting, and/or the like. It is also contemplated that a patient's physical activity may be stored in a memory 217 or logged/reported in one or more of the database 250/255 and the remote device 292.

Figure 8:
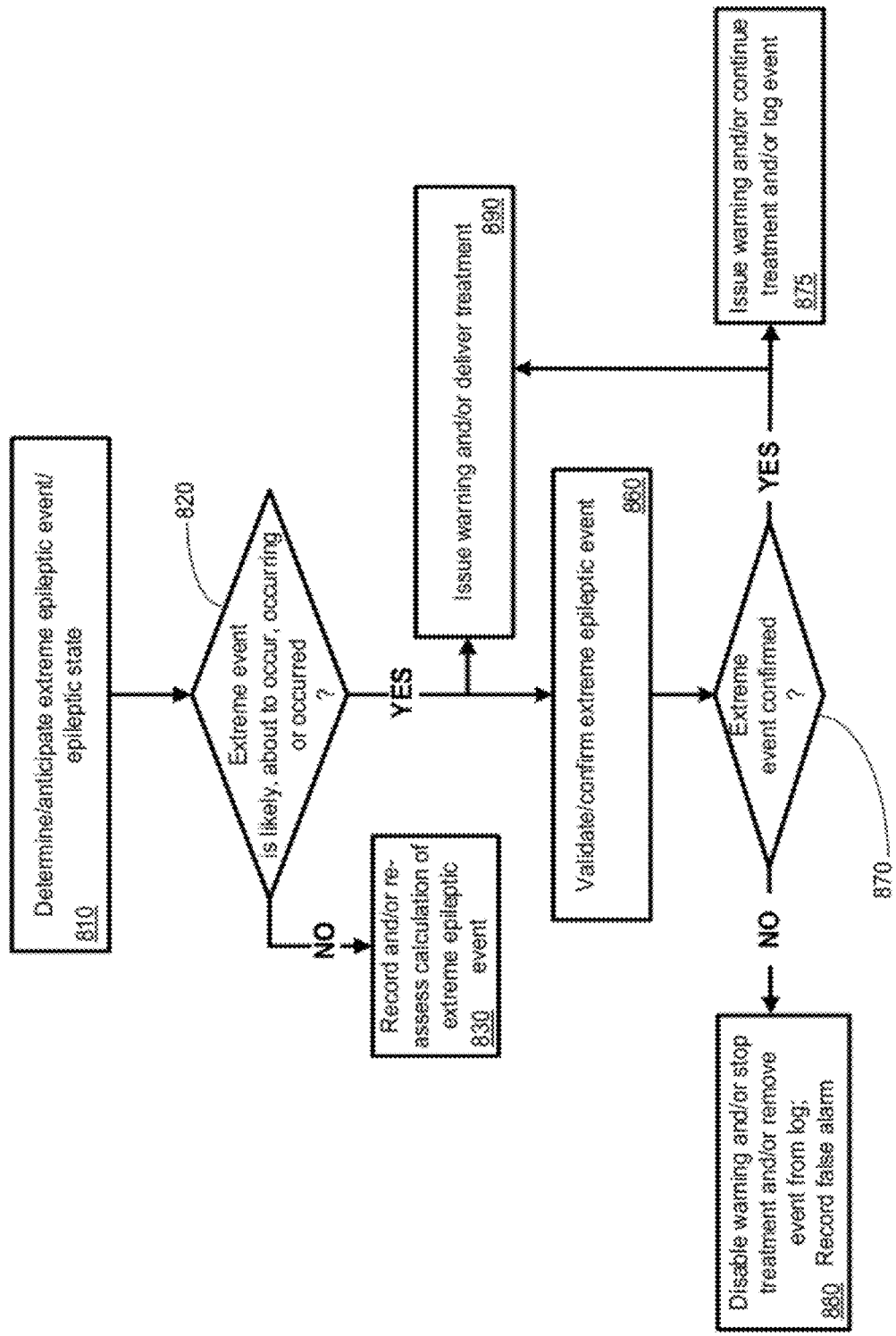
FIG. 8 provides a flowchart depiction of a method implementing responsive actions (warning, treatment, data logging among others) in response to determining that an extreme epileptic event/state is probable, is occurring or has occurred, in accordance with one illustrative embodiment of the present invention.

Turning now to FIG. 8, details of the steps in FIG. 7 that are implemented when an extreme event is likely to occur, about to occur, is occurring or has occurred are provided, is depicted in accordance with one or more illustrative embodiments. The MD 200 may issue a warning or take action (step 890) based upon detection of an extreme epileptic event/state in a patient (steps 810/820). It should be noted that in some embodiments an extreme epileptic event is the occurrence of an actual extreme epileptic seizure or condition, while in other embodiments the extreme epileptic event is an elevated risk of an extreme epileptic seizure or condition. If the MD 200 determines a patient is not in an extreme epileptic event/state (step 820), the MD 200 may proceed to record the current condition of the patient and reassess calculation(s) of extreme epileptic event/state data (830). If the MD 200 determines a patient is in an extreme epileptic event/state (step 820), the MD 200 may in some embodiments perform an extreme epileptic event confirmation (step 860). If the MD 200 determines a patient is in an extreme epileptic event/state (step 820), the MD 200 may, in one embodiment, issue a warning and/or deliver treatment to the patient (step 890).

In one embodiment, the MD 200 may delay warning the patient until the extreme seizure event confirmation is confirmed (step 860). It is contemplated that steps 860 and 890 may occur at the same time or at different times in various embodiments described herein. If the MD 200 determines an extreme seizure event confirmation has not occurred (870), the MD 200 records and/or logs a tentative and/or potential false positive event, e.g., by recording the original detection as erroneous or unconfirmed (step 880), if this determination has not been based on all indices disclosed in this invention. In the case that all disclosed indices have not been used for said determination, one or more indices not used in issuing a "false positive" decision may be measured and depending on the results of the more comprehensive analysis, the decision ("false positive") may be confirmed or rejected. If a false positive event is issued, the medical device 200 may also disable (at least transiently) an issued warning and/or stop treatment and/or remove an event from the log (step 880). If a false positive event is confirmed, this outcome may be recorded and/or logged in a logging/reporting module 265 (step 880). If the false positive event is rejected, an extreme event detection may be re-issued and all responsive actions will be re-instituted according to the embodiments of this invention (e.g., steps 870, 890).

Figure 9:
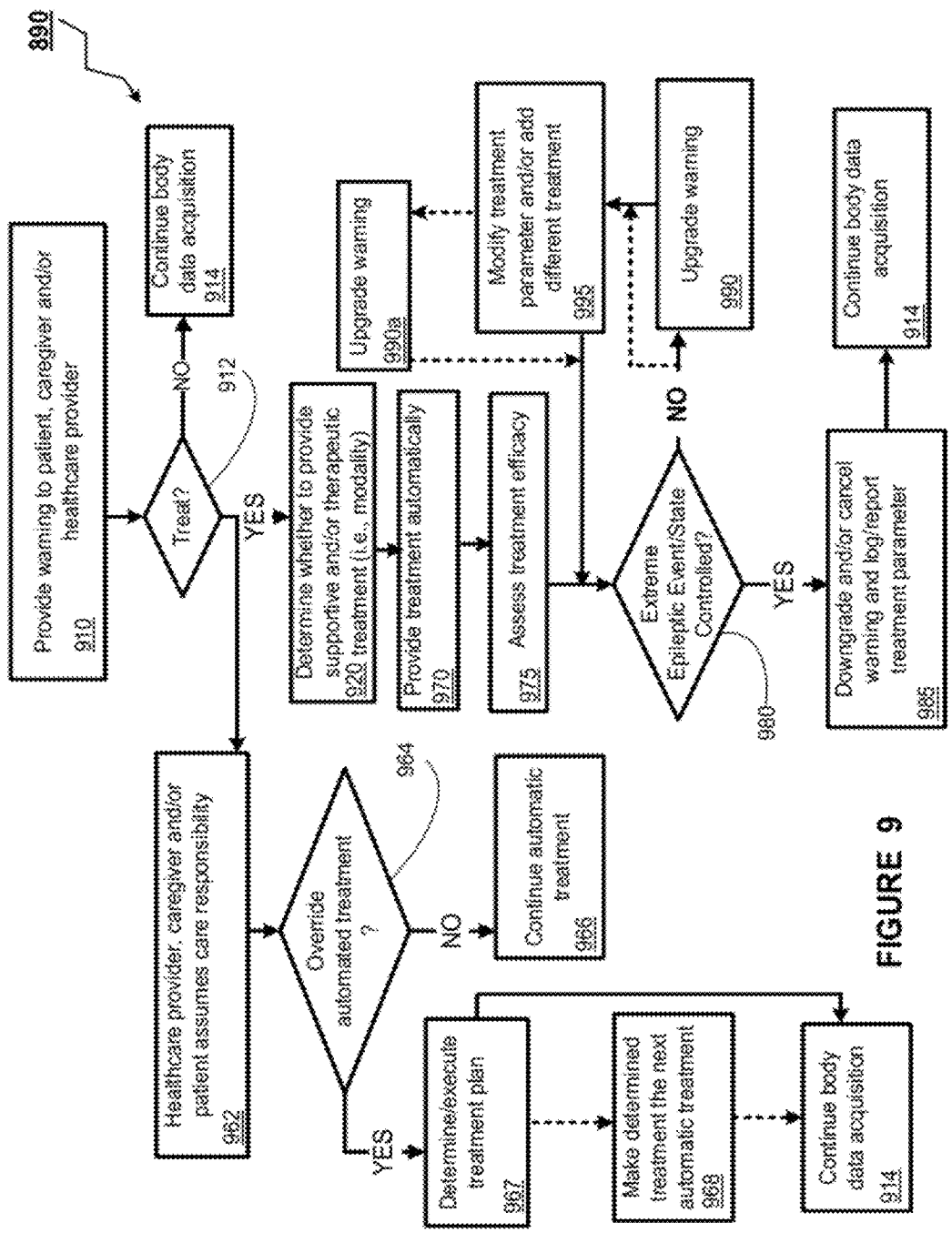
FIG. 9 provides a flowchart depiction of a method for warning and/or providing a treatment to a patient likely to be in, or to recently have been in an extreme epileptic event/state, in accordance with one illustrative embodiment of the present invention.

Turning now to FIG. 9, a flowchart depiction of a method for warning and/or providing a treatment to a patient in response to an extreme seizure event is provided, in accordance with one illustrative embodiment. The MD 200 may provide a warning of a state of an extreme epileptic event/state via the warning unit 289 in one or more embodiments (step 910). The warning may be to a patient, a physician, a caregiver, emergency response personnel, a logging/reporting module 265, a monitoring unit 270, a remote device 292, an external entity 265 and/or the like. The warning may indicate an extreme epileptic event/state (e.g., a severe seizure, status epilepticus, or an injury resulting from an otherwise non-extreme seizure). At step 912, the decision is made whether or not to treat the patient based upon the warning from step 910. If it is determined that no treatment will be performed, the flow proceeds to step 914 where patient monitoring and body data acquisition continues. If it is determined that treatment will be administered, the flow may proceed to one or both of steps 920 and/or 962.

A determination may be made as to which treatment modality(ies) are to be provided to a patient (step 920). Modalities include, but are not limited to, electrical currents, chemical/drug therapies and/or supportive treatments such as cooling, fluids, pressor agents and/or oxygen. In one embodiment, the MD 200 may automatically implement a predetermined treatment to reduce the risk of an extreme epileptic event/state and/or to reduce the effects of a state of an extreme epileptic event/state in the patient (step 970) using one or more treatment modalities. In reference to supportive care, seizures are powerful biological stressors and inductors of stress markers and may deplete the body of certain antioxidants such as glutathione peroxidase. The concentration of certain compounds that protect from biological stress (e.g., dehydroepiandrosterone or its sulfate conjugate, glutathione peroxidase and/or the like) or the body's total antioxidant capacity may be measured to determine if it is adequate, and if not, to increase it using available antioxidants to preserve the integrity of organs/functions so as to stall disease progression. Stress marker index indices and antioxidants may be measured in brain (invasively and/or non-invasively), CSF, plasma, serum, erythrocytes, urine, and saliva (e.g., alpha amylase).

Upon delivery of automatic treatment(s), an assessment of the efficacy of the treatment may be performed (step 975) in some embodiments. Based upon the assessment of the efficacy of treatment, a determination is made whether the state of the extreme epileptic event/state is at least substantially controlled (step 980). If a determination is made that the extreme epileptic event/state is not substantially controlled (step 980), the MD 200 may upgrade the warning to a more severe level (step 990) and the treatment being delivered may be modified, and/or an additional treatment may be provided (step 995). In an alternative embodiment, the step of upgrading the warning may be initially omitted and the treatment may be modified first, as indicated by the dotted line connecting blocks 980 and 995 and 990*a*. The MD 200 may then continue to determine whether the state of the status epilepticus is substantially controlled (step 980).

Upon a determination that the extreme event/state is substantially controlled (step 980), the warning may be downgraded and/or canceled (step 985). Further, the treatment parameter(s) used for the administration of the automatic treatment may be reported/logged (step 985). The MD 200 may then continue to perform body data acquisition (step 914).

In one embodiment, upon providing a warning to the patient, caregiver, and/or to a healthcare provider (step 910), the MD 200 may provide for the healthcare provider, the caregiver, and/or the patient to assume care/treatment responsibilities (step 962). Based upon one or more inputs received by the MD 200, a determination may be made as to whether to override the automated treatment (step 964). If it is determined that the automated treatment is not to be overridden, then the state of the automatic treatment is maintained (step 966).

If a determination is made that the automated treatment is to be overridden, a non-automated treatment plan is determined and executed (step 967). A more detailed description of the determining and executing a non-automated treatment plan is provided in FIG. 10 and accompanying description below. In one embodiment, upon determining and executing a non-automated treatment plan, this treatment plan may be set as the next automatic treatment that is executed by the MD 200 (step 968). The MD 200 then continues to perform body data acquisition (step 914). In an alternative embodiment, the step of setting the non-automatic treatment plan as the default automatic treatment plan may be omitted, as indicated by the dotted lines between blocks 967, 968 and 969.

Figure 10:
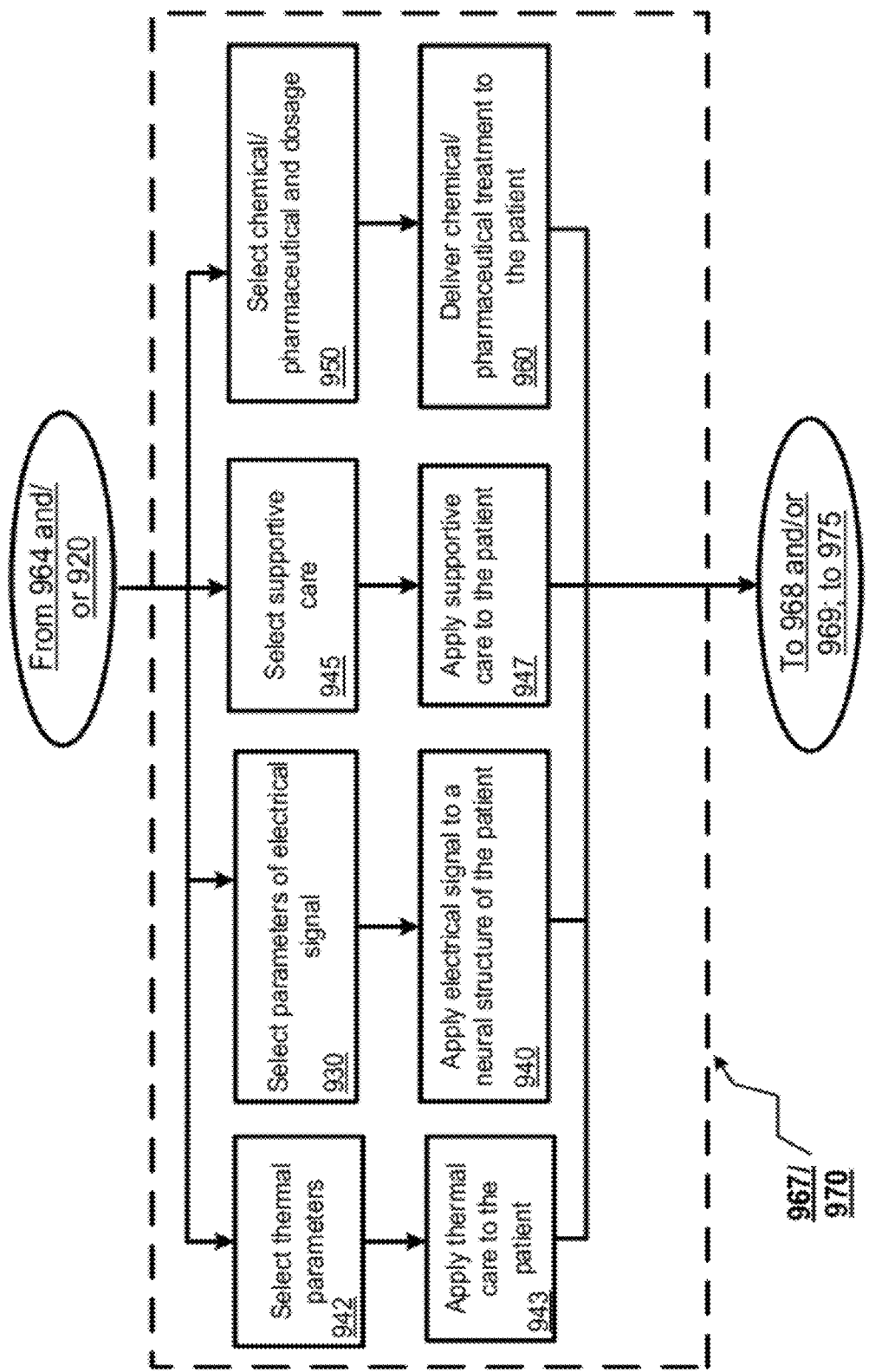
FIG. 10 illustrates a stylized diagram of determining and executing a treatment plan by a healthcare provider, caregiver and/or patient subsequent to overriding automated treatment an extreme epileptic event/state, in accordance with one illustrative embodiment of the present invention.

Turning now to FIG. 10, a stylized depiction of the step of determining an automatic or a non-automatic treatment plan of steps 967/970 of FIG. 9, in accordance with one illustrative embodiment, is provided. The MD 200 may select a chemical/drug the dosage and rate of delivery (step 950) and deliver the drug/chemical to the patient (step 960). In addition to, or alternatively to, the chemical treatment, the MD 200 may select parameters of an electrical signal to treat the patient (step 930) and apply the specified electrical signal to a neural structure (e.g., a branch of the vagus nerve) of the patient (step 940). Further, in addition, or alternatively, the MD 200 may select one or more thermal parameters to specifically treat the extreme event/state with a thermal therapy (heating and/or cooling) (step 942) and apply it (step 943). The flow may then proceed to steps 968/969 and/or step 975. Further, in addition, or alternatively, the MD 200 may select one or more supportive care steps to treat the patient (step 945) and apply the specified supportive care (step 947).

Figure 11:
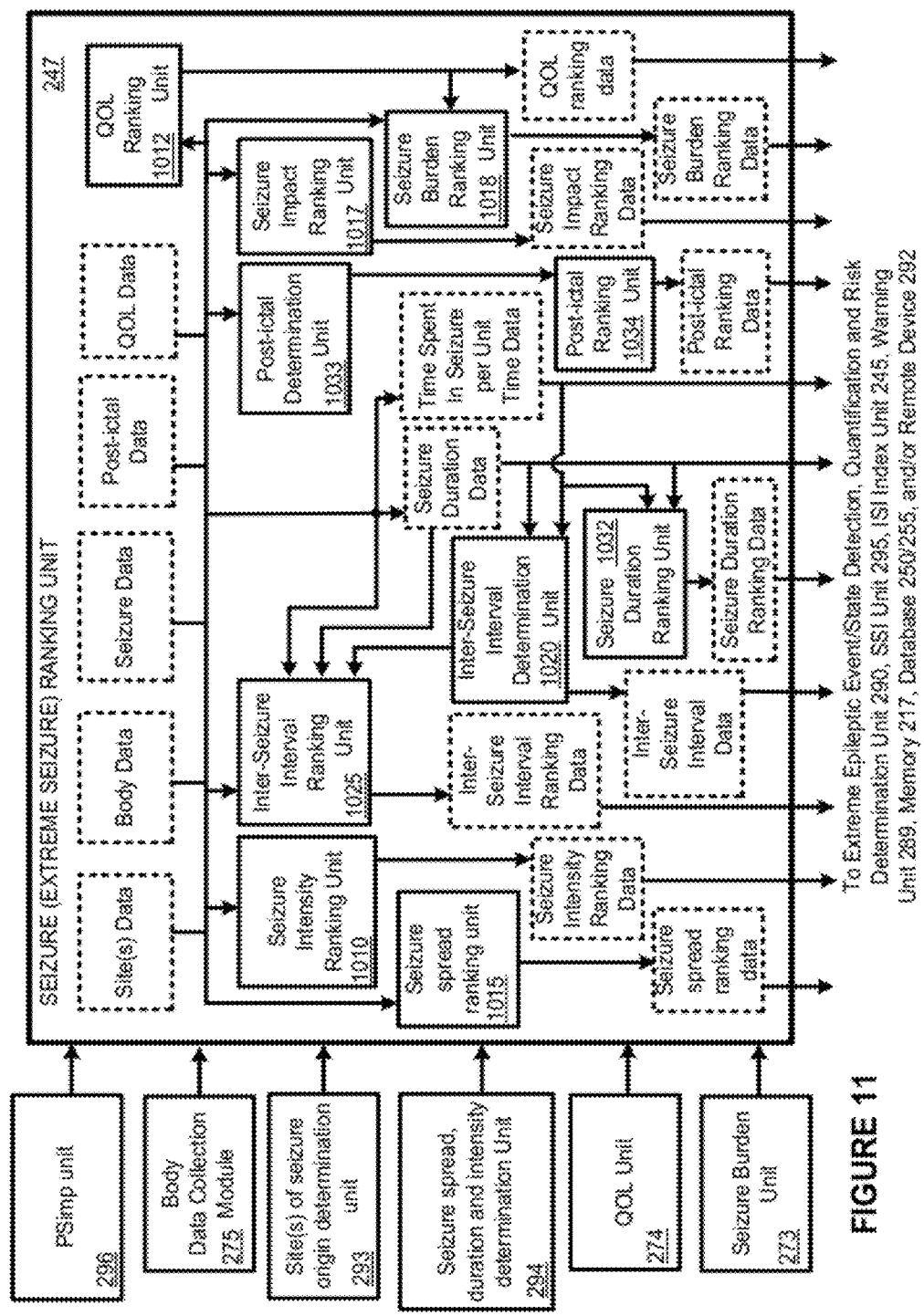
FIG. 11 provides a stylized diagram of a seizure impact ranking unit adapted to quantify seizure impact based on its effects (type, magnitude and duration) on neurologic, autonomic, metabolic, endocrine, and/or physical integrity (e.g., damage to musculoskeletal system), tissue stress markers and/or time spent in seizure per unit time using body data, in accordance with one illustrative embodiment of the present invention.

Turning now to FIG. 11, a block diagram depiction of a seizure (or extreme seizure) ranking unit 247 is provided, in accordance with one illustrative embodiment. Rankings reduce in-depth measures to a sequence of ordinal numbers, thus facilitating the evaluation of complex information according to certain criteria. Rankings, in embodiments described herein, may be done according to one or more of a so-called standard completion, modified, ordinal, dense or fractional ranking. Those skilled in the art having the benefit of this disclosure would appreciate the approach to ranking described herein, is applicable to the ranking of any measure or index in this invention.

In one embodiment, the seizure (extreme seizure) ranking unit 247 may rank events classified as extreme using data from the extreme epileptic event/state detection, quantification and risk determination unit 290 and may provide the rankings to the memory (217), database 250/255, and/or remote device 292. In various embodiments, the seizure (extreme seizure) ranking unit, may receive data directly from, for example, the SSI unit 295, ISI unit 245, PSimp unit 296, the seizure spread duration and intensity determination unit 293, and/or the like, about seizure intensity data, seizure intensity rankings, inter-seizure interval data, inter-seizure interval ranking data, seizure duration data, time spent in seizure data, and/or the like. Seizure ranking unit 247 may also receive data from memory (217), database 250/255, and/or remote device 292. In one or more embodiments, the output of the seizure (extreme seizure) ranking unit 247 may be an indication of a seizure ranking as compared to historical seizure rankings and/or one or more reference values. This may be accomplished by first determining if an SSI and/or an ISI value are near, at, or outside the boundaries between extreme and non-extreme values. If an event fulfills the criteria to be classified as extreme, it is ranked relative to other extreme events, and the warning, treatment, etc., are upgraded based on said ranking (e.g., said event ranks above the $60^{th}$ percentile for SSI and below the $40^{th}$ percentile for ISI). For a normalized distribution the upgrade may take place if the extreme event is for example, one SD to the right of the mean or median for SSI and one SD to the left of the mean or median for ISI. It is contemplated that other percentile ranking values may be used.

The seizure (extreme seizure) ranking unit 247 may include a seizure intensity ranking unit 1010, in accordance with one or more embodiments. The seizure intensity ranking unit 1010 may be adapted to receive body data from body data collection module 275, site(s) data from the site(s) of seizure origin determination unit 293, seizure spread/intensity/duration data from seizure spread, duration and intensity determination unit 294, SSI data from the SSI unit 295 and/or other data from various components of the MD 200 and/or the seizure (extreme seizure) ranking unit 247. It should be noted that these determinations of intensity recited herein are not exclusive, and the determination of seizure intensity data using other body data is also contemplated, as would be evident to one of skill in the art having the benefit of this disclosure. Seizure intensity data may be determined from site(s) of seizure origin data and/or at each site (brain and/or body) to where the seizure spreads or is manifested, whether directly or indirectly. In one embodiment, the seizure intensity ranking unit 1010 may determine seizure intensity data based upon data measurements over a period of time or body data as a function of time (as discussed in further detail below with respect to FIGS. 14-15). In other embodiments, the seizure intensity ranking unit 1010 may determine seizure intensity data based only on one of intensity, duration or extent of spread. That is, intensity, duration and extent of spread may be ranked separately from SSI by the seizure (extreme seizure) ranking unit 247. This approach allows classification of any of these three metrics as extreme, even if a composite measure incorporating all three (e.g., SSI=(percentile intensity+percentile duration+percentile spread)/3) may not be extreme. This may allow for better anticipation and for prevention of extreme epileptic events by allowing seizures to be classified as extreme based on one of the three metrics alone, even though the SSI may not be extreme based on two or more of them. Similarly, it may be advantageous to issue a certain kind of warning (different than the warning for an extreme SSI) and deliver a therapy in this instance. As such, it may be noted that there are: 1) extreme intensity and/or duration and/or spread; and/or 2) extreme events/states when the SSI is extreme. In various embodiments, seizure intensity data may be logged/reported in logging/reporting module 265, transmitted to the extreme epileptic event/state detection, quantification and risk determination unit 290, the SSI unit 295, the memory 217, the remote device 292 and/or the database 250/255, as described above in FIG. 2.

The seizure (extreme seizure) ranking unit 247 may include a seizure duration ranking unit 1032, in accordance with one or more embodiments. The seizure duration ranking unit 1032 may be adapted to receive body data from body data collection module 275 site(s) data from the site(s) of seizure origin determination unit 293, seizure spread/intensity/duration data from seizure spread, duration and intensity determination unit 294 and/or other data from various components of the MD 200. The seizure duration ranking unit 1032 may be adapted to determine seizure ranking data which may include the ranking of a patient's seizure event with respect to a reference value and/or compared with past seizure/extreme seizure events/states. In further embodiments, the rank of the duration of a seizure event may be based on other criteria as would be apparent to one of skill in the art having the benefit of this disclosure. The seizure duration ranking unit 1032 may also be adapted to determine a seizure duration ranking over a given time period; such a determination may include comparing one or more seizure events occurring within the time period (discussed in further detail below with respect to FIG. 13). The time periods may be of a fixed duration or may be of dynamic duration; likewise, the time period may be a fixed window or a rolling window.

The seizure (extreme seizure) ranking unit 247 may include a seizure spread ranking unit 1015, in accordance with one or more embodiments. The seizure spread ranking unit 1015 may be adapted to receive body data from body data collection module 275 site(s) data from the site(s) of seizure origin determination unit 293, seizure spread/intensity/duration data from seizure spread, duration and intensity determination unit 294 (described above) and/or other data from various components of the MD 200. The seizure spread ranking unit 1015 may be adapted to determine a seizure spread ranking, i.e., a relative determination of a seizure spread relationship to past values. In one embodiment, for example, the seizure spread ranking may be based upon a normal/normalized distribution of seizure spread values. The spread of seizure events may be determined based upon body data, site(s) data and/or spread data values relative to adjustable or pre-determined thresholds, responsiveness and/or/awareness of a patient, and/or the like. In various embodiments, seizure spread rankings may be logged/reported in logging/reporting module 265 and/or transmitted to the extreme epileptic event/state detection, quantification and risk determination unit 290, the SSI unit 295, memory 217 and/or database 250/255, as described above with respect to FIG. 2.

The seizure (extreme seizure) ranking unit 247 may include an inter-seizure interval ranking unit 1025, in accordance with one or more embodiments. The inter-seizure interval ranking unit 1025 may be adapted to receive ISI data from the ISI determination unit 1020 (described below), body data from body data collection module 275, site(s) data from the site(s) of seizure origin determination unit 293, seizure spread/intensity/duration data from seizure spread, duration and intensity determination unit 294 and/or other data from various components of the MD 200. The inter-seizure interval ranking unit 1025 may be adapted to determine an inter-seizure interval ranking, i.e., a relative determination of a seizure interval relationship to past interval values. In one embodiment, for example, the inter-seizure interval ranking may be based upon a normal/normalized distribution of seizure interval values. The beginnings and ends of seizure events may be determined based upon body data, site(s) data and/or spread data values relative to dynamic or pre-determined thresholds, responsiveness of a patient, and/or the like. In various embodiments, inter-seizure interval rankings may be logged/reported in logging/reporting module 265 and/or transmitted to the extreme epileptic event/state detection, quantification and risk determination unit 290, the SSI unit 295, memory 217 and/or database 250/255, as described above with respect to FIG. 2.

The seizure (extreme seizure) ranking unit 247 may include an inter-seizure interval ISI) determination unit 1020, in accordance with one or more embodiments. The inter-seizure interval determination unit 1020 may be adapted to receive body data from body data collection module 275, site(s) data from the site(s) of seizure origin determination unit 293, seizure spread/duration/intensity data from seizure spread, duration and intensity determination unit 294, ISI data from the ISI index unit 245 and/or other data from various components of the MD 200. The inter-seizure interval determination unit 1020 may be adapted to determine an inter-seizure interval (ISI), i.e., a time period between seizure events. In one embodiment, the inter-seizure interval may be measured from the end of one seizure event to the beginning of the next seizure event. In another embodiment, the inter-seizure interval may be measured from the onset of a first seizure to the onset of a second seizure. The beginnings and ends of seizure events may be determined based upon body data, site(s) data and/or spread data values relative to adjustable or pre-determined thresholds, responsiveness/awareness of a patient, and/or the like. In various embodiments, inter-seizure interval data may be logged/reported in logging/reporting module 265 and/or transmitted to the ISI ranking unit 1025, the extreme epileptic event/state detection, quantification and risk determination unit 290, the SSI unit 295, memory 217 and/or database 250/255 as shown above with respect to FIG. 2. In one or more embodiments, an epileptic event may be classified as extreme based upon on the ISI, or based upon the ISI in addition to other values described herein.

In various embodiments, seizure duration data, seizure ranking data and/or the time spent in seizure data may be logged/reported in logging/reporting module 265 and/or transmitted to the extreme epileptic event/state detection, quantification and risk determination unit 290, the SSI unit 295, memory 217 and/or database 250/255 as described above with respect to FIG. 2.

The seizure (extreme seizure) ranking unit 247 may include a post-ictal ranking unit 1034, in accordance with one or more embodiments. The post-ictal ranking unit 1034 may be adapted to receive post-ictal data from post-ictal determination unit 1033, body data from body data collection module 275 site(s) data from the site(s) of seizure origin determination unit 293, seizure spread/duration/intensity data from seizure spread, duration and intensity determination unit 294 and/or other data from various components of the MD 200. The post-ictal ranking unit 1034 may be adapted to determine post-ictal ranking data which may include the ranking of a patient's post-ictal state with respect to a reference value and/or compared with past post-ictal states. In further embodiments, the rank of the post-ictal state of a seizure event may be based on other criteria as would be apparent to one of skill in the art having the benefit of this disclosure. The post-ictal ranking unit 1034 may also be adapted to determine a post-ictal ranking over a given time period; such a determination may include comparing one or more seizure events occurring within the time period (discussed in further detail below with respect to FIG. 13). The time periods may be of a fixed or a dynamic duration; likewise, the time period may be a fixed window or a rolling window.

The seizure (extreme seizure) ranking unit 247 may include a post-ictal determination unit 1033. In one embodiment, the post-ictal state may be defined as the state in which the values of any of the indices disclosed herein are different from those observed in the inter-ictal and ictal states. The post-ictal determination unit 1033 may be adapted to receive body data from body data collection module 275 site(s) data from the site(s) of seizure origin determination unit 293, seizure spread/duration/intensity data from seizure spread, duration and intensity determination unit 294 and/or other data from various components of the MD 200. In accordance with one embodiment, the post-ictal determination unit 1033 may determine the duration of a post-ictal state of a patient. The post-ictal index determination 1033 may also determine a severity of the post-ictal state based upon the magnitude and/or duration and or spread of the post-ictal state, as well as the rate of change into and out of a post-ictal state, in manners similar to those used in the described embodiments herein for determining SSI. In one embodiment, the magnitude of the post-ictal state may be measured as the area below a lower threshold and above the curve graphically representing a seizure parameter (see, e.g., FIGS. 14B/17B and accompanying descriptions). The post-ictal index determination 1033 may make such determinations based upon body data information, external indications, and/or other data that would become apparent to one of skill in the art having the benefit of this disclosure. A prolonged and/or an increased duration and/or magnitude of the post-ictal state may be indicative of a severity of a seizure event experienced by a patient and used to classify an event as extreme or non-extreme. Moreover, continued increases in post-ictal state duration and/or magnitude may be indicative of a patient's having a risk/increased risk of an extreme seizure event and/or a patient having an extreme seizure event, such as, but not limited to status epilepticus. Additionally, shortened inter-ictal periods compared to a reference inter-ictal value(s) may provide an additional and/or independent indication of a patient's having a risk/increased risk of an extreme seizure event and/or a patient having an extreme seizure event, such as, but not limited to status epilepticus. In various embodiments, post-ictal data may be logged/reported in logging/reporting module 265 and/or transmitted to the extreme epileptic event/state detection, quantification and risk determination unit 290, the SSI unit 295, memory 217 and/or database 250/255 as shown above with respect to FIG. 2. It is noted that those of ordinary skill in the art having the benefit of this disclosure will appreciate that the duration of inter-ictal states may be given by the times the body is not in the ictal or post-ictal states.

The seizure (extreme seizure) ranking unit 247 may include a seizure impact (PSimp) ranking unit 1017, in accordance with one or more embodiments. The seizure impact ranking unit 1017 may be adapted to receive PSimp data from PSimp unit 296, body data from body data collection module 275 site(s) data from the site(s) of seizure origin determination unit 293, seizure spread/intensity/duration data from seizure spread, duration and intensity determination unit 294, physical fitness/integrity data acquisition and determination unit 376, and/or other applicable and/or other data from various components of the MD 200 or from external sources such as physician's/caregiver's reports and/or tests results. The seizure impact ranking unit 1017 may be adapted to determine a seizure impact ranking, i.e., a relative determination of a seizure impact relationship to past values. In one embodiment, for example, the seizure impact ranking may be based upon a normal/normalized distribution of seizure impact values. The impact of seizure events may be determined based upon body data, site(s) data and/or spread data values relative to adaptable or pre-determined thresholds, responsiveness of a patient, and/or the like. Those of skill in the art would appreciate that quantitative or qualitative scales may be developed for each patient of for a population of patients. In various embodiments, seizure impact rankings may be logged/reported in logging/reporting module 265 and/or transmitted to the extreme epileptic event/state detection, quantification and risk determination unit 290, the SSI unit 295, memory 217 and/or database 250/255, as described above with respect to FIG. 2.

The seizure (extreme seizure) ranking unit 247 may include a QOL ranking unit 1012, in accordance with one or more embodiments. QOL ranking unit 1012, may receive data from QOL determination unit 274 (described above), from PSimp determination unit 296 or from PSimp ranking unit 1017 as well as from other units such seizure intensity ranking unit 1010 whenever applicable or useful. Additionally the QOL ranking unit 1012 may receive data from QOL questionnaires/instruments, structured or unstructured interviews of the patient as well as impressions, opinions or comments from the patient or caregivers. In various embodiments, QOL rankings may be logged/reported in logging/reporting module 265 and/or transmitted to the extreme epileptic event/ state detection, quantification and risk determination unit 290, the SSI unit 295, memory 217 and/or database 250/255, as described above with respect to FIG. 2.

The seizure (extreme seizure) ranking unit 247 may include a seizure burden ranking unit 1018, in accordance with one or more embodiments. In one embodiment, the seizure burden ranking unit 1018 may be adapted to receive seizure burden data from seizure burden unit 273, body data from body data collection module 275 site(s), from the PSimp unit 296, from the PSimp ranking unit 1017 and/or from the QOL ranking unit 1012 and/or from external sources such as a physician's/care-giver's report(s) or test(s) results. In another embodiment seizure burden ranking unit 1018 may receive data from the site(s) of seizure origin determination unit 293, seizure spread/intensity/duration data from seizure spread, duration and intensity determination unit 294 and/or other data from various components of the MD 200 or from external sources such as a physician's/caregiver report and/or tests results. The seizure burden ranking unit 1018 may be adapted to determine a seizure burden ranking, i.e., a relative determination of a seizure burden relationship to historical interval values, normative values and/or expected values. In one embodiment, for example, the seizure burden ranking may be based upon a normal/normalized distribution of seizure burden values. The burden of seizure events may be determined based upon body data, site(s) data and/or spread data values relative to adaptable or pre-determined thresholds, responsiveness of a patient, and/or the like, using time windows of at least one length. In various embodiments, seizure burden rankings may be logged/reported in logging/reporting module 265 and/or transmitted to the extreme epileptic event/state detection, quantification and risk determination unit 290, the SSI unit 295, memory 217 and/or database 250/255, as described above with respect to FIG. 2.

In one or more embodiments, the seizure duration ranking unit 1032, seizure spread ranking unit 1015, the seizure intensity ranking unit 1010, the seizure spread, duration and intensity determination unit 294, inter-seizure interval ranking unit 1025, the inter-seizure interval determination unit 1020, QOL ranking unit 1012, QOL unit 274, post-ictal ranking unit 1034, post-ictal determination unit 1033, PSimp ranking unit 1017, PSimp unit 296, seizure burden ranking unit 1018, seizure burden unit 273 and/or site(s) of seizure origin determination unit 293 may transmit information to and from each other for the purposes of determining their respective data outputs.

Seizure duration, intensity, extent of spread, ISI and all of their mathematical transformations, seizure burden and PSimp may be analyzed and interpreted in the context of for ultradian, circadian, or infradian rhythms (if present) and if trends are observed, said trends may be used to improve estimation of risks of having an extreme event. The efficacy of therapies may be also assessed in the context of these rhythms and optimized as needed, using these observations.

Figure 12:
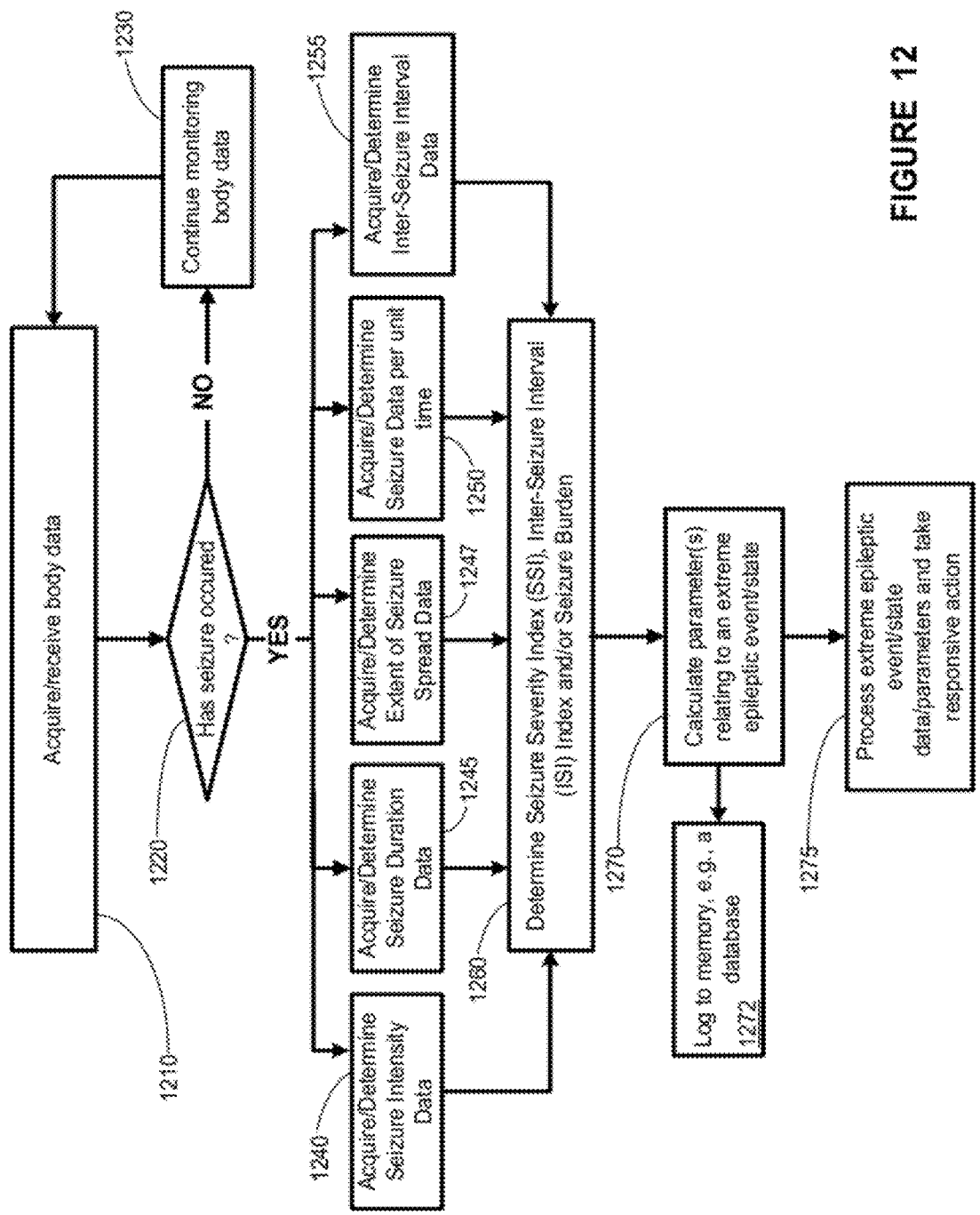
FIG. 12 provides a flowchart depiction of a method for identifying and/or managing a an extreme epileptic event/state, in accordance with one illustrative embodiment of the present invention.

Turning now to FIG. 12, a flowchart depiction of a method for taking action (warning, treating and/or logging) in response to determining a seizure event (extreme seizure event/state) is provided, in accordance with one illustrative embodiment of the present invention. The medical device 200 acquires and/or receives body data at (step 1210). Typically, the body data collection unit 275 receives the body data. The body data may be indicative of whether or not a seizure or extreme seizure event has occurred or is occurring. After performing buffering, amplification/conditioning and A/D conversion of the body data, the medical device 200 determines if a seizure is about to occur, is occurring or has occurred (step 1220). Typically the seizure determination module 299 makes this determination based upon one or more calculations. If the medical device 200 determines that no seizure or seizure event has occurred, the medical device 200 will continue to monitor for body data (step 1230 and return the flow to step 1210).

If the medical device determines (at step 1220) that a seizure is about to occur, is occurring or has occurred, the method proceeds to acquire seizure intensity data (step 1240), seizure duration data (step 1245), extent of seizure spread data (step 1247), time spent in seizure data (step 1250) and/or inter-seizure interval data (step 1250). In one embodiment, indices are acquired and/or determined using an SSI unit 295 (typically comprising an autonomic index unit 520, a neurologic index unit 510, an endocrine index 540, a metabolic index 542 and/or a tissue stress marker index unit 550). Steps 1240, 1245, 1247, 1250 and/or 1255 may begin at the same time and end at the same time (or at different times and in different combinations) according to different embodiments contemplated herein. In other words, steps 1240, 1245, 1247, 1250 and/or 1255 may begin and be completed substantially in parallel (i.e., at approximately the same time or at the same time) or independently of each other. The medical device determines an SSI value, an ISI index value and/or a seizure burden value using the seizure intensity data, seizure duration data, time spent in seizure data and/or inter-seizure interval data (step 1260). Typically, the SSI value is determined by SSI unit 295 (which may comprise an SSI determination unit (530), as described above with regard to FIG. 11). In one or more embodiments, additional data may also be used to determine the SSI value.

Still referring to FIG. 12, once an SSI value is determined (step 1260), the flow may proceed to step 1270. The medical device 200 calculates one or more parameters related to an extreme epileptic state/event (step 1270). The calculation of extreme epileptic state/event parameter(s) may be performed by an extreme epileptic event/state detection, quantification and risk determination unit 290. The calculation of extreme epileptic state/event parameter(s) may include a calculation using one or more SSI values. Upon calculating extreme epileptic state/event parameter(s), the MD 200 may log the parameters into memory, e.g., in a database (step 1272). The extreme epileptic state/event parameter(s) may be stored in an external memory (e.g., the database unit 250 and/or the local database unit 255), and/or in memory that is internal to the MD 200 (e.g., memory 217). The status epilepticus parameters may also be sent to an external device 265. From step 1270, the flow may proceed to the processing of extreme epileptic state/event data (step 1275). The medical device 200 may also take responsive action (at step 1275) such as a warning performed by warning unit 289 which may comprise a warning generation unit 610. In one or more embodiments, the responsive action may be taken according to (or similar to) the flowchart depicted in FIGS. 7-9 and 12.

Figure 13:
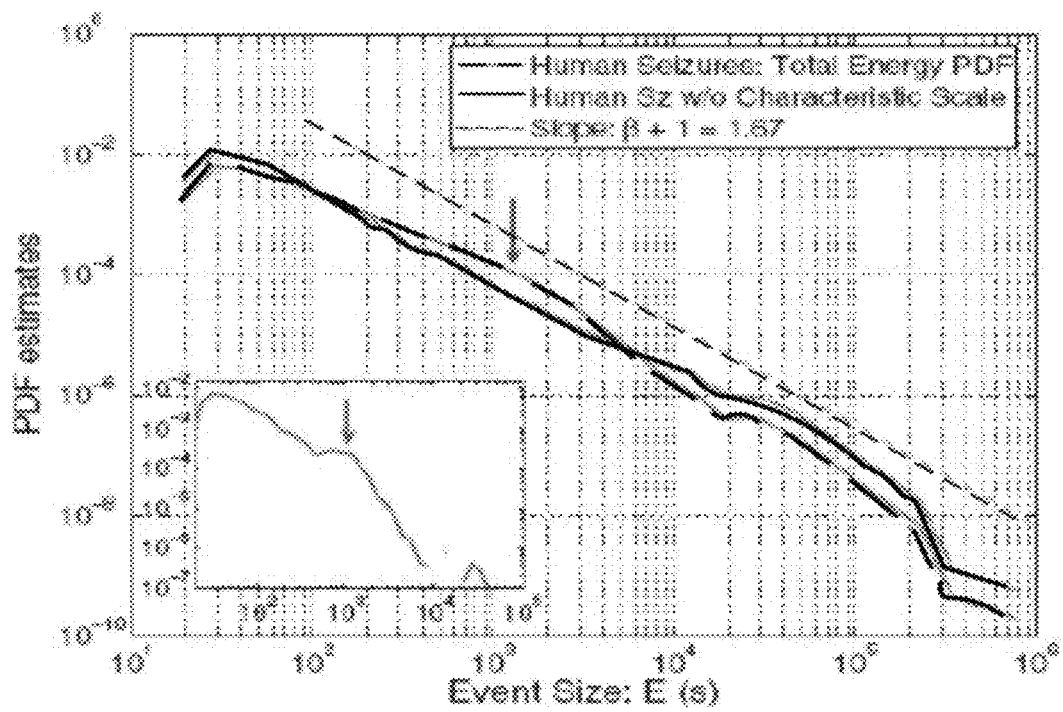
FIG. 13 provides a graphical representation of the probability density function of seizure energy estimated from subjects with pharmacoresistant seizures, in accordance with one illustrative embodiment.

Turning now to FIG. 13, a seizure energy probability density function (PDF) is depicted, according to one embodiment. For patients with pharmaco-resistant seizures, who are most in need of this invention, the probability of a seizure having energy larger than x is proportional to $x^{-\beta}$, where $\beta \approx -2/3$, wherein $\beta$ refers to the exponent of the PDF (the exponent of the probability density function is $(1+\beta)$). Accordingly, seizure energy may be inversely correlated with the probability of its occurrence. Therefore, in instances where seizure energy is higher, probability of seizure occurrence may be lower. The slight deviation from linearity indicated in FIG. 13 may be due to the presence of characteristic scales in the probability density function of seizure energy of some patients. The curves of FIG. 13 exemplify one of the statistical approaches for determining if an epileptic seizure event corresponds to status epilepticus. Seizures with energies above $5 \times 10^4$ (x-axis) are very severe (but infrequent) and could correspond to extreme events. Seizure energy (estimated, for example, as the product of peak seizure intensity and duration) may be used interchangeably with seizure severity.

Figure 14A:
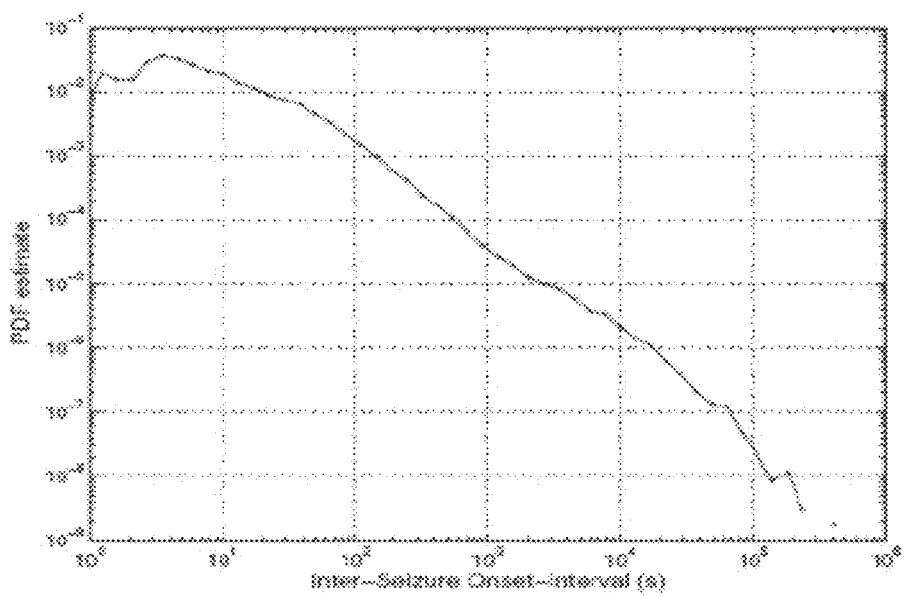
FIG. 14A provides a graphical representation one exemplary probability density function of inter-seizure intervals in patients with pharmacoresistant epilepsies, in accordance with one illustrative embodiment.

Turning now to FIG. 14A, one example of a probability density function of inter-seizure intervals (ISI) is illustrated. According to one embodiment, an estimate relating to a probability density function for inter-seizure intervals may be defined as the time elapsed from the onset of one seizure to the onset of the next. FIG. 14A illustrates that very short inter-seizure intervals could also indicate an increased risk of extreme events.

In one embodiment, a predictive analysis may be derived from the heavy tail structure of the inter-seizure interval distributions between successive events. The predictive analysis may indicate that the longer the elapsed time period since the occurrence of the previous seizure event, the longer the expected time until the next seizure event. (See, e.g., Osorio et al., PRE 2010).

Turning now to FIG. 14B, a graphical depiction of the temporal boundaries/metrics of: three states of interest: a) inter-ictal (defined as the period of time during which the value of an index is different from ictal and post-ictal values); b) ictal (defined as the period of time during which the value of an index is different from the inter-ictal and post-ictal values) and c) post-ictal (defined as the period of time during which the value of an index is different from inter-ictal and ictal values) is provided, in accordance with one illustrative embodiment. FIG. 14B shows a seizure related metric 1403 in a two-threshold (1405/1407) graphical representation of two illustrative seizure events: 1401 and 1402. The depicted seizure events 1401 and 1402 have ictal states 1482A and 1482B respectively and post-ictal states 1480A and 1480B respectively. In between seizure events 1401 and 1402 lie inter-ictal states 1483A and 1483B respectively. As illustrated, when the seizure related metric 1403 reaches/crosses the seizure threshold 1405 in an upward direction, the patient is said to be in an ictal state (1482A/1482B). When the seizure related metric 1403 reaches/crosses the post-ictal threshold 1407 in a downward direction, the patient is said to be in a post-ictal state (1480A/1480B) and when it crosses/reaches in an upward direction post-ictal threshold 1407 (without reaching/crossing ictal threshold 1405), the patient is said to be in an inter-ictal state.

FIG. 14B also depicts an inter-seizure interval (ISI) 1410A and 1410B, as well as inter-post-ictal intervals 1481A/1481B, for each illustrated seizure event 1401 and 1402 respectively, in accordance with one or more one embodiments. The illustrated ISI 1410A may be defined as the time elapsed between the onset of two consecutive (or non-consecutive) seizures or ictal states and the ISI 1410B may be defined as the time elapsed between the end of a seizure or ictal state and the onset of consecutive (or non-consecutive) seizures or ictal states, as shown in FIG. 14B. An ISI may also be defined as the time elapsed between the end of a post-ictal state and the onset of consecutive (or non-consecutive) seizures or ictal states (shown as inter-ictal state 1483A/1483B). Similarly, the illustrated inter-post-ictal intervals 1481A may be defined as the time elapsed between the onset of two consecutive (or non-consecutive) post-ictal states and the inter-post-ictal intervals 1481B may be defined as the time elapsed between the end of a post-ictal state and the onset of the next post-ictal state. The inter-ictal periods described herein are not exclusive, and other measures may be used as would be realized by one of ordinary skill in the art having the benefit of this disclosure.

As illustrated, the ISI 1410A has a shorter length than the ISI 1410B. In other words, the ictal states 1482A in seizure event 1401 are closer together in time than the ictal states 1482B in seizure event 1402. A shorter ISI may be an indication of a greater overall risk of having an extreme event and also of a higher burden and/or impact; progressive decrease (e.g., a trend) in ISI duration may be indicative of an increased risk for an extreme epileptic event/state. The longer the ISI (usually associated with longer inter-ictal periods) the greater the probability for recovery of body organs/systems to the inter-ictal state (baseline). The temporal length of ISIs may also be indicative of the overall probability of seizure occurrence. That is, in accordance with one or more embodiments, the longer the period between ictal states the lower the probability of a seizure occurring in a patient (see FIG. 17B below). In contrast, the shorter the ISIs, the higher the probability of a seizure occurring in a patient. The definitions of inter-ictal, ictal and post-ictal states apply to any and/or all autonomic, neurologic, metabolic, endocrine, tissue stress markers and quality of life indices. For example, heart rate, responsiveness/awareness, arterial pH, prolactin, CK, or quality of life during a seizure may be used to determine the onset and termination of the ictal and post-ictal states and the time of return to the inter-ictal state. This approach takes into account all patho-physiologic changes before the onset, during and following the termination to better track their "spatial" (referring to organs/systems spread) and temporal evolution, thus allowing the determination of each state according to each organ/system and each index.

Additionally, an increase above a threshold (e.g., seizure threshold 1405) may indicate an increased energy level in certain frequency bands related to a seizure event and/or extreme seizure event in a patient. A decrease below a threshold (e.g., post-ictal threshold 1407) may indicate a decreased energy level in certain frequency bands related to a seizure event and/or extreme seizure event in a patient. It is noted that both increases and decreases in energy of various frequency bands related to seizure events and/or extreme seizure events in a patient may provide information related to a body organ from which the energy level/frequency band was recorded.

Longer times spent in post-ictal states (e.g., 1480A/1480B) typically may be the result of a more severe seizure, a decline in a patient's overall health or brain health, longer periods of unresponsiveness, an increased risk of injury, status epilepticus and/or SUDEP, and the like. Large magnitude crossings below the downward post-ictal threshold 1407 typically may indicate similar risks to the patient. Additionally, the time spent in post-ictal states (e.g., 1480A/1480B) may be analyzed with and compared to the corresponding inter-seizure interval (ISI) and/or as inter-post-ictal intervals (e.g., 1481A/1481B) of a seizure event to assess trends of seizure severity and/or intensity.

In one embodiment, the post-ictal state (e.g., 1480A/1480B) severity may be used to determine and warn of a risk of an extreme epileptic event/state. In an exemplary embodiment, a downward crossing of a post-ictal threshold 1407 representing the ninetieth percentile of post-ictal severity may indicate an increased risk of an extreme epileptic event/state requiring a warning and/or other treatment/response. It is contemplated that different percentile values may be used to set the downward crossing post-ictal threshold 1407, and that the downward crossing post-ictal threshold 1407 may be adaptable. It is also contemplated that the thresholds 1405/1407 may be based upon a pre-determined or adaptable number of standard deviations of a normalized distribution of post-ictal severity of a patient. For example, if a value meets or exceeds three standard deviations from normal (i.e., the threshold may be seen as three standard deviations from normal), this may indicate that a warning of a risk/occurrence of an extreme epileptic state/event may be needed.

Figure 15:
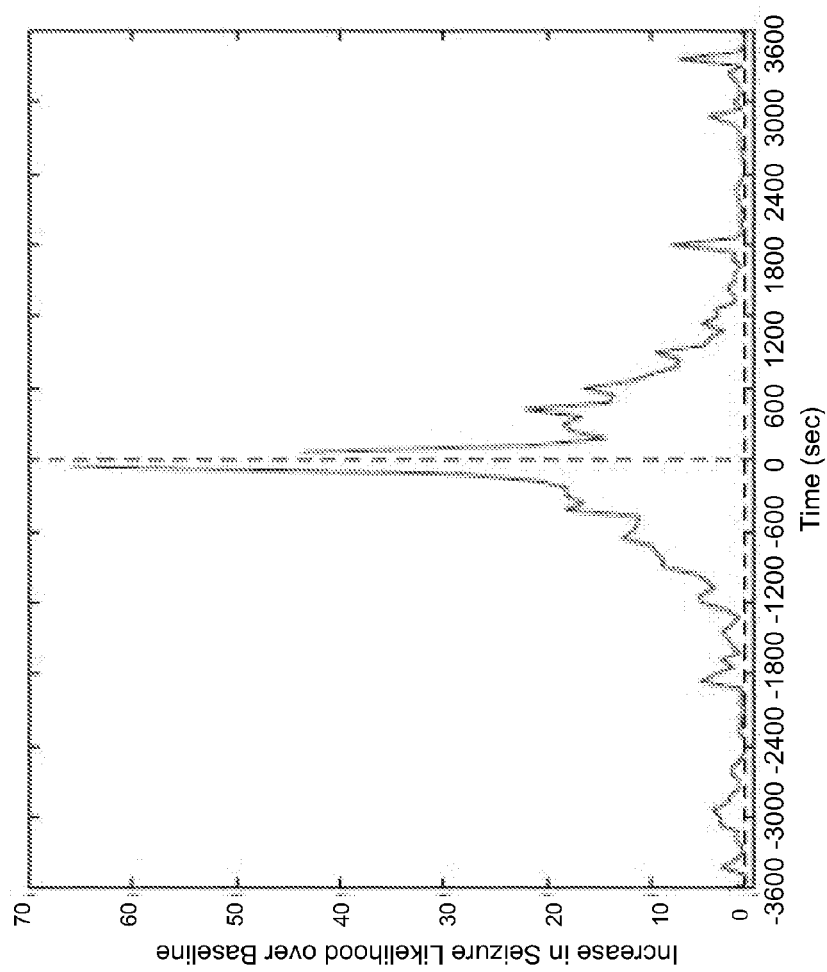
FIG. 15 provides a graphical representation of an increase in seizure likelihood (y-axis) over baseline as a function of time before and after a seizure as determined in a pooled group of patients is illustrated according to one illustrative embodiment.

Turning now to FIG. 15, a temporal distribution of the probability of seizure occurrence before and after a seizure, in accordance with one embodiment, is depicted. FIG. 15 illustrates a relationship of the probability of seizure occurrence within a window of time relative to (around) an actual occurrence of a seizure. As indicated in FIG. 15, for certain patients, there is an increased probability of seizure occurrence in the window beginning approximately 30 minutes prior to an actual occurrence of a seizure, and ending 30 minutes past the occurrence of the seizure. In other words, seizure occurrences in certain patients have a tendency to cluster with respect to time periods. In one embodiment, these clustering characteristics may provide for a quantitative statistical precursory diagnostic of impending seizures.

Figure 16A:
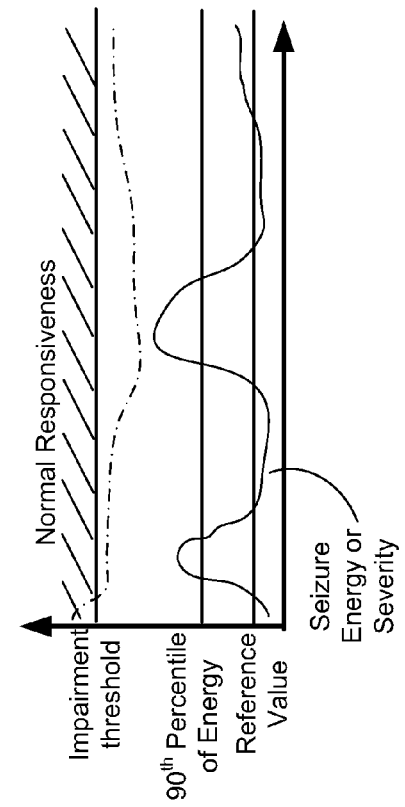
FIG. 16A graphically depicts changes in responsiveness/awareness and recovery to baseline as a function of seizure severity in a case on non-extreme events, in accordance with one illustrative embodiment.
Figure 16B:
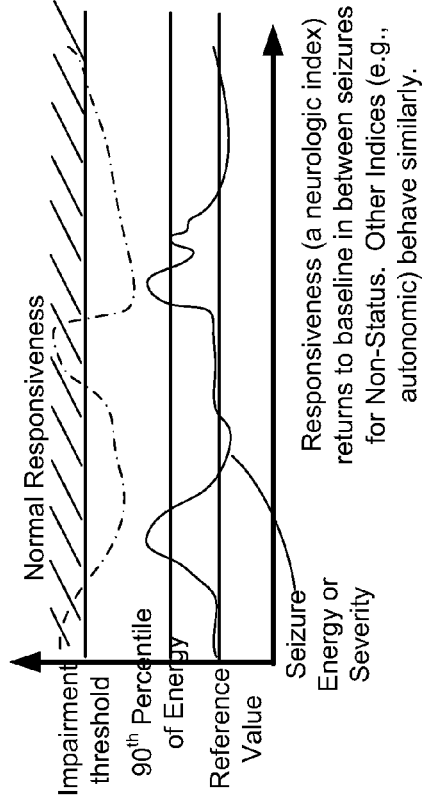
FIG. 16B depicts an example of an extreme epileptic state where responsiveness/awareness does not recover to baseline in-between seizures due to their severity, in accordance with one illustrative embodiment.

Turning now to FIGS. 16A and 16B, a relationship between metrics (in this example between responsiveness/awareness (e.g., based on cognitive tests) and seizure severity determined for example using heart rate) is depicted for a non-extreme epileptic state/event (FIG. 16A) and an extreme epileptic state/event (FIG. 16B), in accordance with one embodiment. As shown in FIG. 16A, responsiveness/awareness, returns to its inter-ictal values before the next seizure. It should be noted that a recovery of responsiveness/awareness to baseline or inter-ictal levels in between seizures is associated with a low probability of extreme event/state occurrence. In contrast, FIG. 16B depicts a seizure energy increasing to an extreme value (e.g., above the $90^{th}$ percentile of seizure energy values for that patient), indicative of an extreme epileptic event (e.g., status epilepticus). Notice that responsiveness/awareness does not recover to inter-ictal levels before the next seizure which further depresses responsiveness.

Figure 16D:
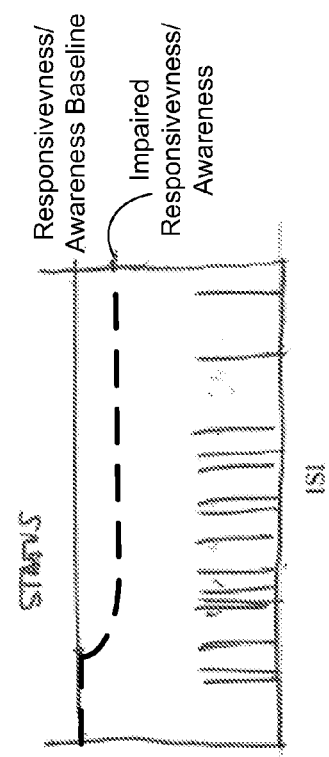
FIG. 16D depicts an illustrative example of changes in responsiveness/awareness associated with short inter-seizure intervals and compatible with an extreme epileptic event/state as responsiveness remains below baseline.
Figure 16C:
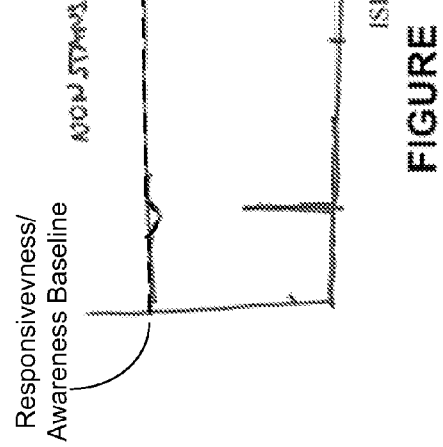
FIG. 16C depicts an example of changes in responsiveness/awareness as a function of inter-seizure interval in a non-extreme event case, in accordance with one illustrative embodiment.

Turning now to FIGS. 16C and 16D, a relationship between responsiveness/awareness and inter-seizure interval (ISI) is depicted for a non-extreme epileptic state/event (FIG. 16C) and an extreme epileptic state/event (FIG. 16D), in accordance with one embodiment. As shown in FIG. 16C, in a patient with relatively long ISI (i.e., infrequent seizure events) responsiveness/awareness recovers to inter-ictal levels before the next seizure. In contrast, FIG. 16D depicts relatively short ISIs (i.e., closely temporally spaced seizures) resulting in an extreme epileptic event/state (e.g., a status epilepticus state) during which responsiveness/awareness remains below inter-ictal levels (i.e., at an impaired responsiveness/awareness value).

Figure 17A:
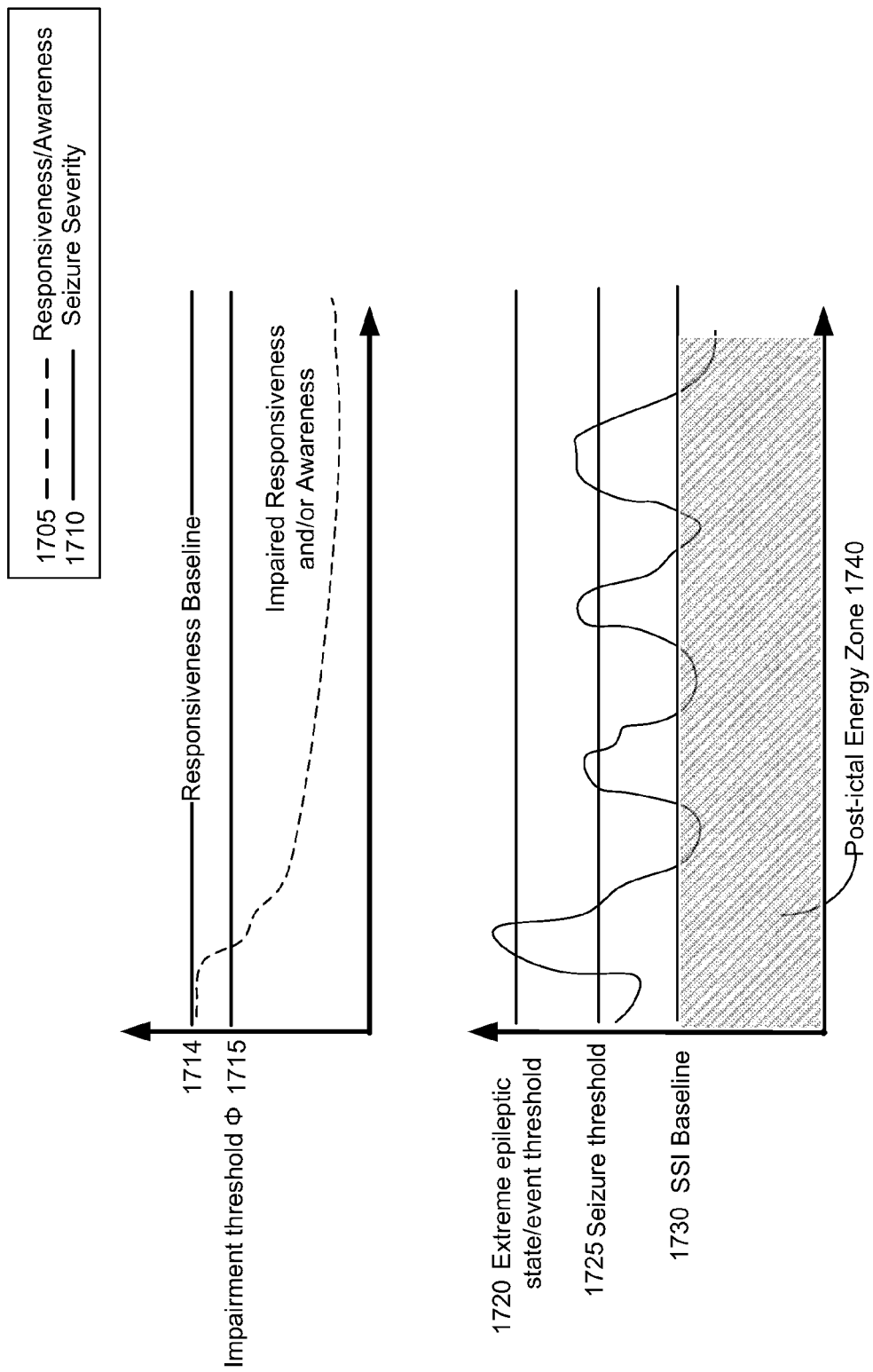
FIG. 17A provides a graphical representation of a seizure measure(s) and/or dimension(s) with more than one threshold (bottom panel), and where said thresholds may be above or below a reference threshold, in accordance with one illustrative embodiment.

Turning now to FIG. 17A, a graphical representation of various seizure-related measures/dimensions (y-axis) with respect to time (x-axis) are depicted, in accordance with one or more embodiments. Seizure Severity Index (SSI) 1710 (the product of intensity and duration in this embodiment; extent of spread was not considered) may be determined in reference to the seizure threshold 1725 by calculating the time elapsed between the upward and downward crossings multiplied by the maximum of the curve, above the seizure threshold 1725. Inter-seizure intervals may be calculated as the time elapsed between consecutive up-crossings of the seizure threshold or between a down-crossing of the seizure threshold 1725 and the next up-crossing. In addition to, or alternatively, any SSI, other indices such as responsiveness, awareness, kinetic data (e.g., body falls, limb direction, acceleration and trajectory), time spent in and magnitude of relative or absolute tachycardia (or bradycardia) hypoxia, lactic acidosis, and hypercortisolism respiratory failure, cardiac failure, pulmonary edema, cardiac arrhythmias, liver and/or renal failure, arterial hypertension, tissue hypercarbia and/or the like may be depicted. It should be noted that while only one seizure (the first) crosses the status epilepticus threshold 1720, the figure represents an extreme epileptic state due in addition to the increasing progressive depression of responsiveness/awareness and the short ISIs.

As a general matter, a patient's responsiveness and/or awareness, during and/or after an epileptic event or extreme epileptic event may be used as an indicator of epileptic event severity as well as a patient's health and/or disease state. A patient's responsiveness and/or awareness may be measured automatically using a variety of tests that rely on using audio, visual, olfactory or tactile signals to quantify its changes during the ictal and post-ictal periods compared inter-ictal. The responsiveness/awareness 1705 of a patient while not having seizures may be graphically viewed as a responsiveness baseline 1714; the responsiveness/awareness crossed an impairment threshold 1715 in the downward direction during a seizure. That is, as responsiveness/awareness 1705 decreases, the impairment threshold 1715 may be reached or crossed. The responsiveness/awareness 1705 of the patient may be determined before, during and/or after a seizure event in order to determine the patient's responsiveness/awareness 1705, the severity and/or intensity of a seizure event, a patient's risk of an extreme epileptic event/state and/or the like. That is, the more marked or longer a period of unresponsiveness, the more extreme the epileptic event or state, as discussed below with respect to FIG. 17B.

As depicted in FIG. 17A, a seizure threshold 1725 and an extreme seizure event/state threshold 1720 may be set for a patient. The seizure threshold 1725 and the extreme event/state threshold 1720 may be based upon a reference to a non-extreme or to an extreme reference value(s) selected from one or more of the following: the body data collection module 275, the physical fitness/integrity index unit 355, the physical fitness/integrity determination unit 376, the neurologic index unit 510, the autonomic index unit 520, the endocrine index unit 540, the metabolic index unit 542, the tissue stress marker index unit 550, the QOL unit 274, the SSI unit 295, the ISI unit 245, the seizure burden unit 273, the patient seizure impact unit 296, the site(s) of seizure determination unit 293, the seizure spread, duration and intensity determination unit 294, the seizure (extreme seizure) ranking unit 247, the seizure determination module 299, seizure intensity ranking unit 1010, seizure spread ranking unit 1015, inter-seizure interval ranking unit 1025, seizure duration determination unit 1030, post-ictal determination unit 1033, seizure impact ranking unit 1017, seizure burden ranking unit 1018, inter-seizure interval determination unit 1020, seizure duration ranking unit, the extreme seizure event/state detection, quantification and risk determination unit 290 and/or the extreme epileptic event/state confirmation unit 287. In one embodiment, an upward crossing of the seizure threshold 1720 by a seizure metric 1710 may indicate that a patient is having an extreme seizure event. In accordance with one embodiment, a downward crossing of a threshold 1730 by the seizure metric 1710 is indicative of it entering the post-ictal energy zone state 1740 associated with decreased responsiveness/awareness 1705 with complex partial or generalized seizures. As shown in FIG. 17A, successive seizure events and/or extreme seizure events (indicated by the upward crossings of the status threshold 1720 and/or the seizure threshold 1725) are associated in this embodiment with increasing impairment of responsiveness/awareness 1705.

Figure 17B:
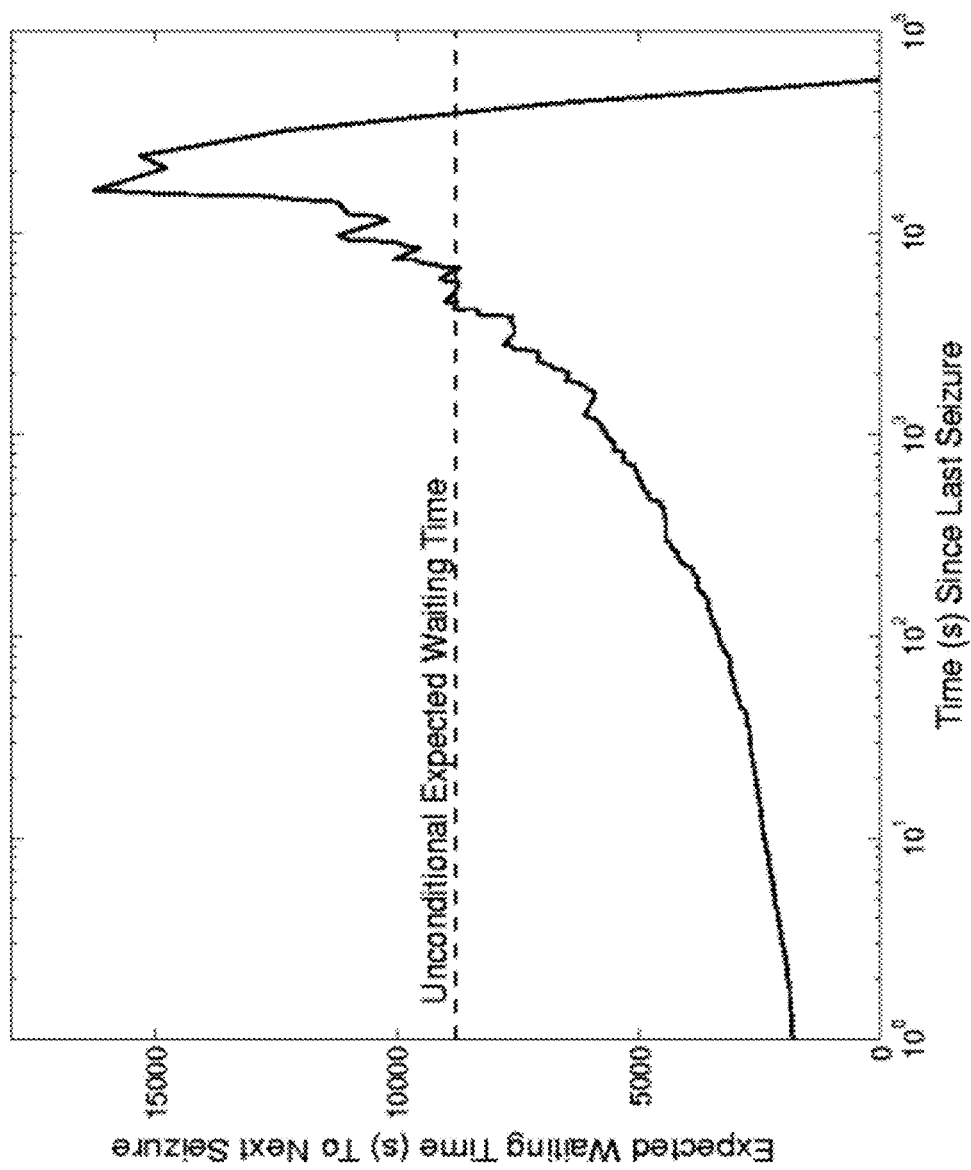
FIG. 17B depicts that in patients with pharmaco-resistant seizures, the longer the time elapsed from the last seizure, the longer the time until the next seizure, in accordance with one or more embodiments.

Turning now to FIG. 17B, a graphical representation of conditional (compared to the unconditional) probability of seizure occurrence as a function of time elapsed from the last seizure event, is depicted according to one or more embodiments. As shown, the longer the time elapsed from the last seizure, the longer the time to the next seizure and vice-versa. The shorter the ISI between events, the more probable that the brain is approaching an extreme epileptic state or is already in such a state. The solid curve is representative of the conditional probability, and the dashed line is representative of the unconditional.

Figure 18:
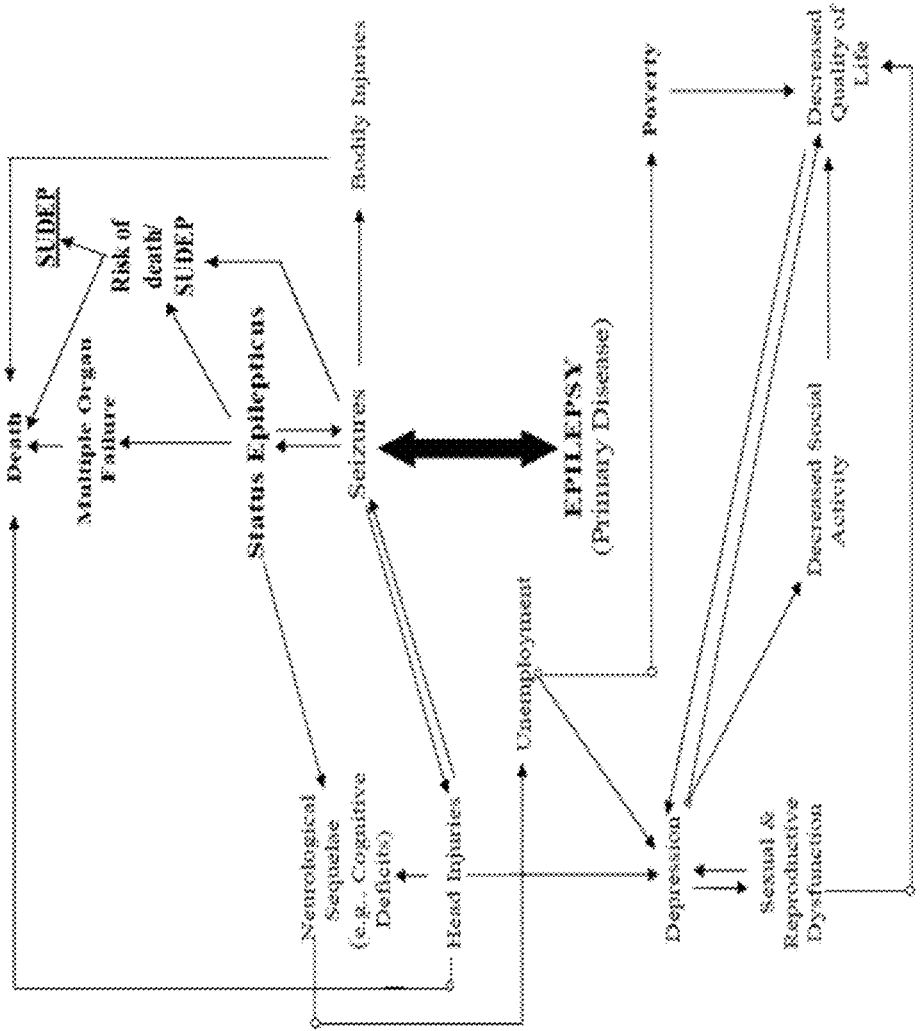
FIG. 18 provides a stylized diagram of impact of status epilepticus on body organ functions, seizures and quality of life.

Turning now to FIG. 18, a stylized graphical representation of inter-relations of epilepsy as a disease with its symptoms of and effects on patients is provided, in accordance with one or more embodiments. In one embodiment, the disease is epilepsy. Pharmaco-resistant seizures are associated with an increase in mortality and morbidity rates (compared to the general population and to epilepticus whose seizures are controlled by medications), eventual impairment of cognitive functions and mental health, and markedly degraded quality of life for patients and their families. Seizures may impair motor control, responsiveness to a wide class of stimuli, and other cognitive functions. Certain pharmacological agents used for treatment of epilepsy cause osteoporosis, reproductive dysfunction, liver and bone marrow damage, and in rare cases, death. FIG. 18 depicts relationships between epilepsy and some of its comorbidities, with the directionality of each arrow indicating an amplifying effect. For example, at exemplified in FIG. 18, seizures enhance epilepsy (and/or vice versa), which can lead to bodily injuries and/or head injuries which in turn may lead to other problems, such as cognitive deficits, depression, decreased social activity and decreased quality of life. Moreover, extreme events/state can lead to neurological sequelae, multiple organ failures, and to an increased risk of death.

The methods and apparatuses disclosed and claimed herein may be made and executed without undue experimentation in light of the present disclosure. While the methods and apparatus of embodiments of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

The invention claimed is:

1. A method for identifying an extreme seizure event in a patient, comprising:
   determining at least one of an autonomic index, a neurologic index, a metabolic index, an endocrine index, or a tissue stress index, said at least one determined index being based upon body data;
   identifying a seizure event based upon said at least one determined index;
   determining at least one seizure severity index (SSI) value indicative of the severity of said seizure event;
   comparing said determined at least one SSI value to at least one reference value; and
   identifying an occurrence of an extreme seizure event, based upon the comparison of said determined SSI value to said at least one reference value.

2. The method of claim 1, further comprising performing at least one action in response to identifying the occurrence of an extreme seizure event, said action comprising at least one of:
   setting a first flag indicative of said extreme seizure event;
   providing a first signal indicative of said extreme seizure event;
   providing a therapy to treat said extreme seizure event;
   issuing a warning in response to said identifying based upon at least one of: said comparing of said determined at least one SSI value to said at least one of a reference value, comparing the determined at least one SSI value to at least one extreme reference value, and providing said first signal indicative of said extreme seizure event if said first signal is provided;
   initiating a logging sequence of said extreme seizure event; and
   initiating a reporting sequence for said extreme seizure event.

3. The method of claim 2, wherein said logging sequence further comprises at least one of:
   storing at least one of said SSI value, a start time of said extreme seizure event, an end time of said extreme seizure event, a duration of said extreme seizure event, a time of providing said therapy, the type of said therapy, an outcome of said therapy and a time of issuing said warning into a memory of at least one of a medical device and a database operatively coupled to said medical device;
   storing at least one of a ranking of the SSI value and a characterization of the SSI value compared to at least one SSI value for a prior seizure event; and
   storing an activity signal indicative of the patient's activity state during a time period proximate to said seizure event.

4. The method of claim 2, wherein providing a therapy comprises providing at least one of an electrical therapy, a chemical therapy, or a thermal therapy to treat said extreme seizure event, and a supportive treatment comprising at least one of providing fluids, intubation, body cooling, brain cooling, providing oxygen, or providing non-seizure drugs to said patient.

5. The method of claim 2, further comprising:
   initiating an extreme seizure event confirmation of said identifying an occurrence of an extreme seizure event;
   receiving a response to said initiating; and
   performing at least one of:
      providing a second signal adapted to confirm or negate the extreme seizure event determination;
      setting a second flag confirming the extreme seizure event if the response to said requesting indicates that the patient is having an extreme seizure event; or
      deactivating the first flag if the response indicates that the patient is not having an extreme seizure event.

6. The method of claim 1 further comprising performing at least one of ranking the identified extreme seizure event in reference to at least one prior extreme event or determining the time elapsed since at least one of a plurality of prior extreme seizure events.

7. The method of claim 6 further comprising identifying a time spent in a state of an extreme seizure event over a time window, wherein the time window is at least one of a microscopic, a mesoscopic or a macroscopic time window.

8. The method of claim 1, wherein said at least one reference value is one of an extreme reference value and a non-extreme reference value; and wherein said at least one reference value is selected from the group consisting of a cardiac value, a respiratory value, a kinetic value, a responsiveness value or an awareness value.

9. The method of claim 8, wherein said at least one reference value is at least one of a measure of central tendency, a graphical analysis, a distribution analysis, or a statistical analysis, over at least one of a microscopic, a mesoscopic or a macroscopic time window.

10. The method of claim 8, wherein an extreme reference value is at least one of:

a value above the ninetieth percentile of a plurality of SSI values over a first time period; and a value beyond 2.5 standard deviations to the right or left of the mean for a normal or a normalized distribution.

11. The method of claim 1, wherein said extreme seizure event comprises at least one of a status epilepticus event or a pathophysiological effect resulting from an extreme epileptic state, the pathophysiological effect being selected from the group consisting of:

damage to brain tissue resulting in permanent/serious motor/visual/sensory/cognitive skills; respiratory failure, cardiac failure, pulmonary edema, cardiac arrhythmia, arterial blood acidosis, liver/renal failure, bed sores, bone fractures, abrasions, bruises, organ failure, multi-organ failure, arterial hypertension, tissue hypoxia and tissue acidosis.

12. The method of claim 1, further comprising:

determining if there is an elevated risk of sudden death in response to identifying an occurrence of said extreme seizure event; and issuing a warning of an elevated risk of sudden death in response to said determining that there is a an elevated risk of sudden death.

13. The method of claim 12, further comprising determining at least one of a risk of or a presence of at least one of decreasing heart rate variability (HRV), ST complex elevation, QT elongation, multi-focal premature ventricular contraction (PVC), ventricular tachycardia, ventricular fibrillation, or respiratory failure.

14. The method of claim 1, wherein said at least one SSI value is based upon at least one data set of seizure metric data related to a seizure event, said seizure metric data relating to a time period, wherein said at least one data set of seizure metric data is based at least upon said body data.

15. The method of claim 1, further comprising:

determining at least one of a quality of life index or a physical fitness/integrity index;

identifying a seizure impact on a patient based upon at least one of the quality of life index or the physical fitness/integrity index; and performing at least one of:

reporting the identified seizure impact;
logging the identified seizure impact; and
treating the patient based at least upon the identified seizure impact.

16. An apparatus, comprising:
a determination component adapted to:
determine at least one of an autonomic index, a neurologic index, a metabolic index, an endocrine index, or a tissue stress index, said at least one determined index being based upon body data;

identify a seizure event based upon said at least one determined index;

determine a seizure severity index (SSI) value indicative of the severity of said seizure event;

compare the determined SSI value to at least one reference value; and identify an occurrence of an extreme epileptic event, based upon the comparison of said determined SSI value to said at least one reference value.

17. The apparatus of claim 16, wherein said determination component further comprises at least one of:

a controller, said controller being adapted to:
control one or more operations of said apparatus;
process at least one of internal data or external data, said at least one of internal data or external data being associated with identifying an occurrence of an extreme epileptic event;
store data, said data comprising at least one of internal data, external data or processed data;
set a flag indicative of said extreme epileptic event;
provide a signal indicative of said extreme epileptic event;
provide a therapy based upon said extreme epileptic event;
issue a warning based upon said signal indicative of said extreme epileptic event;
determine a ranking of said extreme epileptic event compared to one or more previous extreme epileptic events;
initiate at least one of a logging sequence and a reporting sequence related to said extreme epileptic event; and
transmit a stored portion of data related to said extreme epileptic event to at least one of an external device or an external entity;

a memory adapted to:
store said data, said data comprising at least one of internal data, external data or processed data;
store said warning;
store said ranking; and
store a value indicative of the time spent in an extreme epileptic event;

a seizure determination module for detecting a seizure and determining at least one characteristic of the detected seizure;

a seizure severity index (SSI) unit to determine a value of an SSI; or an extreme epileptic event unit adapted to perform at least one of determining the presence of an extreme epileptic event or quantifying a risk of an extreme epileptic event.

18. The apparatus of claim 17, wherein said extreme epileptic event comprises an extreme epileptic event selected from the group consisting of a present status epilepticus state, or an increased risk of a status epilepticus state.

19. The apparatus of claim 16, wherein said at least one SSI value is based upon at least one data set of seizure metric data related to a seizure event, said seizure dataset related to a time period, wherein said at least one data set of seizure metric data is based at least upon said body data.

20. A non-transitive, computer-readable storage device for storing instructions that, when executed by a processor, perform a method for identifying an extreme seizure event in a patient, comprising:

determining at least one of an autonomic index, a neurologic index, a metabolic index, an endocrine index, or a tissue stress index, said at least one determined index being based upon body data;

identifying a seizure event based upon said at least one determined index;

determining at least one seizure severity index (SSI) value indicative of the severity of said seizure event;

comparing said determined at least one SSI value to at least one reference value; and identifying an occurrence of an extreme seizure event, based upon the comparison of said determined SSI value to said at least one reference value.

21. A non-transitive, computer-readable storage device for storing instructions that, when executed by a processor, perform the method as in claim 20 for identifying an extreme seizure event in a patient, wherein said at least one SSI value is based upon at least one data set of seizure metric data related to a seizure event, said seizure event occurring during a time period, wherein said at least one data set of seizure metric data is based at least upon said body data.

22. A method for identifying an extreme seizure event in a patient, comprising:

determining at least one of an autonomic index, a neurologic index, a metabolic index, an endocrine index, or a tissue stress index, said indices being based upon body data;

identifying at least two seizure events based upon said at least one determined index;

determining at least one seizure severity index (SSI) value related to at least one of said at least two seizure events;

determining at least one inter-seizure interval (ISI) value related to said at least two seizure events; and identifying an occurrence of a state of status epilepticus in the patient, based upon said determined SSI value and said determined ISI value.

23. The method of claim 22, further comprising performing at least one action in response to identifying the occurrence of a state of status epilepticus, said action comprising at least one of:

setting a first flag indicative of said state of status epilepticus;

providing a signal indicative of said state of status epilepticus;

providing a therapy to treat said state of status epilepticus;

issuing a warning in response to said identifying based upon at least one of said determined SSI value and said ISI value, or in response to said signal indicative of said state of status epilepticus if said signal is provided;

initiating a logging sequence of said state of status epilepticus; and initiating a reporting sequence for said state of status epilepticus.

24. The method of claim 23, wherein said logging sequence further comprises at least one of:

storing at least one of said SSI value, said ISI value, a start time of said state of status epilepticus, an end time of said state of status epilepticus, a duration of said state of status epilepticus, a time of providing said therapy, and a time of issuing said warning into a memory;

storing at least one of:

at least one of a ranking or a characterization of the SSI value compared to at least one SSI value for a prior seizure event; or at least one of a ranking or a characterization of the ISI value compared to at least one ISI value for a prior seizure event; or storing the time spent in a state of status epilepticus.

25. The method of claim 23, wherein providing a therapy comprises providing at least one of an electrical therapy, or a drug therapy, a drug to treat said extreme seizure event, and a supportive treatment comprising at least one of providing fluids, intubation, body cooling, brain cooling, providing oxygen, or providing non-seizure drugs to said patient.

26. The method of claim 23, further comprising:

initiating a status epilepticus state confirmation of said identifying an occurrence of a state of status epilepticus;

receiving a response to said initiating; and performing at least one of:

providing a second signal adapted to confirm or negate the status epilepticus determination;

setting a second flag confirming the state of status epilepticus if the response to said requesting indicates that the patient is in a state of status epilepticus; or deactivating the first flag if the response indicates that the patient is not in a state of status epilepticus.

27. The method of claim 22 further comprising identifying at least one of a time spent in a state of status epilepticus over a time window and a duration of a state of status epilepticus, said duration being based on said start time of said state of status epilepticus and said end time of said state of status epilepticus.

28. The method of claim 25, further comprising:

determining a risk of death in response to identifying an occurrence of said state of status epilepticus;

issuing a warning of a risk of death in response to determining the risk of death; and increasing said provided therapy in response to determining the risk of death.

29. The method of claim 25, wherein determining at least one of a risk of or a presence of at least one of decreasing heart rate variability (HRV), ST complex elevation, QT elongation, multi-focal premature ventricular contraction (PVC), ventricular tachycardia, ventricular fibrillation, pulmonary hypertension, or respiratory distress syndrome.

* * * * *